United States Patent
Valenzuela et al.

(10) Patent No.: US 10,468,141 B1
(45) Date of Patent: Nov. 5, 2019

(54) ANCESTRY-SPECIFIC GENETIC RISK SCORES

(71) Applicant: Asia Genomics Pte. Ltd., Singapore (SG)

(72) Inventors: Robert Keams Valenzuela, Marshfield, WI (US); Vishweshwaran Sridhar, Singapore (SG); Chun Meng Ong, Singapore (SG); Jia Yi Har, Singapore (SG); Pauline C. Ng, Singapore (SG); Mun Yew Wong, Singapore (SG)

(73) Assignee: ASIA GENOMICS PTE. LTD., Singapore (SG)

( * ) Notice: Subject to any disclaimer, the term of this patent is extended or adjusted under 35 U.S.C. 154(b) by 0 days.

(21) Appl. No.: 16/216,940

(22) Filed: Dec. 11, 2018

Related U.S. Application Data

(60) Provisional application No. 62/772,565, filed on Nov. 28, 2018.

(51) Int. Cl.
| | |
|---|---|
| *G06F 19/00* | (2018.01) |
| *G16H 50/30* | (2018.01) |
| *G16H 50/20* | (2018.01) |
| *C12Q 1/6827* | (2018.01) |
| *G06F 17/15* | (2006.01) |
| *G16B 20/00* | (2019.01) |
| *G16B 50/00* | (2019.01) |

(52) U.S. Cl.
CPC .......... *G16H 50/30* (2018.01); *C12Q 1/6827* (2013.01); *G06F 17/15* (2013.01); *G16B 20/00* (2019.02); *G16B 50/00* (2019.02); *G16H 50/20* (2018.01); *C12Q 2600/112* (2013.01); *C12Q 2600/118* (2013.01)

(58) Field of Classification Search
CPC .......... C12Q 2600/156; C12Q 1/6883; C12Q 1/6827; C12Q 2600/172; C12Q 2600/118; C12Q 2600/106; C12Q 1/6886; C12Q 2537/165; G06F 19/18; G06F 19/24; G06F 19/14; G06F 16/90335; G06F 16/904; G06F 17/5009; G06F 19/22; G06F 19/26; G06F 19/3431; G06F 2217/16; G01N 2800/50; G01N 33/6893; G06N 20/00; G06N 3/08; G06N 5/02; G06N 5/04; G16H 10/60; G16H 50/20; G16H 50/30; G16H 50/70
See application file for complete search history.

(56) References Cited

U.S. PATENT DOCUMENTS

| | | |
|---|---|---|
| 8,645,343 B2 | 2/2014 | Wong et al. |
| 9,213,947 B1 | 12/2015 | Do et al. |
| 9,218,451 B2 | 12/2015 | Wong et al. |
| 9,367,800 B1 | 6/2016 | Do et al. |
| 9,617,597 B2 | 4/2017 | Helgadottir et al. |
| 9,910,962 B1 | 3/2018 | Fakhrai-Rad et al. |

OTHER PUBLICATIONS

Bureau et al. (Bureau, A. et al. 2014 Bioinformatics vol. 30 No. 15 pp. 2189-2196).*
Auer, A. et al. 2012 Am J of Human Genetics vol. 91 pp. 794-808.*
Dewey, F.E.. et al. 2011 PLOSGenetics vol. 7 No. 9 e1002280, pp. 1-15.*
Heit et al. 2012 Journal of Thrombosis and Haemostasis vol. 10 pp. 1521-1531. A genome wide association study of venous thromboembolism identifies risk variants in chromosomes 1q24.2 and 9q.*
Hoffman and Witte, 2015 Trends in Genetics vol. 31 No. 10 pp. 556-563. Strategies for Imputing and analyzing rare variants in Association studies.*
Liu et al. 2014 Briefings in Bioinformatics vol. 16 No. 4 p. 549-562. Systematic assessment of imputation performance using the 1000 genomes reference panels.*
Von Rheenan et al. 2016 Nature Genetics vol. 48 No. 9 pp. 1043-1048. Genome wide association analyses identify new risk variants and the genetic architecture of amyotrophic lateral sclerosis.*
Wang et al. 2014 The American Journal of Human Genetics vol. 9, p. 770-783. Variant association tools for Quality control and analysis of large-scale sequence and genotyping array data.*
Warren et al. 2017 Nature Genetics vol. 49 No. 3 p. 483-495. Genome-wide association analysis identifies novel blood pressure loci and offers biological insights into cardiovascular risk.*

* cited by examiner

*Primary Examiner* — Mary K Zeman
(74) *Attorney, Agent, or Firm* — Wilson Sonsini Goodrich & Rosati

(57) ABSTRACT

Disclosed herein are methods and systems for calculating genetic risk scores (GRS) representing the likelihood that an individual will develop a specific trait based on the ancestry of the individual. Also provided are methods and systems for providing a recommendation to the individual to modify a behavior related to a specific trait, based on the individual's GRS for that trait.

20 Claims, 5 Drawing Sheets
Specification includes a Sequence Listing.

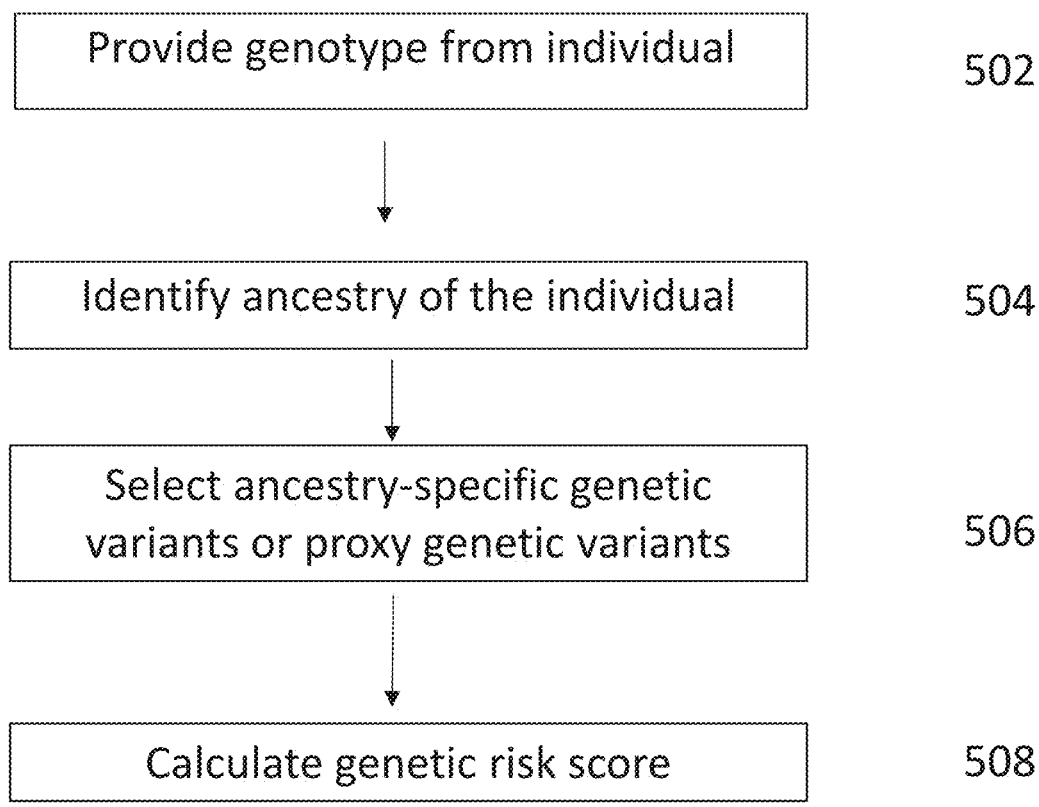

SEQUENCE LISTING

<160> NUMBER OF SEQ ID NOS: 218

<210> SEQ ID NO 1
<211> LENGTH: 101
<212> TYPE: DNA
<213> ORGANISM: Homo sapiens

<400> SEQUENCE: 1

```
tgtcctttct tagcagagca ggattttgac ctaaatttct gcaaactata rtcttatggt    60
tatgactctt tttgtaagtt gatcactcat tcacaaggat g                        101
```

```
<210> SEQ ID NO 2
<211> LENGTH: 101
<212> TYPE: DNA
<213> ORGANISM: Homo sapiens

<400> SEQUENCE: 2
aataagcccc ctcccactac ttcccattta tgaaatctgt ggcatactac vttactattt    60
tctatgaacc tttcctggat cacttaacat gtttactaca a                       101

<210> SEQ ID NO 3
<211> LENGTH: 101
<212> TYPE: DNA
<213> ORGANISM: Homo sapiens

<400> SEQUENCE: 3
ggcggggcag gcggcggcgc tgtcgggcgg gcaggggtgg cgggaggcgg bggcgcagcg    60
agcagcggcc tccagcgctg gtggctccct ttataggagc g                       101

<210> SEQ ID NO 4
<211> LENGTH: 101
<212> TYPE: DNA
<213> ORGANISM: Homo sapiens

<400> SEQUENCE: 4
ttgaattcgg gcgtctgctg gagtgtgccc aatgctatat gtcagttgag rttctaagac    60
ttggaagcca cagaaatgca gaatgccact ctgaggatac a                       101

<210> SEQ ID NO 5
<211> LENGTH: 101
<212> TYPE: DNA
<213> ORGANISM: Homo sapiens

<400> SEQUENCE: 5
agggcaggtc ggggaggctg tgcttctgcc tggagcccag ataccccaaa rccggagcca    60
gctgcctgct ggtgctgaag acgagaaagc acagcccggt c                       101

<210> SEQ ID NO 6
<211> LENGTH: 101
<212> TYPE: DNA
<213> ORGANISM: Homo sapiens

<400> SEQUENCE: 6
gggagatgtg gacagctccg gcagctcgtg ttcgcagtca ccctgaacgc yctcctctga    60
actcccacgt gtctccattc tcctaagctc aggtcgtcaa a                       101

<210> SEQ ID NO 7
<211> LENGTH: 101
<212> TYPE: DNA
<213> ORGANISM: Homo sapiens

<400> SEQUENCE: 7
ccttcccggg ctggggccag tgggccctgc ctaggggaga tgtggacagc bccggcagct    60
cgtgttcgca gtcaccctga acgccctcct ctgaactccc a                       101

<210> SEQ ID NO 8
<211> LENGTH: 101
<212> TYPE: DNA
<213> ORGANISM: Homo sapiens

<400> SEQUENCE: 8
```

```
actgcaactg ccaagcagcc ggggtaggag gggcgcccta ggcacagctg rgcccttgag    60
acagcagggc ttcgatgtca ggctcgatgt caatggtctg g                       101

<210> SEQ ID NO 9
<211> LENGTH: 101
<212> TYPE: DNA
<213> ORGANISM: Homo sapiens

<400> SEQUENCE: 9
gcggcctgaa ggatgctgat aaccgggagc ccgccctgg gttcggctat yccgggcacc    60
ccgggccggc ggggcgaggc tctccaattg ctgggccaga g                       101

<210> SEQ ID NO 10
<211> LENGTH: 101
<212> TYPE: DNA
<213> ORGANISM: Homo sapiens

<400> SEQUENCE: 10
gaaactaagg ataagtctcc cctctcccct gaatttcaag atacctgtgc rgttatcaat    60
atgtaaataa atgtaatttg aaagtcactt taaagattac t                       101

<210> SEQ ID NO 11
<211> LENGTH: 101
<212> TYPE: DNA
<213> ORGANISM: Homo sapiens

<400> SEQUENCE: 11
tacttctaat acattttatt ggcacaaaat tgtcacactg gccttaccta raggtagagg    60
actaggaaat atagcttaac cctgtgctca gggagaagaa a                       101

<210> SEQ ID NO 12
<211> LENGTH: 101
<212> TYPE: DNA
<213> ORGANISM: Homo sapiens

<400> SEQUENCE: 12
tatattgtgc ctactgtgtg ccaggcacta tatttagcac tttatatata ytaactgcag    60
ctggccttca agttggattt tttttttttt aggtcattcc t                       101

<210> SEQ ID NO 13
<211> LENGTH: 101
<212> TYPE: DNA
<213> ORGANISM: Homo sapiens

<400> SEQUENCE: 13
caattccatg gcccatagag ttacccttttt ccatatgcct ttgaaatgcc rgagatattt   60
gatcagtcag tgtccctcct ttcatgtgca cccccctgcca g                      101

<210> SEQ ID NO 14
<211> LENGTH: 101
<212> TYPE: DNA
<213> ORGANISM: Homo sapiens

<400> SEQUENCE: 14
ttacgtgaat ggaagcaaag tcaaggcaag tgtcaaggat gtgttgaaaa mcagatattc    60
aaaatggtgg gcaaaactat gcaaatgaca agggcaatgc t                       101

<210> SEQ ID NO 15
<211> LENGTH: 101
```

-continued

```
<212> TYPE: DNA
<213> ORGANISM: Homo sapiens

<400> SEQUENCE: 15
taagattcca cttgtgagca aggagaccat atacagtgcc ttctcccaga kcagaacata    60
cagagaaaaa aacaactgcc taatctggga aggtgagatt a                       101

<210> SEQ ID NO 16
<211> LENGTH: 101
<212> TYPE: DNA
<213> ORGANISM: Homo sapiens

<400> SEQUENCE: 16
gggatagaac caattgtatt cagtgagggc caagaaaatt gtaatgctgt rcccactaaa    60
caaaaaccat ctgggagcca gattcacact agggtggcca g                       101

<210> SEQ ID NO 17
<211> LENGTH: 101
<212> TYPE: DNA
<213> ORGANISM: Homo sapiens

<400> SEQUENCE: 17
cttgtagtga ctgagacaca gtgacattat atcacaacct cagaaaccac racataaacc    60
aaggaataat caatgccata gtttttaata gtgcaactag a                       101

<210> SEQ ID NO 18
<211> LENGTH: 101
<212> TYPE: DNA
<213> ORGANISM: Homo sapiens

<400> SEQUENCE: 18
agagagaaag acttacaaga ataaagtgag gaaaacacgg agttgatgca saagccccaa    60
catccaacct cgactcctct ttcgtagatg agaaactctg t                       101

<210> SEQ ID NO 19
<211> LENGTH: 101
<212> TYPE: DNA
<213> ORGANISM: Homo sapiens

<400> SEQUENCE: 19
ctgtcgccca ggctggagtg cagtggcgtg atctcggctc actgcaagct mcgcctccca    60
cgttcacgcc attctcctgc ctcagcctcc cgagtagctg g                       101

<210> SEQ ID NO 20
<211> LENGTH: 101
<212> TYPE: DNA
<213> ORGANISM: Homo sapiens

<400> SEQUENCE: 20
gccgtggccc ccttctccag tgctctcagg gagggtgcac caggcctgcc yccgccgtga    60
gaaactgcag tcccttctc cagtgctctc ggggagggtg c                        101

<210> SEQ ID NO 21
<211> LENGTH: 101
<212> TYPE: DNA
<213> ORGANISM: Homo sapiens

<400> SEQUENCE: 21
tcccacattt taccctgtga ggaaatcgag gctcagaaag gctgagtggc rtgctcaggg    60
```
catcagctcg tagggactga gccagggttg gagtccagac t                            101

<210> SEQ ID NO 22
<211> LENGTH: 101
<212> TYPE: DNA
<213> ORGANISM: Homo sapiens

<400> SEQUENCE: 22
tcaatatttg gatttagtct tccctttata gaaaataagg acatgttgta ytgtattctt        60
gcacactgaa gtctgggggc tacgattcat tcagctcatt g                           101

<210> SEQ ID NO 23
<211> LENGTH: 101
<212> TYPE: DNA
<213> ORGANISM: Homo sapiens
<220> FEATURE:
<221> NAME/KEY: modified_base
<222> LOCATION: (51)..(51)
<223> OTHER INFORMATION: a, c, t or g

<400> SEQUENCE: 23
tcctgggcgc catcgccgtg gaccgctaca tctccatctt ctacgcactg ngctaccaca        60
gcatcgtgac cctgccgcgg gcgcggcgag ccgttgcggc c                           101

<210> SEQ ID NO 24
<211> LENGTH: 101
<212> TYPE: DNA
<213> ORGANISM: Homo sapiens

<400> SEQUENCE: 24
agttcccagt tctcctcctg cctccggagc tgagtgatgg ctgtgcttct stgacagtgt        60
gaccctcaca ttagtcaaca ataaacaaca aaaactgcca c                           101

<210> SEQ ID NO 25
<211> LENGTH: 101
<212> TYPE: DNA
<213> ORGANISM: Homo sapiens

<400> SEQUENCE: 25
tatggtagaa gagagaggag ggtttctgtg ttatgaactg cacgagttgg ytgagctcag        60
tctatcacgt gtgtggtggg cacatggcca gactccatgt g                           101

<210> SEQ ID NO 26
<211> LENGTH: 101
<212> TYPE: DNA
<213> ORGANISM: Homo sapiens

<400> SEQUENCE: 26
cagccctgtg gttgatataa ggaggagcag agagccaggt ggggctgcag ytctgtttct        60
gggggaggtg ggctcagagg tggctggggc ttttctttaa g                           101

<210> SEQ ID NO 27
<211> LENGTH: 101
<212> TYPE: DNA
<213> ORGANISM: Homo sapiens

<400> SEQUENCE: 27
agagagaaag acttacaaga ataaagtgag gaaaacacgg agttgatgca saagccccaa        60
catccaacct cgactcctct ttcgtagatg agaaactctg t                           101

-continued

```
<210> SEQ ID NO 28
<211> LENGTH: 101
<212> TYPE: DNA
<213> ORGANISM: Homo sapiens

<400> SEQUENCE: 28
tcttagtctg aataaccttt tcctctgcag tattttgag cagtggctcc raaggcaccg      60
tcctcttcaa gaagtttatc cagaagccaa tgcacccatt g                        101

<210> SEQ ID NO 29
<211> LENGTH: 101
<212> TYPE: DNA
<213> ORGANISM: Homo sapiens

<400> SEQUENCE: 29
tcccacattt taccctgtga ggaaatcgag gctcagaaag gctgagtggc rtgctcaggg    60
catcagctcg tagggactga gccagggttg gagtccagac t                        101

<210> SEQ ID NO 30
<211> LENGTH: 101
<212> TYPE: DNA
<213> ORGANISM: Homo sapiens

<400> SEQUENCE: 30
atcctagact taatttatca aaggaatccc atgacttcca ggaatagcca kgcactactc    60
agtaattaaa caggagcagc ctgtggaaga aaggacttca t                        101

<210> SEQ ID NO 31
<211> LENGTH: 101
<212> TYPE: DNA
<213> ORGANISM: Homo sapiens
<220> FEATURE:
<221> NAME/KEY: modified_base
<222> LOCATION: (51)..(51)
<223> OTHER INFORMATION: a, c, t or g

<400> SEQUENCE: 31
tcctgggcgc catcgccgtg gaccgctaca tctccatctt ctacgcactg ngctaccaca    60
gcatcgtgac cctgccgcgg gcgcggcgag ccgttgcggc c                        101

<210> SEQ ID NO 32
<211> LENGTH: 101
<212> TYPE: DNA
<213> ORGANISM: Homo sapiens

<400> SEQUENCE: 32
atttctagac cgatgactgc atataaagca atgcttgagt gaagaaaaca rtagagtagg    60
tagaaatgga catcgatata gagaatttga tactgatgga t                        101

<210> SEQ ID NO 33
<211> LENGTH: 101
<212> TYPE: DNA
<213> ORGANISM: Homo sapiens

<400> SEQUENCE: 33
tcttagtctg aataaccttt tcctctgcag tattttgag cagtggctcc raaggcaccg     60
tcctcttcaa gaagtttatc cagaagccaa tgcacccatt g                        101

<210> SEQ ID NO 34
<211> LENGTH: 101
<212> TYPE: DNA
```

<213> ORGANISM: Homo sapiens

<400> SEQUENCE: 34 tacttttag ctgtgtgacc ttagataaat tattaaacct ttctgagctt yagttacctc    60 tttttatct acaaaatgga gataataaga cataccttt a    101

<210> SEQ ID NO 35
<211> LENGTH: 101
<212> TYPE: DNA
<213> ORGANISM: Homo sapiens

<400> SEQUENCE: 35
tcccacattt taccctgtga ggaaatcgag gctcagaaag gctgagtggc rtgctcaggg    60
catcagctcg tagggactga gccagggttg gagtccagac t    101

<210> SEQ ID NO 36
<211> LENGTH: 101
<212> TYPE: DNA
<213> ORGANISM: Homo sapiens

<400> SEQUENCE: 36
agttcccagt tctcctcctg cctccggagc tgagtgatgg ctgtgcttct stgacagtgt    60
gaccctcaca ttagtcaaca ataaacaaca aaaactgcca c    101

<210> SEQ ID NO 37
<211> LENGTH: 101
<212> TYPE: DNA
<213> ORGANISM: Homo sapiens

<400> SEQUENCE: 37
aagcaaacgg aacgatgctt ccctcaactc acttctggga aaacaattca magcacacag    60
tggcagttct tgtttttaaa caaagtggag ctgagagagg t    101

<210> SEQ ID NO 38
<211> LENGTH: 101
<212> TYPE: DNA
<213> ORGANISM: Homo sapiens

<400> SEQUENCE: 38
taagattcca cttgtgagca aggagaccat atacagtgcc ttctcccaga kcagaacata    60
cagagaaaaa aacaactgcc taatctggga aggtgagatt a    101

<210> SEQ ID NO 39
<211> LENGTH: 101
<212> TYPE: DNA
<213> ORGANISM: Homo sapiens

<400> SEQUENCE: 39
gctgagcaga ggatgaacat agccttggtc ggatcccttt atgagtcaga yggttttctt    60
cctgtgaggt gggtcctcag tgggagggac tagagacagg a    101

<210> SEQ ID NO 40
<211> LENGTH: 101
<212> TYPE: DNA
<213> ORGANISM: Homo sapiens

<400> SEQUENCE: 40
caattccatg gcccatagag ttaccctttt ccatatgcct ttgaaatgcc rgagatattt    60
gatcagtcag tgtccctcct ttcatgtgca cccccctgcca g    101

<210> SEQ ID NO 41
<211> LENGTH: 101
<212> TYPE: DNA
<213> ORGANISM: Homo sapiens

<400> SEQUENCE: 41
tgagcttcag tttcttaaaa tttaaaatga ggacaatacc atctatggcc rgggattaaa    60
tgctatgagg aatgtaaacc agatgtcagg taccatctct c                       101

<210> SEQ ID NO 42
<211> LENGTH: 101
<212> TYPE: DNA
<213> ORGANISM: Homo sapiens

<400> SEQUENCE: 42
gggatagaac caattgtatt cagtgagggc caagaaaatt gtaatgctgt rcccactaaa    60
caaaaaccat ctgggagcca gattcacact agggtggcca g                       101

<210> SEQ ID NO 43
<211> LENGTH: 101
<212> TYPE: DNA
<213> ORGANISM: Homo sapiens

<400> SEQUENCE: 43
tacttctaat acattttatt ggcacaaaat tgtcacactg gccttaccta raggtagagg    60
actaggaaat atagcttaac cctgtgctca gggagaagaa a                       101

<210> SEQ ID NO 44
<211> LENGTH: 101
<212> TYPE: DNA
<213> ORGANISM: Homo sapiens

<400> SEQUENCE: 44
gaaactaagg ataagtctcc cctctcccct gaatttcaag atacctgtgc rgttatcaat    60
atgtaaataa atgtaatttg aaagtcactt taaagattac t                       101

<210> SEQ ID NO 45
<211> LENGTH: 101
<212> TYPE: DNA
<213> ORGANISM: Homo sapiens

<400> SEQUENCE: 45
atttctagac cgatgactgc atataaagca atgcttgagt gaagaaaaca rtagagtagg    60
tagaaatgga catcgatata gagaatttga tactgatgga t                       101

<210> SEQ ID NO 46
<211> LENGTH: 101
<212> TYPE: DNA
<213> ORGANISM: Homo sapiens

<400> SEQUENCE: 46
tcttagtctg ataaccttt tcctctgcag tattttgag cagtggctcc raaggcaccg      60
tcctcttcaa gagtttatc cagaagccaa tgcacccatt g                        101

<210> SEQ ID NO 47
<211> LENGTH: 101
<212> TYPE: DNA
<213> ORGANISM: Homo sapiens
<220> FEATURE:

```
<221> NAME/KEY: modified_base
<222> LOCATION: (51)..(51)
<223> OTHER INFORMATION: a, c, t or g

<400> SEQUENCE: 47
tcctgggcgc catcgccgtg gaccgctaca tctccatctt ctacgcactg ngctaccaca    60
gcatcgtgac cctgccgcgg gcgcggcgag ccgttgcggc c                       101

<210> SEQ ID NO 48
<211> LENGTH: 101
<212> TYPE: DNA
<213> ORGANISM: Homo sapiens

<400> SEQUENCE: 48
acaagaacga aacagagttc aatggtctaa atttgcattc acgtgcaggg ytcctagaaa    60
tgatgatcct gcataattgt tgtggaaatc atttgtcttc t                       101

<210> SEQ ID NO 49
<211> LENGTH: 101
<212> TYPE: DNA
<213> ORGANISM: Homo sapiens

<400> SEQUENCE: 49
aaaatgaact ttgtgatgtc ttttctctat atttttggtt gggaggagta rctagaattc    60
ctctcctaaa ttagcattga atagcattct gtagaatatt a                       101

<210> SEQ ID NO 50
<211> LENGTH: 101
<212> TYPE: DNA
<213> ORGANISM: Homo sapiens

<400> SEQUENCE: 50
aaactagatc agtggttacc tggcagaatg ttgggtgagg gaaggtctcc rgatcgggag    60
ggaagtaaat gaggatggga ttacaaaggg acacaaagag a                       101

<210> SEQ ID NO 51
<211> LENGTH: 101
<212> TYPE: DNA
<213> ORGANISM: Homo sapiens

<400> SEQUENCE: 51
acaggagaag ggaggggaag ggcagaagtc cacagctggg agcacaggga ytcgggtgac    60
ttatgctggg gcctatttct cgttcatccc tacaactggc t                       101

<210> SEQ ID NO 52
<211> LENGTH: 101
<212> TYPE: DNA
<213> ORGANISM: Homo sapiens

<400> SEQUENCE: 52
gctataagag gggcgggcag gcatggagcc ccgtaggaat cgcagcgcca rcggttgcaa    60
ggtaaggccc cggcgcgctc cttcctcctt ctctgctggt c                       101

<210> SEQ ID NO 53
<211> LENGTH: 101
<212> TYPE: DNA
<213> ORGANISM: Homo sapiens

<400> SEQUENCE: 53
ctttaatgac tacaacatta tagaagttta aagcaggaga gattgtatcc ygatggaaat    60
```

```
gacaagaaaa gcttcagggg gaaggtgaca tttaagttgg a                 101
```

<210> SEQ ID NO 54
<211> LENGTH: 101
<212> TYPE: DNA
<213> ORGANISM: Homo sapiens

<400> SEQUENCE: 54

```
aagttaggct accagcatat ttgaatgcca ggtgaaatca aataatccta yactatctag    60
aagactttct tgatgccaag tccagagatg tcattgtgta g                 101
```

<210> SEQ ID NO 55
<211> LENGTH: 101
<212> TYPE: DNA
<213> ORGANISM: Homo sapiens

<400> SEQUENCE: 55

```
tttaaaccaa ccaccagata tctaaagagg gaatacagca cagtgttgga ragaaagtac    60
agaatagtat ttgagatcct agatgcagcc ggacgcggtg g                 101
```

<210> SEQ ID NO 56
<211> LENGTH: 101
<212> TYPE: DNA
<213> ORGANISM: Homo sapiens

<400> SEQUENCE: 56

```
gcaatgtcct tgtttgtgtt ctctcccagt gttccaggtt ctactgtcaa yccaggctca    60
ggctgtccca catcctccca cagaggtctt gctttgtttt g                 101
```

<210> SEQ ID NO 57
<211> LENGTH: 101
<212> TYPE: DNA
<213> ORGANISM: Homo sapiens

<400> SEQUENCE: 57

```
tgagaggaat tcaatctgaa caaatttaag caaaagggat ctttagtatg yggattttgt    60
cattttctag tagacaccaa ggacagggct gtagtggggc c                 101
```

<210> SEQ ID NO 58
<211> LENGTH: 101
<212> TYPE: DNA
<213> ORGANISM: Homo sapiens

<400> SEQUENCE: 58

```
agaggatgct aggtatctca aggtaggaaa gcatatctgt ggacagaaag ractgtagaa    60
tagccaaatc agagggaagg gccactctac ctagttcagt g                 101
```

<210> SEQ ID NO 59
<211> LENGTH: 101
<212> TYPE: DNA
<213> ORGANISM: Homo sapiens

<400> SEQUENCE: 59

```
aactgctatg tgtcctaagt gggaatgcta accctctga tcggctgaga ygcctacagc     60
ccagccttct ctaaatcccc aaaggccaga ccctgaaatg a                 101
```

<210> SEQ ID NO 60
<211> LENGTH: 101
<212> TYPE: DNA

<213> ORGANISM: Homo sapiens

<400> SEQUENCE: 60
tcaccaatat attattttac ttatcagtga aatcaaagga ctttacatat ytagattcca 60
aaacaaccta ttgtgataat ttcttaccta gaaaggtttc t 101

<210> SEQ ID NO 61
<211> LENGTH: 101
<212> TYPE: DNA
<213> ORGANISM: Homo sapiens

<400> SEQUENCE: 61
ttagaatgtc tgaattatta ttctaggttc cttgcgactg ctgtgaattt wgtgatgcac 60
ttggatagtc tctgttactc taaagtttta ataggtaaca g 101

<210> SEQ ID NO 62
<211> LENGTH: 101
<212> TYPE: DNA
<213> ORGANISM: Homo sapiens

<400> SEQUENCE: 62
tgccagcttc atagcctagt ctaggcatgc cagttgccca ctgtggcaat maatatctga 60
gcctgtggtt tttgccttag gtaaactgta gagatggact c 101

<210> SEQ ID NO 63
<211> LENGTH: 101
<212> TYPE: DNA
<213> ORGANISM: Homo sapiens

<400> SEQUENCE: 63
agcactggct tagaagatgt aggcagagat gacaagtgac acttcctgtc rtctgcctac 60
aagttcccaa agatcctccc ctttcttgct ctgttttcac c 101

<210> SEQ ID NO 64
<211> LENGTH: 101
<212> TYPE: DNA
<213> ORGANISM: Homo sapiens

<400> SEQUENCE: 64
ataagctttc tgcctcaatc tatctgtgta aggaacaggg tttctctgaa rgtatctttg 60
aaatactcta ccatcagttc atatttctac tttcacctaa g 101

<210> SEQ ID NO 65
<211> LENGTH: 101
<212> TYPE: DNA
<213> ORGANISM: Homo sapiens

<400> SEQUENCE: 65
cggttctaag caacagatac tgatactgac tcttaccaaa caaagcatga rcaaacaaag 60
atttatcaga agggtgcttg ttagtacctg tattcaaagg g 101

<210> SEQ ID NO 66
<211> LENGTH: 101
<212> TYPE: DNA
<213> ORGANISM: Homo sapiens

<400> SEQUENCE: 66
tttacagcat gatgaaatta catatatgat ggttaggtta ggttgcaagt yttggaatat 60
atgcagagga ataactttat tacaatgact atttactttt t 101

<210> SEQ ID NO 67
<211> LENGTH: 101
<212> TYPE: DNA
<213> ORGANISM: Homo sapiens

<400> SEQUENCE: 67
tagacaagca gagccctgcc aggcccatgg tgacctctgc agacctagga rctgcaggca    60
gagttggggg ctcgttcctg gggaggggcc cacccctgag g                      101

<210> SEQ ID NO 68
<211> LENGTH: 101
<212> TYPE: DNA
<213> ORGANISM: Homo sapiens

<400> SEQUENCE: 68
aggtagtttg gagaattgtt cattactgaa atcactgtcc ctcagttcac yggtcttgtc    60
tgcttcgtcg tcaaaaacag cttgactggg atgaccgaag t                      101

<210> SEQ ID NO 69
<211> LENGTH: 101
<212> TYPE: DNA
<213> ORGANISM: Homo sapiens

<400> SEQUENCE: 69
acaatcactc cttaaatatg gtggaacact tgaagcttga tatctagttt bgattcaaaa    60
gcttcatttc ccatattatg caaaactggt ggttgtgatc t                      101

<210> SEQ ID NO 70
<211> LENGTH: 101
<212> TYPE: DNA
<213> ORGANISM: Homo sapiens

<400> SEQUENCE: 70
aagttaggct accagcatat ttgaatgcca ggtgaaatca aaataatcta yactatctag    60
aagactttct tgatgccaag tccagagatg tcattgtgta g                      101

<210> SEQ ID NO 71
<211> LENGTH: 101
<212> TYPE: DNA
<213> ORGANISM: Homo sapiens

<400> SEQUENCE: 71
aactgctatg tgtcctaagt gggaatgcta accccctctga tcggctgaga ygcctacagc    60
ccagccttct ctaaatcccc aaaggccaga ccctgaaatg a                      101

<210> SEQ ID NO 72
<211> LENGTH: 101
<212> TYPE: DNA
<213> ORGANISM: Homo sapiens

<400> SEQUENCE: 72
actgtatcca ttatattctc atcaccatca catgtggttg aacgggcttc ygactaaaga    60
atctaaacat gtttaaaaca tttttcacct ccagtaaaac t                      101

<210> SEQ ID NO 73
<211> LENGTH: 101
<212> TYPE: DNA
<213> ORGANISM: Homo sapiens

```
<400> SEQUENCE: 73
aagttaggct accagcatat ttgaatgcca ggtgaaatca aaataatcta yactatctag    60
aagactttct tgatgccaag tccagagatg tcattgtgta g                      101

<210> SEQ ID NO 74
<211> LENGTH: 101
<212> TYPE: DNA
<213> ORGANISM: Homo sapiens

<400> SEQUENCE: 74
aactgctatg tgtcctaagt gggaatgcta acccctctga tcggctgaga ygcctacagc    60
ccagccttct ctaaatcccc aaaggccaga ccctgaaatg a                      101

<210> SEQ ID NO 75
<211> LENGTH: 101
<212> TYPE: DNA
<213> ORGANISM: Homo sapiens

<400> SEQUENCE: 75
actgtatcca ttatattctc atcaccatca catgtggttg aacgggcttc ygactaaaga    60
atctaaacat gtttaaaaca ttttttcacct ccagtaaaac t                     101

<210> SEQ ID NO 76
<211> LENGTH: 101
<212> TYPE: DNA
<213> ORGANISM: Homo sapiens

<400> SEQUENCE: 76
cctatacact tctatgtgtc ttttcttatt tctgtgctgc aaccaggtgg yataacctct    60
cacctgattc cttagctcta gtgaagttat tttcgtgcat g                      101

<210> SEQ ID NO 77
<211> LENGTH: 101
<212> TYPE: DNA
<213> ORGANISM: Homo sapiens

<400> SEQUENCE: 77 attttttgctg gaattataaa gctagaggcc ttctcttttcc atggaggttg ycacattcct   60
aacaaatgag cctggagctg ctggcagcca tctttaacat c                      101

<210> SEQ ID NO 78
<211> LENGTH: 101
<212> TYPE: DNA
<213> ORGANISM: Homo sapiens

<400> SEQUENCE: 78
gattagttat gagcatactt tggcaaatct ctgccccttt gggctgcagc mtcacaagct    60
gtgtggcgtt gggcaagtct atagaactca ggacaaatgg g                      101

<210> SEQ ID NO 79
<211> LENGTH: 101
<212> TYPE: DNA
<213> ORGANISM: Homo sapiens

<400> SEQUENCE: 79
cagcaaccat ccacagagac atcctggagc ctgggaagga aaggacaaa vagcccccctt    60 ttttaaattt ttttttatgtt tttgagacgg agtctcactc t                     101
```

```
<210> SEQ ID NO 80
<211> LENGTH: 101
<212> TYPE: DNA
<213> ORGANISM: Homo sapiens

<400> SEQUENCE: 80
ccctaccccc accctccatc ccctggtgcc ctgggggat ttattggagt rtatcaacct      60
ctccaacagc ccctctaaga gtcaggcttc aaagggtcct t                        101

<210> SEQ ID NO 81
<211> LENGTH: 101
<212> TYPE: DNA
<213> ORGANISM: Homo sapiens

<400> SEQUENCE: 81
ggagcagcag agtctgatgt tgtgtacttc agggagctgg agttctatga rggaagagcg    60
aggaggcatg tgggaggaag aacagccca ctgaggcctg c                         101

<210> SEQ ID NO 82
<211> LENGTH: 101
<212> TYPE: DNA
<213> ORGANISM: Homo sapiens

<400> SEQUENCE: 82
atgagaaaca gcgtcaaatc atctttcat gatcccaagc tgaaaggcaa kccctccaga     60
gagcgttatg tgacccacaa ccgagcacat tggtgacaga c                        101

<210> SEQ ID NO 83
<211> LENGTH: 101
<212> TYPE: DNA
<213> ORGANISM: Homo sapiens

<400> SEQUENCE: 83
tcttccctgg aggggctgtt ttcactgtga tgcccgcaac ataccaagag yggaatcctg    60
tctgaggagt gcagctccgg tctcaccatg tgggcagggc a                        101

<210> SEQ ID NO 84
<211> LENGTH: 101
<212> TYPE: DNA
<213> ORGANISM: Homo sapiens

<400> SEQUENCE: 84
agatgctgtc atgaagtcct agatagtcat cactttctaa caaggcccta ygctgaactt    60
aatctctgta agtggcagag gcatttgaaa cagagggctg c                        101

<210> SEQ ID NO 85
<211> LENGTH: 101
<212> TYPE: DNA
<213> ORGANISM: Homo sapiens

<400> SEQUENCE: 85
aaagtagaaa aattgtaagt agaattatcg ttcattgggg actgtctata mctcattaga    60
tgttctcagt cacagcctct attttatgaa taattgtttt a                        101

<210> SEQ ID NO 86
<211> LENGTH: 101
<212> TYPE: DNA
<213> ORGANISM: Homo sapiens

<400> SEQUENCE: 86
```

```
ctctgagatg tgctggcttc aggcaccagg tcggccacac actggagtag rgcaccaaac    60
aggttcttga agtccccaat tttaggcctt ggttcttgga t                        101

<210> SEQ ID NO 87
<211> LENGTH: 101
<212> TYPE: DNA
<213> ORGANISM: Homo sapiens

<400> SEQUENCE: 87
aaacctttaa cttaaaatta gaagcaagtc tgatcaagaa gtctcaagca maggctgagt    60
agtaatattt aagacaacac tgcttactaa agaaaagagt t                        101

<210> SEQ ID NO 88
<211> LENGTH: 101
<212> TYPE: DNA
<213> ORGANISM: Homo sapiens

<400> SEQUENCE: 88
tttctattcc aacgttcctt ggttattctg acttgtttga gaggaatgta yagatgattt    60
ttattttgcc gcagggctgt caatgctttt ggttcactta g                        101

<210> SEQ ID NO 89
<211> LENGTH: 101
<212> TYPE: DNA
<213> ORGANISM: Homo sapiens

<400> SEQUENCE: 89
gtgttttacc atacttcaat ttgttttcat tgtgttttg gcttatctgt racagctttt     60
caatcagctt cctttaattg aggacttgac ttggtttcta a                        101

<210> SEQ ID NO 90
<211> LENGTH: 101
<212> TYPE: DNA
<213> ORGANISM: Homo sapiens

<400> SEQUENCE: 90
ctttattttg ctactgcctt gacctcaaag gaatgtgata gtgtgaggta ygaatgctct    60
taataaacag gatcgatcaa gggtgcttga ctcttgttgt t                        101

<210> SEQ ID NO 91
<211> LENGTH: 101
<212> TYPE: DNA
<213> ORGANISM: Homo sapiens

<400> SEQUENCE: 91
gggcaatggt cccattttaa aatatgctgt cccattgtcc cctagagcct rctttaactt    60
gtcagaccat gtattccact tcatatgcaa gaggcatgca c                        101

<210> SEQ ID NO 92
<211> LENGTH: 101
<212> TYPE: DNA
<213> ORGANISM: Homo sapiens

<400> SEQUENCE: 92
tcaataaagc aactatacaa tcaagaaatg caacacagat acctaataac vacacggcaa    60
gaaaaaaacc taacatatca atattaatct tgaacataaa c                        101

<210> SEQ ID NO 93
<211> LENGTH: 101
```

```
<212> TYPE: DNA
<213> ORGANISM: Homo sapiens

<400> SEQUENCE: 93
tggttatcca gactcactca tcttcagctt ctcaggggtc caatcctgca rtatctagtg      60
ccactgctcc tttcttccat tcccattggc accccccagc c                         101

<210> SEQ ID NO 94
<211> LENGTH: 101
<212> TYPE: DNA
<213> ORGANISM: Homo sapiens

<400> SEQUENCE: 94
tcccgagcag cggttgctgc cgcccaccag cctcaggccc catgttgcat yacctgcacc      60
aagaacaatg aagcaagtag ttaatgggtg tgatggttta t                         101

<210> SEQ ID NO 95
<211> LENGTH: 101
<212> TYPE: DNA
<213> ORGANISM: Homo sapiens

<400> SEQUENCE: 95
atggaattct tcctatggtg tgaatgattc cttcccagat ggagactatg rtgccaacct      60
ggaagcagct gccccctgcc actcctgtaa cctgctggat g                         101

<210> SEQ ID NO 96
<211> LENGTH: 101
<212> TYPE: DNA
<213> ORGANISM: Homo sapiens

<400> SEQUENCE: 96
gaggaatgag aaggcagcaa tctttgctgt tctgcagcct tcgctggtaa yacccaggca      60
aatagggtct ggagtggacc tccatcaaac tgcagcagaa t                         101

<210> SEQ ID NO 97
<211> LENGTH: 101
<212> TYPE: DNA
<213> ORGANISM: Homo sapiens

<400> SEQUENCE: 97
ctatgtaaaa ttttagaatc agctgtcaac tttacaaaaa tttcttctgg rgttttaagt     60
gagattatgt ggactctgta gatccatctg gggagaagtg a                         101

<210> SEQ ID NO 98
<211> LENGTH: 101
<212> TYPE: DNA
<213> ORGANISM: Homo sapiens

<400> SEQUENCE: 98
tatgtttaac agcagcatga aaacagacta atatagtaaa tttctgccag kggagtgggg     60
cattgcttag aagataccca aaaatgtaga agtgagtttg g                         101

<210> SEQ ID NO 99
<211> LENGTH: 101
<212> TYPE: DNA
<213> ORGANISM: Homo sapiens

<400> SEQUENCE: 99
agaattaata ccatgaaaag ggggcagttc actcaacaaa tatactgata rgaaacagaa     60
```
tataagagcc aatagagaag tttttgttg agaagtataa t                         101

<210> SEQ ID NO 100
<211> LENGTH: 101
<212> TYPE: DNA
<213> ORGANISM: Homo sapiens

<400> SEQUENCE: 100
ttcttggtta tgctccccga cctgttccac cacaaacaca tgacaaaact ytgagatata    60
gatctagaaa gtcctcacag ccatctgatc aactgcagaa a                       101

<210> SEQ ID NO 101
<211> LENGTH: 101
<212> TYPE: DNA
<213> ORGANISM: Homo sapiens

<400> SEQUENCE: 101
ccttccattt gcaagaagca ctagtaattt tacacgaggg gtgaccatct scacggtcat    60
tattgcagga gctcagcggc atccacagct gcaggggccc a                       101

<210> SEQ ID NO 102
<211> LENGTH: 101
<212> TYPE: DNA
<213> ORGANISM: Homo sapiens

<400> SEQUENCE: 102
gagaagggag atggcggtag cagcgacgtg cccacctgtg atttctgggg bccttcttttt  60 ctctttgctg gttcagggac tcaagtccag gccaatttga c                       101

<210> SEQ ID NO 103
<211> LENGTH: 101
<212> TYPE: DNA
<213> ORGANISM: Homo sapiens

<400> SEQUENCE: 103
ttgttgtggc aactgggcca gtgggacagg aaaggcgtcc tgaagctctc rgctgggaag   60
ctcctgaagt tgctctgaac tgcagcagag gcagccggga g                       101

<210> SEQ ID NO 104
<211> LENGTH: 101
<212> TYPE: DNA
<213> ORGANISM: Homo sapiens

<400> SEQUENCE: 104
gcctgctgac agcgcacgat cagttcaagg caacactgcc cgaggctgac ygagagcgag   60
gtgccatcat gggcatccag ggtgagatcc agaagatctg c                       101

<210> SEQ ID NO 105
<211> LENGTH: 101
<212> TYPE: DNA
<213> ORGANISM: Homo sapiens

<400> SEQUENCE: 105
tagcctcaat gacgacctaa gctgcacttt tcccctagt tgtgtcttgc satgctaaag    60
gacgtcacat tgcacaatct taataaggtt tccaatcagc c                       101

<210> SEQ ID NO 106
<211> LENGTH: 101
<212> TYPE: DNA
<213> ORGANISM: Homo sapiens

```
<400> SEQUENCE: 106
cctagctgca ccccagcgcc tgggcccgcc ccacgctctg tccacaccca ygcgccccgg      60
gagcggggcc atgcctccag cccccagct cgcccgaccc a                           101

<210> SEQ ID NO 107
<211> LENGTH: 101
<212> TYPE: DNA
<213> ORGANISM: Homo sapiens

<400> SEQUENCE: 107
aatccccaat gtgaggggt catgatgatg ctgtgggcct ctgggcatca rtgtcatctc      60
acacccaaag tcagtactcc cccaagttct ccctatttcc c                          101

<210> SEQ ID NO 108
<211> LENGTH: 101
<212> TYPE: DNA
<213> ORGANISM: Homo sapiens

<400> SEQUENCE: 108
cccgtggagg gattgtcact tctggttccc tgtgggcagg aatggtttcc wcgtaggtca      60
ctggggtttt ggccaggaaa agggtatgaa attcatgtgc c                          101

<210> SEQ ID NO 109
<211> LENGTH: 101
<212> TYPE: DNA
<213> ORGANISM: Homo sapiens

<400> SEQUENCE: 109
ctgtccccca cccccaattt tctttccaaa ctcctaaggg aggaaagagg rgactcactc      60
tttctggcat ctgccaccttt ctcagctgcc cgcttctcag c                         101

<210> SEQ ID NO 110
<211> LENGTH: 101
<212> TYPE: DNA
<213> ORGANISM: Homo sapiens

<400> SEQUENCE: 110
tgacaaggag aaatagatta gagagaatca caggagaaat ttgagatgca rggccaaacc      60
aaaaagccca ccaaggtcaa aactaaatga aatgtgaact t                          101

<210> SEQ ID NO 111
<211> LENGTH: 101
<212> TYPE: DNA
<213> ORGANISM: Homo sapiens

<400> SEQUENCE: 111
aaaggctctt acccttggct ctcccttttcc cctcagcctc ctgaccaacc yccacatggc     60
cctgtgtggc atcccgtgcc ccctcctctt gggaactgta a                          101

<210> SEQ ID NO 112
<211> LENGTH: 101
<212> TYPE: DNA
<213> ORGANISM: Homo sapiens

<400> SEQUENCE: 112
aaaaaatttc ttgaatggat gagcctgtat accctctact tccaattcac rgtcatcaca     60
acataacaga tgaaaaacac tcttcatttg tcttaaaagc t                          101
```

<210> SEQ ID NO 113
<211> LENGTH: 101
<212> TYPE: DNA
<213> ORGANISM: Homo sapiens

<400> SEQUENCE: 113
tcccttgggt gtgtaatcta acatagtgac aagttctgga gattagggca ygggcatctt    60
tgggggttat tattctgctt atcccaagaa tgttaccctt t                        101

<210> SEQ ID NO 114
<211> LENGTH: 101
<212> TYPE: DNA
<213> ORGANISM: Homo sapiens

<400> SEQUENCE: 114
gtgaccttat gttttggcag ctttaaaact atgtgatatg cacagtaagt rttttaaaac    60
acattttaat tttctccagg actgttagta ctaatatgat a                        101

<210> SEQ ID NO 115
<211> LENGTH: 101
<212> TYPE: DNA
<213> ORGANISM: Homo sapiens

<400> SEQUENCE: 115
tgagccactg cgcctggcca aaactggttt ctagtttatg agttcagcag rtatttgact    60
ctggattcct caatttagtg atatcacaca aaatggtata a                        101

<210> SEQ ID NO 116
<211> LENGTH: 101
<212> TYPE: DNA
<213> ORGANISM: Homo sapiens

<400> SEQUENCE: 116
cctttgagag tttttaatct atcctagaca caggcacagc acgaaaagag raaacatccc    60
agcttcatta ggggaaattt atagcttgcc tagggtcacc a                        101

<210> SEQ ID NO 117
<211> LENGTH: 101
<212> TYPE: DNA
<213> ORGANISM: Homo sapiens

<400> SEQUENCE: 117
gtctaatcct acaatatttc caaacctcac ccatcccaga ataaataaat rtatgagatg    60
acattgcaaa ttggacgccc aatgttcaca aaagctgact c                        101

<210> SEQ ID NO 118
<211> LENGTH: 101
<212> TYPE: DNA
<213> ORGANISM: Homo sapiens

<400> SEQUENCE: 118
gacagccaac agcgcgccta acttggagcg aatcctcttc gggctttcca ragtgcgggg    60
gatagataaa gagtagctgg ggagacgccc cctgaccttg c                        101

<210> SEQ ID NO 119
<211> LENGTH: 101
<212> TYPE: DNA
<213> ORGANISM: Homo sapiens

<400> SEQUENCE: 119

```
tacttgactt tcagtacctc ccattgctga gccttttgag gattctctta ygtattcata    60
agtgtgattc tcattttcc agtgactcat tttccttgta t                        101
```

<210> SEQ ID NO 120
<211> LENGTH: 101
<212> TYPE: DNA
<213> ORGANISM: Homo sapiens

<400> SEQUENCE: 120

```
ttctcctctc ttaactctca ttaggccaac tggcaagttt agatgatgtc rtttagaaaa    60
attggtcaaa actagaatat aaacataacg tgcaatattc c                       101
```

<210> SEQ ID NO 121
<211> LENGTH: 101
<212> TYPE: DNA
<213> ORGANISM: Homo sapiens

<400> SEQUENCE: 121

```
aggagacatt cagatcacaa atggttgaac cctgggagga catcaaaaga ytgtttccaa    60
agataagttt ctcagaactg gaatcctccg aaatgctctg c                       101
```

<210> SEQ ID NO 122
<211> LENGTH: 101
<212> TYPE: DNA
<213> ORGANISM: Homo sapiens

<400> SEQUENCE: 122

```
gctcatggag cttcctccag cccagcctct gttcagtttt tccaaggctt rtcacagaaa    60
gagggctggg gtgttatttt taagtcttag ctacccagaa t                       101
```

<210> SEQ ID NO 123
<211> LENGTH: 101
<212> TYPE: DNA
<213> ORGANISM: Homo sapiens

<400> SEQUENCE: 123

```
attgttaaag aagagtgatc cctttgtgtt tcagcttggc acacagaaac kgttttaatt    60
taacagtcca gctcctttaa tagatcaatt ctctattgtg g                       101
```

<210> SEQ ID NO 124
<211> LENGTH: 101
<212> TYPE: DNA
<213> ORGANISM: Homo sapiens

<400> SEQUENCE: 124

```
gcaaagtctg agtgcttgtt aaccagcttt gccagttccg tgggtgtggc mtcaggcaat    60
tttgctttta gtcgctctgc cagtctgaaa aaccatttaa a                       101
```

<210> SEQ ID NO 125
<211> LENGTH: 101
<212> TYPE: DNA
<213> ORGANISM: Homo sapiens

<400> SEQUENCE: 125

```
ttccctcttc caagacaata taatatagtt atgtcacagt tctatttgca yggtgtaaaa    60
aattccatgt ttcattgtct tcaacgagtt tatgctttgg a                       101
```

<210> SEQ ID NO 126

```
<211> LENGTH: 101
<212> TYPE: DNA
<213> ORGANISM: Homo sapiens

<400> SEQUENCE: 126
cagagggact actacttgct tccaaagcta acaataaaaa atacctggct ktgtgagata      60
attaagagac agagatttgc tgggcatggt ggctcacgcc t                         101

<210> SEQ ID NO 127
<211> LENGTH: 101
<212> TYPE: DNA
<213> ORGANISM: Homo sapiens

<400> SEQUENCE: 127
cctggcagaa ctaccacctg aacgactgga tggaggagga ataccgccac wtcccggggg      60
agtacgtccg cttcaccggc taccctgct cctggaccttt c                         101

<210> SEQ ID NO 128
<211> LENGTH: 101
<212> TYPE: DNA
<213> ORGANISM: Homo sapiens

<400> SEQUENCE: 128
gctagtgttt taaagttatg taaaaagaca gactgggcaa catggtgaaa yccccatctc      60
tacaaaaaag aaaaaaaaaa ttaacagggt gtggtggtgc a                         101

<210> SEQ ID NO 129
<211> LENGTH: 101
<212> TYPE: DNA
<213> ORGANISM: Homo sapiens

<400> SEQUENCE: 129
aaagaaaggg ggaaagaatg ctctgagtgc ctactgtatt ttaagcactg kgacatacac      60
agttttacac tgtttaattt aaactttgta gccagtcaat g                         101

<210> SEQ ID NO 130
<211> LENGTH: 101
<212> TYPE: DNA
<213> ORGANISM: Homo sapiens

<400> SEQUENCE: 130
tcaccagtaa tggcatggcc tggtgtcggg agaacattga cacctcccac rgtgatgtgg      60
tgtttgctgg cgatggcatt gagggctcac ctgccaaaga t                         101

<210> SEQ ID NO 131
<211> LENGTH: 101
<212> TYPE: DNA
<213> ORGANISM: Homo sapiens

<400> SEQUENCE: 131
gcagcggcac ggtcaccttc tcactgagct ttgatgagcc tcagaagaac kccatggccc      60
acaggaattc tacgcaccag aactccctgg aggcccagaa a                         101

<210> SEQ ID NO 132
<211> LENGTH: 101
<212> TYPE: DNA
<213> ORGANISM: Homo sapiens

<400> SEQUENCE: 132
tgttggagct tctgttctcc tgcagaaaac ctgacaataa acaatgaaca bataaataag      60
```

```
aacacctcca gtagttaagt gctatctgaa aaacaagaag g                         101

<210> SEQ ID NO 133
<211> LENGTH: 101
<212> TYPE: DNA
<213> ORGANISM: Homo sapiens

<400> SEQUENCE: 133
ctgacctgta atttaattta aaagccctga gcaggctggg tgcggtacct mattcctata    60
atcccagcat tttgggaggc tgaggtggga ggattgtttg a                        101

<210> SEQ ID NO 134
<211> LENGTH: 101
<212> TYPE: DNA
<213> ORGANISM: Homo sapiens

<400> SEQUENCE: 134
ttctactcct tggtcctagc tttgttccta ggcgctgtgc cgctgtgtca yccaccctgc    60
cctgtacaat atgcaggaag caagcgagga ggggtgcct c                         101

<210> SEQ ID NO 135
<211> LENGTH: 101
<212> TYPE: DNA
<213> ORGANISM: Homo sapiens

<400> SEQUENCE: 135
ttctcaagga cctcctttcc ctgccctcct gcaccccatc accccacaag rtttcacagc    60
tgcagagaaa gcttcatctg gtaactagtg ttacgggttt a                        101

<210> SEQ ID NO 136
<211> LENGTH: 101
<212> TYPE: DNA
<213> ORGANISM: Homo sapiens

<400> SEQUENCE: 136
tttactgtta ttctggccaa gtttgagtgg tgatggtgat aagtaagtgc rtgtgtgtgt    60
gtgtgtgtgt gtgtgtgtgt gtgtgtgtgt gtgttcaatt t                        101

<210> SEQ ID NO 137
<211> LENGTH: 101
<212> TYPE: DNA
<213> ORGANISM: Homo sapiens

<400> SEQUENCE: 137
gaacaaaaaa ccaaatgcat acctttgact acaaagttct acttcctctg ygtaactcaa    60
aacttaaatt ccgggagcac aaaagctgct tcagagttgt a                        101

<210> SEQ ID NO 138
<211> LENGTH: 101
<212> TYPE: DNA
<213> ORGANISM: Homo sapiens

<400> SEQUENCE: 138
cctgcagcag ttcctgtgcc tttaaagcct cccctcccccc cgccccgccc scaggccact   60
aggggaggga aggaggagct gggtcacagc aggaatctt a                         101

<210> SEQ ID NO 139
<211> LENGTH: 101
<212> TYPE: DNA
```

<213> ORGANISM: Homo sapiens

<400> SEQUENCE: 139
atgtccccca catcccaata ctgttttgga gaaaggtact tgcatttgca ktatggaaat    60
tatttgtatt atttcaaaca tttggagcat ctgcttgcct g                       101

<210> SEQ ID NO 140
<211> LENGTH: 101
<212> TYPE: DNA
<213> ORGANISM: Homo sapiens

<400> SEQUENCE: 140
gttcccccac agggagaccc acagcagaga catgactcac aggtggcatc rggtcccttt    60
gagtctctct ggtgggagaa tctcaaccca cagagtagga t                       101

<210> SEQ ID NO 141
<211> LENGTH: 101
<212> TYPE: DNA
<213> ORGANISM: Homo sapiens

<400> SEQUENCE: 141 ttttttttc cgctgtgcta atgtagggag aagttgttgg aggtcacgtc rcagttcaca    60
gcaaccatct atgtttggga gcaaggatgc tggaaataga a                       101

<210> SEQ ID NO 142
<211> LENGTH: 101
<212> TYPE: DNA
<213> ORGANISM: Homo sapiens

<400> SEQUENCE: 142
gtttcctcaa cagtgaaata gggacatggt caccttcagg gggcagttat raggctcagg    60
gtagggtatg ttccaggcat ggctatgccg cactgtttat c                       101

<210> SEQ ID NO 143
<211> LENGTH: 101
<212> TYPE: DNA
<213> ORGANISM: Homo sapiens

<400> SEQUENCE: 143
agcaatcaga agtgctttcc ctggatttaa taattagatg ggagataaga yctttgaagt    60
aaagttaaag gcctttctac ctagaccaca gcattactga a                       101

<210> SEQ ID NO 144
<211> LENGTH: 101
<212> TYPE: DNA
<213> ORGANISM: Homo sapiens

<400> SEQUENCE: 144
taaacccagc gcagataccg aactggtgtc cttcattcca gattgcaaca maacccaaa    60 ctagcaaacg tttaacaggc gcttggcacc cgcaccggtg g                       101

<210> SEQ ID NO 145
<211> LENGTH: 101
<212> TYPE: DNA
<213> ORGANISM: Homo sapiens

<400> SEQUENCE: 145
tctgatgtca cccctctaa ttttgagtga tccagtttct ttgctttta ygcttgtatc     60 tattcttcca tcgtagactg acctggtcat ttctttggag t                       101

<210> SEQ ID NO 146
<211> LENGTH: 101
<212> TYPE: DNA
<213> ORGANISM: Homo sapiens

<400> SEQUENCE: 146
aagctgcccc tcctccaggc ccccagtgat gctaagaatt cacaccatct sctatccaga    60
accagtaact gcctgggagg ttcctgatgg gaatattctg c                       101

<210> SEQ ID NO 147
<211> LENGTH: 101
<212> TYPE: DNA
<213> ORGANISM: Homo sapiens

<400> SEQUENCE: 147
tcacttttgt gattttgtga tgtgtcagtg ctgggactga atccaagttg rgtgacagct    60
ggggcgatgc agcagaaggc aggtcttgct ttttggtaac a                       101

<210> SEQ ID NO 148
<211> LENGTH: 101
<212> TYPE: DNA
<213> ORGANISM: Homo sapiens

<400> SEQUENCE: 148
aggccactgt atcgcttcgt gtccccgtgg aactcataag cagattttgc rctctattaa    60
tctacatctg tttgcacgtc cctgctgtca gcagcttctg t                       101

<210> SEQ ID NO 149
<211> LENGTH: 101
<212> TYPE: DNA
<213> ORGANISM: Homo sapiens

<400> SEQUENCE: 149
ctgaggtcaa gttttttca tatacctcaa ccaaagcaac atactgcaac wgactcaatg     60
cagaggcaga taggagaatg caactatttg attctaagcc a                       101

<210> SEQ ID NO 150
<211> LENGTH: 101
<212> TYPE: DNA
<213> ORGANISM: Homo sapiens

<400> SEQUENCE: 150
actctcttat ttgtcattgg ggacggtgtg gtatcaacag gtttcacaag ktaggggat     60 atgcaccagg gctggaaccc ctctgccttg acggcaccag g                       101

<210> SEQ ID NO 151
<211> LENGTH: 101
<212> TYPE: DNA
<213> ORGANISM: Homo sapiens

<400> SEQUENCE: 151
attttccctc ctgctgaact gagctacttc tgtgagcatt gaaatacttg maggaacctt    60
tgctgctttt ctagtcccag gatttgtgag ctcactgtct g                       101

<210> SEQ ID NO 152
<211> LENGTH: 101
<212> TYPE: DNA
<213> ORGANISM: Homo sapiens

<400> SEQUENCE: 152
ctgtttcttc tggcaaaaaa ggttcatcag agtttacaaa ctccgtgtcc ygagcttcat    60
cagggtcatc ccacacatcc ccattccaag ttgcagggtc c                       101

<210> SEQ ID NO 153
<211> LENGTH: 101
<212> TYPE: DNA
<213> ORGANISM: Homo sapiens

<400> SEQUENCE: 153
cacttcctca tcctaaaatt tggctgctaa tttctgctga tgctcatgga raatttccca    60
aagaccctgc tcctgaatga attgaaagcc tttgagttga g                       101

<210> SEQ ID NO 154
<211> LENGTH: 101
<212> TYPE: DNA
<213> ORGANISM: Homo sapiens

<400> SEQUENCE: 154
tggattctgt atgtgcgtgt gtgtgcacgt gtgttctgca tgcatctcca yggcacatta    60
tctggaggta acatgatcat caggccttga gctcttttat a                       101

<210> SEQ ID NO 155
<211> LENGTH: 101
<212> TYPE: DNA
<213> ORGANISM: Homo sapiens

<400> SEQUENCE: 155
aaatccttaa ggaatagaga aggcttgaaa tgaagtaggt gcttactaaa ygtttgtcaa    60
ataaaataaa tgagtggatt tatgatgcta tgcatgaatt t                       101

<210> SEQ ID NO 156
<211> LENGTH: 101
<212> TYPE: DNA
<213> ORGANISM: Homo sapiens

<400> SEQUENCE: 156
agctttgttc aatgtatttt aatatttatt ttaatttgct tgcattatct ytctttctat    60
taatattcat tatttttctt taccttcttt tataatgttg g                       101

<210> SEQ ID NO 157
<211> LENGTH: 101
<212> TYPE: DNA
<213> ORGANISM: Homo sapiens

<400> SEQUENCE: 157
attgtctgat gcatcgtgac taagcttgga atgtgccaac tgtcccccag sagtggccct    60
tggacagcag agctggagcg ccgggactct gagtgcagga a                       101

<210> SEQ ID NO 158
<211> LENGTH: 101
<212> TYPE: DNA
<213> ORGANISM: Homo sapiens

<400> SEQUENCE: 158
ttcagaactt tacagacgtg tcataagtgg ctcaggagag aggcccactg sacagtggct    60
gcacatggaa ggcagagctg accttgaaga gatgaaggaa a                       101

```
<210> SEQ ID NO 159
<211> LENGTH: 101
<212> TYPE: DNA
<213> ORGANISM: Homo sapiens

<400> SEQUENCE: 159
ctgaagttga tgctgaaaat caacaagaat atgcaacaaa acccatcaaa yactactgaa      60
atagtaaagg ccagggtcca gcacagtggg tcacacctat a                        101

<210> SEQ ID NO 160
<211> LENGTH: 101
<212> TYPE: DNA
<213> ORGANISM: Homo sapiens

<400> SEQUENCE: 160
ttgcaatata atgggtatta tatgaaatta tcttgggttt gtgcttacat ygcaggagtg      60
gcaacaaaac accataatct tttcaatgct tattgcagct g                        101

<210> SEQ ID NO 161
<211> LENGTH: 101
<212> TYPE: DNA
<213> ORGANISM: Homo sapiens

<400> SEQUENCE: 161
gaatataatg ttaaacaaca agctcaaaca acaaacaaca aacttcctgt ytgcataact      60
tgtattctag tggagaacgt cgaaaataaa taaataaata a                        101

<210> SEQ ID NO 162
<211> LENGTH: 101
<212> TYPE: DNA
<213> ORGANISM: Homo sapiens

<400> SEQUENCE: 162
tgttgatgta ccctttaggg tgggggaaag gtttggagaa ctctctggtg ygaagagcat      60
gcttgaggta accacaagtg gtgaacaaag tgcccccaag a                        101

<210> SEQ ID NO 163
<211> LENGTH: 101
<212> TYPE: DNA
<213> ORGANISM: Homo sapiens

<400> SEQUENCE: 163
agagcatagt cctccatgac tttcaatgaa aaacccgata gctttcatct yctcaatcct      60
gaagagctga aggagattta ggctgaactt aaagaaattt t                        101

<210> SEQ ID NO 164
<211> LENGTH: 101
<212> TYPE: DNA
<213> ORGANISM: Homo sapiens

<400> SEQUENCE: 164
cttcatttgg aataaatctt tgatctggaa ccatttccat atttaaaggc yacttcgaat      60
gccatctctg tcatggactt tcctctctcc tttaagcaca a                        101

<210> SEQ ID NO 165
<211> LENGTH: 101
<212> TYPE: DNA
<213> ORGANISM: Homo sapiens

<400> SEQUENCE: 165
```

```
cgtgtttcta aaaatatacg taataacttg tataatgatg ataaagctct rtattacaat    60
tgaataagac aggaaaacta tttcaagtta tttgctgtgt g                      101
```

<210> SEQ ID NO 166
<211> LENGTH: 101
<212> TYPE: DNA
<213> ORGANISM: Homo sapiens
<400> SEQUENCE: 166

```
ctaaagaaag aagcaaaacc aggcacagct gatgggttaa ccagatatga yacagaaaac    60
atttccttct gcttttggt tttaagccta tatttgaagc c                       101
```

<210> SEQ ID NO 167
<211> LENGTH: 101
<212> TYPE: DNA
<213> ORGANISM: Homo sapiens
<400> SEQUENCE: 167

```
ctgacattaa tatgaataga gcagattcct ttgagttaat atttgtctgg kgtgttttat    60
ttcatccact gacttctaac ttttctgtgt tcttagagct g                      101
```

<210> SEQ ID NO 168
<211> LENGTH: 101
<212> TYPE: DNA
<213> ORGANISM: Homo sapiens
<400> SEQUENCE: 168

```
gtttgtaaag gacctgctct tacatttaaa gaaacttttt cgcgagggac rgttcaactg    60
aaacttcgaa agcatcatta tttgcagaga caggacctga c                      101
```

<210> SEQ ID NO 169
<211> LENGTH: 101
<212> TYPE: DNA
<213> ORGANISM: Homo sapiens
<400> SEQUENCE: 169

```
tggaaaattc tttagaatag atcatatgtt aaatcacaaa acaaaccttta rcaaatttga    60 aaaaaatgga acatatcaa gtattttta ataccacaat g                        101
```

<210> SEQ ID NO 170
<211> LENGTH: 101
<212> TYPE: DNA
<213> ORGANISM: Homo sapiens
<400> SEQUENCE: 170

```
ctaactaact aaataaatga taaataaagg cggtgcatga gcactggtga mgggcacttt    60
ggctgcattg agcacttgca aatttgaggt gattaaattc t                      101
```

<210> SEQ ID NO 171
<211> LENGTH: 101
<212> TYPE: DNA
<213> ORGANISM: Homo sapiens
<400> SEQUENCE: 171

```
tcctaggtac atacacgttc acacagctat acacgaagaa tctcagccct ygtacttttg    60
catagtctca tacacgtatc agaagcctcc acctggctaa c                      101
```

<210> SEQ ID NO 172
<211> LENGTH: 101

```
<212> TYPE: DNA
<213> ORGANISM: Homo sapiens

<400> SEQUENCE: 172
caaacctcca tattcatgtc attgaatgtg ggctagtttc agaagggaat ktgaaattgg    60
acaaggcagc tctctttagc agaagcaatt ctccaacagg g                       101

<210> SEQ ID NO 173
<211> LENGTH: 101
<212> TYPE: DNA
<213> ORGANISM: Homo sapiens

<400> SEQUENCE: 173
gggcttattc caacttggcc gtcacagaaa gatcctcttc agctttgttg ytgaaggatg    60
tttttctgat tttagaattc taggtttgtg ttaggtgtag a                       101

<210> SEQ ID NO 174
<211> LENGTH: 101
<212> TYPE: DNA
<213> ORGANISM: Homo sapiens

<400> SEQUENCE: 174
atgtaaaaat acacacacac aaagtggagc tgagggcagg atggagaact stcattctca    60
gcccatgacc tccatggact tggagaaaga ctcagcctgg a                       101

<210> SEQ ID NO 175
<211> LENGTH: 101
<212> TYPE: DNA
<213> ORGANISM: Homo sapiens

<400> SEQUENCE: 175
caacctacag gccacttgtg tcagaatcac gtgaggtaca ttttaaactg yagatttctg    60
tgcccctcac cagactacag agttggaatc tctgagaggt g                       101

<210> SEQ ID NO 176
<211> LENGTH: 101
<212> TYPE: DNA
<213> ORGANISM: Homo sapiens

<400> SEQUENCE: 176
gaatctggct gagcttgggt ggcacccaag gatgcctgca gcccgcccag yggcacggga    60
agccccctca cccgctggct ggaaggggtg ggaggcaagt g                       101

<210> SEQ ID NO 177
<211> LENGTH: 101
<212> TYPE: DNA
<213> ORGANISM: Homo sapiens

<400> SEQUENCE: 177
tctccctcct cccatctccc tcctcctctc catctccctc ttctctcatc yctgtctcct    60
tcctcctcct gtatcttctc cctcctccca tttccctcct c                       101

<210> SEQ ID NO 178
<211> LENGTH: 101
<212> TYPE: DNA
<213> ORGANISM: Homo sapiens

<400> SEQUENCE: 178
acacatgcag gtttgttaca taggtaaact cgtgtcatgg gggttcagtg yacaggttat    60
```
ttcatcacct agctactaaa tgtagtacct gatagttatt t                101

<210> SEQ ID NO 179
<211> LENGTH: 101
<212> TYPE: DNA
<213> ORGANISM: Homo sapiens

<400> SEQUENCE: 179
tccagtgcct gctgacaaga acgaaggccc gggcgattat tctcaataga ytggctttct   60
tctgctgttg ctgctgttgt gtgtacatag attttgtccc c                     101

<210> SEQ ID NO 180
<211> LENGTH: 101
<212> TYPE: DNA
<213> ORGANISM: Homo sapiens

<400> SEQUENCE: 180
atcaaagaag tggctgcttc atcacattca caggccttgt ccacagccaa raggaagaga   60
tcagaggttc tgttcaccgg cggggtagga ctcttggaat t                     101

<210> SEQ ID NO 181
<211> LENGTH: 101
<212> TYPE: DNA
<213> ORGANISM: Homo sapiens

<400> SEQUENCE: 181
aaggaaaagt tcaatataga gattatcatt gcctgggaga catttgcttc rccttctgtt   60
ttcaaatgct tgcaacatag aagactggag tgaatccaag a                     101

<210> SEQ ID NO 182
<211> LENGTH: 101
<212> TYPE: DNA
<213> ORGANISM: Homo sapiens

<400> SEQUENCE: 182
aaagtcaccc tttgcttcat cccttctccc tttattgtgc acctattata dgttatacaa   60
tgtgtttgag cagatgcaaa aaataagact aatttactaa c                     101

<210> SEQ ID NO 183
<211> LENGTH: 101
<212> TYPE: DNA
<213> ORGANISM: Homo sapiens

<400> SEQUENCE: 183
atccctggac aagatcgtaa gtaaaaataa catttcatcc taggaggcac rgagagatta   60
gagccaccct taaggataca atggatatgg agctggtggt c                     101

<210> SEQ ID NO 184
<211> LENGTH: 101
<212> TYPE: DNA
<213> ORGANISM: Homo sapiens

<400> SEQUENCE: 184
ttccatgttt cataagttct taagtgattc ttctttaatc ccactaaatc rtgactccag   60
atgagtttaa gaaatcttaa gactattttt taattattac a                     101

<210> SEQ ID NO 185
<211> LENGTH: 101
<212> TYPE: DNA
<213> ORGANISM: Homo sapiens

<400> SEQUENCE: 185
taagagggaa agctagcaat cccacaatga tttcctttat ttcttgccat mcgaatatat    60
ccttcttcac caaagttgtg gccccagctt tagaaaaga a                         101

<210> SEQ ID NO 186
<211> LENGTH: 101
<212> TYPE: DNA
<213> ORGANISM: Homo sapiens

<400> SEQUENCE: 186
cctgatacga cctgtccttc tcaaaacacc taaacttggg agaacattgt yccccagtgc    60
tggggtagga gagtctgcct gttattctgc ctctatgcag a                       101

<210> SEQ ID NO 187
<211> LENGTH: 100
<212> TYPE: DNA
<213> ORGANISM: Homo sapiens

<400> SEQUENCE: 187
agttctcaca gggcatgggc taacaattat ggtactgctc tacatgtacw ctggaagggg    60
acaagcaagt aaatggatgg tggatggtgg gacccagatt                         100

<210> SEQ ID NO 188
<211> LENGTH: 101
<212> TYPE: DNA
<213> ORGANISM: Homo sapiens

<400> SEQUENCE: 188
aattatgtac caatattggt tcattggtta tgaccaatgc acctcactta yataggatag    60
aaataatagg ggagattggg tgtgaagtat atgggaattc t                       101

<210> SEQ ID NO 189
<211> LENGTH: 101
<212> TYPE: DNA
<213> ORGANISM: Homo sapiens

<400> SEQUENCE: 189
gggagttgta gttttattac ataaaattgc cagccgagga tagggaaaac rgtatttact    60
agcctcgggg aacctcggaa tctgcatctc agccttctcc a                       101

<210> SEQ ID NO 190
<211> LENGTH: 101
<212> TYPE: DNA
<213> ORGANISM: Homo sapiens

<400> SEQUENCE: 190
gctttacatt cctccatgac actaatcacc atctgatgta ctgttttcct satctgttta    60
ttgtcatttt tccccactag acttcaagtt ccatgaaaga g                       101

<210> SEQ ID NO 191
<211> LENGTH: 101
<212> TYPE: DNA
<213> ORGANISM: Homo sapiens

<400> SEQUENCE: 191
caacatgtca tgtgcaatga aaccagataa cagaagaaag ggaaactctc rttttttgtt    60
tagatgttat taatgtgtca cacatttata cacatggcac t                       101

<210> SEQ ID NO 192
<211> LENGTH: 101
<212> TYPE: DNA
<213> ORGANISM: Homo sapiens

<400> SEQUENCE: 192
gctgggatta cgggcatgag ccactgtgcc aggcctcttt tttacacaga rttgttttttg    60 tggaaatacg attgtcaggt taacaatgac tactgttatt c    101

<210> SEQ ID NO 193
<211> LENGTH: 101
<212> TYPE: DNA
<213> ORGANISM: Homo sapiens

<400> SEQUENCE: 193
acattgcatt tgcctccaaa gctcaaaaac agaatgaagc atcacatcaa ygtcagcttc    60 tcttttaaa gaaaattttt ctctcaaaag tgtcccaata t    101

<210> SEQ ID NO 194
<211> LENGTH: 101
<212> TYPE: DNA
<213> ORGANISM: Homo sapiens

<400> SEQUENCE: 194
agatggcagt tgcagtgagc tataatcaag caactgcact gcaatccagc ytgggctggt    60
gagggagact ctgtaaaaaa aaaaaatcag ctcctcagtg g    101

<210> SEQ ID NO 195
<211> LENGTH: 101
<212> TYPE: DNA
<213> ORGANISM: Homo sapiens

<400> SEQUENCE: 195
tatgactacc ctgtgtgatt caataaattt tccaggactc tggtatgaca yactgtttgc    60
attcgactgt ttcctttccc tcttaagcat ttggcccca g    101

<210> SEQ ID NO 196
<211> LENGTH: 101
<212> TYPE: DNA
<213> ORGANISM: Homo sapiens

<400> SEQUENCE: 196
aactagattg aaccctcagc ctagcaatgt cactatgcta cacttttcct rgtgtggtct    60
acccgagatg aggggctgag gtttttttttt gttttttgttt c    101

<210> SEQ ID NO 197
<211> LENGTH: 101
<212> TYPE: DNA
<213> ORGANISM: Homo sapiens

<400> SEQUENCE: 197
tagaaaccag ctccttggac agctcaccaa aaggctagga tgttgaagac rtgctccact    60
cctctcattt cctcctgagg ctgaatcctc gggttgcgta c    101

<210> SEQ ID NO 198
<211> LENGTH: 101
<212> TYPE: DNA
<213> ORGANISM: Homo sapiens

<400> SEQUENCE: 198

```
aacaactatt tcccagtttt tgtaaaattg ttcatttctt agctcctcct yagcctttat    60
ttaatccata cactcttaaa tctttgcttg gatcaataag a                       101

<210> SEQ ID NO 199
<211> LENGTH: 101
<212> TYPE: DNA
<213> ORGANISM: Homo sapiens

<400> SEQUENCE: 199
gtctcttttc tggtgattaa aagtcattat cacctagtca ttactaccaa ygagataatt    60
aagacatttc aaacaaacaa tttaaaacaa gatgtattcc t                       101

<210> SEQ ID NO 200
<211> LENGTH: 101
<212> TYPE: DNA
<213> ORGANISM: Homo sapiens

<400> SEQUENCE: 200
acagatgtgc atgcagacat gagcacacgc acaccagaac actagagtcg rccgcatcct    60
cctcacttgg ctgatgcccc cttctgcttg atttcatcac a                       101

<210> SEQ ID NO 201
<211> LENGTH: 101
<212> TYPE: DNA
<213> ORGANISM: Homo sapiens

<400> SEQUENCE: 201
cattcctttt tttcacctaa atagcattct ctgtcttggc caagctgacc ygtccctgtc    60
ttccacatgc atcttgcact ttttgatgtc ctgttattca c                       101

<210> SEQ ID NO 202
<211> LENGTH: 101
<212> TYPE: DNA
<213> ORGANISM: Homo sapiens

<400> SEQUENCE: 202
aatgtctttt cacatatttg aaattacctg aacctatcac caaggtcata ygcatcatcc    60
atgtatgact ttgccccact tgccaaatgg ggcagaccaa g                       101

<210> SEQ ID NO 203
<211> LENGTH: 101
<212> TYPE: DNA
<213> ORGANISM: Homo sapiens

<400> SEQUENCE: 203
agttttcttt cttttctttt cttttctttt ttttgtttgt tgtcatgtc rttccctggt    60 tttggtactg gctttataga atgatggtga tactggcttt a                       101

<210> SEQ ID NO 204
<211> LENGTH: 101
<212> TYPE: DNA
<213> ORGANISM: Homo sapiens

<400> SEQUENCE: 204
gtgtcccagg cactgtgtta ggattcactg agttgtcaca aaaatcctgc raagttcatt    60
ctcgaggacg ctctggaatt taaataccct gccaagatca t                       101

<210> SEQ ID NO 205
```

```
<211> LENGTH: 101
<212> TYPE: DNA
<213> ORGANISM: Homo sapiens

<400> SEQUENCE: 205
aagcgattct cctgccttag cctttctagt agctgggatt acaggcatgc rccaccatgc    60
ccagctaatt ttttattttt agtagagacg gggtttctcc a                       101

<210> SEQ ID NO 206
<211> LENGTH: 101
<212> TYPE: DNA
<213> ORGANISM: Homo sapiens

<400> SEQUENCE: 206
cagctcattc atgaacaatg actgagtata tgtgatccaa atgcacaggg kgttatcctg    60
agaaagcaat cagccttgtg ggccagataa atccattata a                       101

<210> SEQ ID NO 207
<211> LENGTH: 101
<212> TYPE: DNA
<213> ORGANISM: Homo sapiens

<400> SEQUENCE: 207
attctccagg gatttgctac catctttatt gtctgaaaaa gaatttgata bgtcatattc    60
tctattctgt tcatatttta atatctgaag cctatgctca t                       101

<210> SEQ ID NO 208
<211> LENGTH: 101
<212> TYPE: DNA
<213> ORGANISM: Homo sapiens

<400> SEQUENCE: 208
aactggaact aggttaagca aagtaacatt tcaaaaggga agattcagtg kaagttttct    60
gggattgctc acagaatcca agaatgggct gcaggtatca g                       101

<210> SEQ ID NO 209
<211> LENGTH: 101
<212> TYPE: DNA
<213> ORGANISM: Homo sapiens

<400> SEQUENCE: 209
tatcccatcc ctgtattatc agtatacgtt ggacatatat gaggcaaata ycttttttcat   60 attgagaggt cttcatattg agagaaattg tataagacaa c                       101

<210> SEQ ID NO 210
<211> LENGTH: 101
<212> TYPE: DNA
<213> ORGANISM: Homo sapiens

<400> SEQUENCE: 210
gaacagttaa agatgactta cttttttttt ttttttcattt ataaaaatgc yatggaccct   60
tttaagagaa tcggcatcat gaaatgagag agaaagtagg a                       101

<210> SEQ ID NO 211
<211> LENGTH: 101
<212> TYPE: DNA
<213> ORGANISM: Homo sapiens

<400> SEQUENCE: 211
cagcagtttt ggagatggaa gcaatgccag agatgggact atttcttctt mttgttttag    60
```

```
atgtaaacat taaaaaaaaa aaaacaggat gcacacttag t                    101
```

<210> SEQ ID NO 212
<211> LENGTH: 101
<212> TYPE: DNA
<213> ORGANISM: Homo sapiens

<400> SEQUENCE: 212

```
gccaaagatc ctgaatacca agccctcaga aaatggtaaa gcactgtaag yatcttaatt   60
gtcagcatta tcacaactac aaatggcaaa gctgggtgga g                     101
```

<210> SEQ ID NO 213
<211> LENGTH: 101
<212> TYPE: DNA
<213> ORGANISM: Homo sapiens

<400> SEQUENCE: 213

```
ttttataatt taggaatttc cacattatta agtcaggata gccagtatag yagagataca   60
ggtgtccaat atcccttca tccttcttcc tttagtaata g                      101
```

<210> SEQ ID NO 214
<211> LENGTH: 101
<212> TYPE: DNA
<213> ORGANISM: Homo sapiens

<400> SEQUENCE: 214

```
gggaaaaaat taattgttgt taagaattat ggtgattctg ctccatagca rcttcattaa   60
aggacctagt ctaagttcaa gattaaaagg ttatatgagg c                     101
```

<210> SEQ ID NO 215
<211> LENGTH: 101
<212> TYPE: DNA
<213> ORGANISM: Homo sapiens

<400> SEQUENCE: 215

```
ttaaatataa gcccataggc actctgctgc atgcagattc tatctcaaaa yaaaacactc   60
tgaagatgtt ccaagaccca cacatacaga ttcttttcct t                     101
```

<210> SEQ ID NO 216
<211> LENGTH: 101
<212> TYPE: DNA
<213> ORGANISM: Homo sapiens

<400> SEQUENCE: 216

```
tgaccttctg aacacgattg atgacagcac aggtgatgca actctgacat ytgtggtggc   60
cccagctgct tttgtacctg cgaggagggc aggctgtgca g                     101
```

<210> SEQ ID NO 217
<211> LENGTH: 101
<212> TYPE: DNA
<213> ORGANISM: Homo sapiens

<400> SEQUENCE: 217

```
tgagccagtc tcttctcttt aagttgatgc tagctgccgt tttgtgttat ytgttacaga   60
ctaatacaat ttgcaataat tgaagatgca atatttattg a                     101
```

<210> SEQ ID NO 218
<211> LENGTH: 101
<212> TYPE: DNA

-continued

```
<213> ORGANISM: Homo sapiens

<400> SEQUENCE: 218
tgcctcctcc tcctcctcct cgttaaactg gttaattaat ggctgctgcc ygtgggaagc        60
agatgttctg gagctgttgg cctggggagg cattggtctg g                          101
```

ANCESTRY-SPECIFIC GENETIC RISK SCORES

CROSS-REFERENCE

This application claims priority to U.S. Provisional Application No. 62/772,565, filed Nov. 28, 2018, which application is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 11, 2018, is named 55075_701_201_SL.txt and is 49,097 bytes in size.

SUMMARY OF THE INVENTION

Genome Wide Association Studies (GWAS) have enabled scientists to identify genetic variations that are associated with a wide range of phenotypic traits. A genetic risk score (GRS) is used to predict whether an individual will develop a trait based on a presence of certain genetic variants detected in a sample obtained from that individual. However, data show that genetic variation and patterns underlying discrete ancestral populations differ. Thus, whether the detected genetic variants confer a risk that the individual will develop the trait depends in large part on the ancestry of that individual. Current genetic risk prediction methods either do not account for the ancestry of the individual at all, or account for ancestry using consumer surveys leading to imprecise, and often, inaccurate genetic risk predictions.

Disclosed herein, in certain embodiments, are methods, media, and systems for calculating a GRS by analyzing the genotype of the individual to determine an ancestry of the individual and calculating a GRS based on the ancestry-specific genetic risk variants derived from GWAS of subjects of the same ancestry as the individual. In some embodiments, genetic variant(s) accounted for in a GRS may include single nucleotide variants (SNVs), insertions or deletions of nucleotide bases (indels), or copy number variants (CNVs). In some embodiments, if a genetic variant detected in a sample obtained from the individual does not correspond to genetic variant reported in the GWAS of the ancestry-specific subject group (unknown genetic variant), a proxy genetic variant is selected based on the non-random association, known as linkage disequilibrium (LD), with the unknown genetic variant within the particular ancestral population, which serves as the basis for risk prediction. Studies show that patterns in LD in the human genome differ across different ancestral populations.

Disclosed herein, in certain embodiments, are computer-implemented methods for recommending a behavioral modification to an individual based on an ancestry and a genotype of the individual, the method comprising: a) providing the genotype of the individual, the genotype comprising one or more individual-specific genetic variants; b) assigning an ancestry to the individual based, at least in part, on the genotype of the individual; c) using a trait-associated variants database comprising ancestry-specific genetic variants derived from subjects with the same ancestry as the individual (subject group) to select one or more ancestry-specific genetic variants based, at least in part, on the ancestry of the individual, wherein each of the one or more ancestry-specific genetic variants correspond to: (i) an individual-specific genetic variant of the one or more individual-specific genetic variants, or (ii) a predetermined genetic variant in linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk; (d) calculating a genetic risk score for the individual based on the selected one or more ancestry-specific genetic variants, wherein the genetic risk score is indicative of the likelihood that the individual has, or will develop the specific trait; and (e) providing a recommendation to the individual comprising a behavioral modification related to the specific trait based on the genetic risk score. In some embodiments, the methods further comprise providing a survey to the individual comprising one or more questions relating to the specific trait. In some embodiments, the methods further comprise receiving, from the individual, one or more answers to one or more questions relating to the specific trait in a survey provided to the individual. In some embodiments, the methods further comprise: a) providing a survey to the individual comprising one or more questions relating to the specific trait; and b) receiving, from the individual, one or more answers to the one or more questions, wherein the recommendation to the individual comprising the behavioral modification related to the specific trait is further based on the one or more answers provided by the individual. In some embodiments, the methods further comprise storing, in a trait-associated variants database, the ancestry-specific genetic variants associated with the specific trait derived from the subject group. In some embodiments, the genetic risk score comprises a percentile or z-score. In some embodiments, the LD is defined by (i) D' value of at least about 0.20, or (ii) an $r^2$ value of at least about 0.70. In some embodiments, the LD is defined by a D' value comprising between about 0.20 and 0.25, 0.25 and 0.30, 0.30 and 0.35, 0.35 and 0.40, 0.40 and 0.45, 0.45 and 0.50, 0.50 and 0.55, 0.55 and 0.60, 0.60 and 0.65, 0.65 and 0.70, 0.70 and 0.75, 0.75 and 0.80, 0.80 and 0.85, 0.85 and 0.90, 0.90 and 0.95, or 0.95 and 1.0. In some embodiments, the LD is defined by a D' value comprising at least about 0.20, 0.25, 0.30, 0.35, 0.40, 0.45, 0.50, 0.55, 0.60, 0.65, 0.70, 0.75, 0.80, 0.85, 0.85, 0.90, 0.95 and 1.0. In some embodiments, the LD is defined by a $r^2$ value comprising at least about 0.70, 0.75, 0.80, 0.85, 0.90, 0.95 and 1.0. In some embodiments, the LD is defined by a $r^2$ value comprising between about 0.70 and 0.75, 0.75 and 0.80, 0.80 and 0.85, 0.85 and 0.90, 0.90 and 0.95, or 0.95 and 1.0. In some embodiments, the genotype of the individual is obtained by subjecting, or having subjected, genetic material obtained from the individual to a genotyping assay. In some embodiments, genotype of the individual is obtained by subjecting the genetic material obtained from the individual to a deoxyribonucleic acid (DNA) array, ribonucleic acid (RNA) array, sequencing assay, or a combination thereof. In some embodiments, the sequencing assay comprises next generation sequencing (NGS). In some embodiments, the methods further comprise updating the trait-associated variants database with the assigned ancestry, a specific trait, and the genotype of the individual. In some embodiments, ancestry is assigned to the individual in (b) using a principle component analysis (PCA), or a maximum likelihood estimation (MLE), or a combination thereof. In some embodiments, the one or more ancestry-specific genetic variants, the one or more individual-specific genetic variants, and the genetic variants in LD with the one or more individual-specific genetic variants comprise a Single Nucleotide Variant (SNV). In some embodiments, the one or more units of risk comprises a risk allele. In some embodiments, the one or more ancestry-specific genetic variants, the one or more individual-specific genetic variants, and the genetic variants in LD with the one or more individual-specific genetic variants comprise an indel characterized by an insertion or a deletion of one or more nucleotides. In some embodiments, the one or more units of risk comprises an insertion (I) or deletion (D) of a nucleotide base. In some embodiments, the one or more ancestry-specific genetic variants, or the one or more individual-specific genetic variants comprise a Copy Number Variant (CNV). In some embodiments, the one or more units of risk comprises a duplication or a deletion of a nucleic acid sequence. In some embodiments, the nucleic acid sequence comprises about two, three, four, five, six, seven, eight, nine, or ten, nucleotides. In some embodiments, the nucleic acid sequence comprises more than three nucleotides. In some embodiments, the nucleic acid sequence comprises an entire gene. In some embodiments, the methods further comprise providing a notification to the individual of the risk that the individual has, or will develop, the specific trait. In some embodiments, the specific trait comprises a nutritional trait, a clinical trait, a subclinical trait, a physical exercise trait, a skin trait, a hair trait, an allergy trait, or a mental trait. In some embodiments, the clinical trait comprises a disease or condition. In some embodiments, the subclinical trait comprises a phenotype of a disease or condition. In some embodiments, the physical exercise trait comprises exercise aversion, aerobic performance, difficulty losing weight, endurance, power, fitness benefits, reduced heart beat response to exercise, lean body mass, muscle soreness, muscle damage risk, muscle repair impairment, stress fracture, overall injury risk, potential for obesity, or resting metabolic rate impairment. In some embodiments, the skin trait comprises collagen breakdown, dryness, antioxidant deficiency, detoxification impairment, skin glycation, pigmented spots, youthfulness, photoaging, dermal sensitivity, or sensitivity to sun. In some embodiments, the hair trait comprises hair thickness, hair thinning, hair loss, baldness, oiliness, dryness, dandruff, or hair volume. In some embodiments, the nutritional trait comprises vitamin deficiency, mineral deficiency, antioxidant deficiency, fatty acid deficiency, metabolic imbalance, metabolic impairment, metabolic sensitivity, allergy, satiety, or the effectiveness of a healthy diet. In some embodiments, the vitamin deficiency comprises a deficiency of a vitamin comprising Vitamin A, Vitamin B1, Vitamin B2, Vitamin B3, Vitamin B5, Vitamin B6, Vitamin B7, Vitamin B8, Vitamin B9, Vitamin B12, Vitamin C, Vitamin D, Vitamin E, and Vitamin K. In some embodiments, the mineral deficiency comprises a deficiency of a mineral comprising calcium, iron, magnesium, zinc, or selenium. In some embodiments, the antioxidant deficiency comprises a deficiency of an antioxidant comprising glutathione, or coenzyme Q10 (CoQ10). In some embodiments, the fatty acid deficiency comprises a deficiency in polyunsaturated fatty acids or monounsaturated fatty acids. In some embodiments, the metabolic imbalance comprises glucose imbalance. In some embodiments, the metabolic impairment comprises impaired metabolism of caffeine or drug therapy. In some embodiments, the metabolic sensitivity comprises gluten sensitivity, glycan sensitivity, or lactose sensitivity. In some embodiments, the allergy comprises an allergy to food (food allergy) or environmental factors (environmental allergy). In some embodiments, the methods further comprise administering a treatment to the individual effective to ameliorate or prevent the specific trait in the individual, provided the genetic risk score indicates a high likelihood that the individual has, or will develop, the specific trait. In some embodiments, the treatment comprises a supplement or drug therapy. In some embodiments, the supplement comprises a vitamin, mineral, probiotic, anti-oxidant, anti-inflammatory, or combination thereof. In some embodiments, the behavioral modification related to the specific trait comprises increasing, reducing, or avoiding an activity comprising performance of a physical exercise, ingestion of a drug, vitamin, or supplement, exposure to a product, usage of a product, a diet modification, sleep modification, alcohol consumption, or caffeine consumption. In some embodiments, the recommendation is displayed in a report. In some embodiments, the report is displayed to the individual via a user interface of an electronic device. In some embodiments, the report further comprises the genetic risk score for the individual for the specific trait. In some embodiments, the genetic risk score is calculated by: a) calculating a raw score comprising a total number of the one or more units of risk for each ancestry-specific genetic variant for each subject of the subject group, thereby generating an ancestry-specific observed range of raw scores; b) calculating a total number of the one or more units of risk for each of the one or more individual-specific genetic variants, thereby generating an individual raw score; and c) comparing the individual raw score with the ancestry-specific observed range to generate the genetic risk score. In some embodiments, the genetic risk score is calculated by: a) determining an odds ratio for each of the ancestry-specific genetic risk variants; and b) if two or more ancestry-specific genetic variants are selected, then multiplying the odds ratio for each of the two or more ancestry-specific genetic variants together. In some embodiments, the genetic risk score is calculated by: a) determining a relative risk for each of the ancestry-specific genetic risk variants; and b) if two or more ancestry-specific genetic variants are selected, then multiplying the relative risks for each of the two or more ancestry-specific genetic variants together. In some embodiments, the predetermined genetic variant is determined by a) providing unphased genotype data from an individual; b) phasing the unphased genotype data to generate individual-specific phased haplotypes based on the ancestry of the individual; c) imputing individual-specific genotypes not present in the phased individual-specific phased haplotypes using phased haplotype data from a reference group that has the same ancestry as the individual; and d) selecting a genetic variant from the imputed individual-specific genotypes that is in linkage disequilibrium (LD) an individual-specific genetic variant associated with a likelihood that the individual has, or will develop, a specific trait.

Disclosed herein, in certain embodiments, are computer-implemented methods of determining a likelihood that an individual has, or will develop, a specific trait based on the ancestry of the individual, the method comprising: a) providing the genotype of the individual, the genotype comprising one or more individual-specific genetic variants; b) assigning an ancestry to the individual based, at least in part, on the genotype of the individual; c) using a trait-associated variants database comprising ancestry-specific genetic variants derived from subjects with the same ancestry as the individual (subject group) to select one or more ancestry-specific genetic variants based, at least in part, on the ancestry of the individual, wherein each of the one or more ancestry-specific genetic variants correspond to: (i) an individual-specific genetic variant of the one or more individual-specific genetic variants, or (ii) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk; and (d) calculating a genetic risk score for the individual based on the selected one or more ancestry-specific genetic variants, wherein the genetic risk score is indicative of the likelihood that the individual has, or will develop the specific trait. In some embodiments, the methods further comprise providing a notification to the individual of the risk that the individual has, or will develop, the specific trait. In some embodiments, the notification comprises a recommendation for a behavior modification related to the specific trait. In some embodiments, the behavioral modification related to the specific trait comprises increasing, reducing, or avoiding an activity comprising performance of a physical exercise, ingestion of a drug, vitamin, or supplement, exposure to a product, usage of a product, a diet modification, sleep modification, alcohol consumption, or caffeine consumption. In some embodiments, the notification is displayed in a report. In some embodiments, the report is displayed to the individual via a user interface of an electronic device. In some embodiments, the methods further comprise providing a survey to the individual comprising one or more questions relating to the specific trait. In some embodiments, the methods further comprise receiving, from the individual, one or more answers to one or more questions relating to the specific trait in a survey provided to the individual. In some embodiments, the methods further comprise: a) providing a survey to the individual comprising one or more questions relating to the specific trait; and b) receiving, from the individual, one or more answers to the one or more questions, wherein the recommendation to the individual comprising the behavioral modification related to the specific trait is further based on the one or more answers provided by the individual. In some embodiments, the methods further comprise storing, in a trait-associated variants database, the ancestry-specific genetic variants associated with the specific trait derived from the subject group. In some embodiments, the genetic risk score comprises a percentile or z-score. In some embodiments, the LD is defined by (i) D' value of at least about 0.20, or (ii) an $r^2$ value of at least about 0.70. In some embodiments, the LD is defined by a D' value comprising between about 0.20 and 0.25, 0.25 and 0.30, 0.30 and 0.35, 0.35 and 0.40, 0.40 and 0.45, 0.45 and 0.50, 0.50 and 0.55, 0.55 and 0.60, 0.60 and 0.65, 0.65 and 0.70, 0.70 and 0.75, 0.75 and 0.80, 0.80 and 0.85, 0.85 and 0.90, 0.90 and 0.95, or 0.95 and 1.0. In some embodiments, the LD is defined by a $r^2$ value comprising between about 0.70 and 0.75, 0.75 and 0.80, 0.80 and 0.85, 0.85 and 0.90, 0.90 and 0.95, or 0.95 and 1.0. In some embodiments, the LD is defined by a D' value comprising at least about 0.20, 0.25, 0.30, 0.35, 0.40, 0.45, 0.50, 0.55, 0.60, 0.65, 0.70, 0.75, 0.80, 0.85, 0.85, 0.90, 0.95 and 1.0. In some embodiments, the LD is defined by a $r^2$ value comprising at least about 0.70, 0.75, 0.80, 0.85, 0.90, 0.95 and 1.0. In some embodiments, the genotype of the individual is obtained by subjecting, or having subjected, genetic material obtained from the individual to a genotyping assay. In some embodiments, genotype of the individual is obtained by subjecting the genetic material obtained from the individual to a deoxyribonucleic acid (DNA) array, ribonucleic acid (RNA) array, sequencing assay, or a combination thereof. In some embodiments, the sequencing assay comprises next generation sequencing (NGS). In some embodiments, the methods further comprise updating the trait-associated variants database with the assigned ancestry, a specific trait, and the genotype of the individual. In some embodiments, ancestry is assigned to the individual in (b) using a principle component analysis (PCA), or a maximum likelihood estimation (MLE), or a combination thereof. In some embodiments, the one or more ancestry-specific genetic variants, the one or more individual-specific genetic variants, and the genetic variants in LD with the one or more individual-specific genetic variants comprise a Single Nucleotide Variant (SNV). In some embodiments, the one or more units of risk comprises a risk allele. In some embodiments, the one or more ancestry-specific genetic variants, the one or more individual-specific genetic variants, and the genetic variants in LD with the one or more individual-specific genetic variants comprise an indel characterized by an insertion or a deletion of one or more nucleotides. In some embodiments, the one or more units of risk comprises a insertion (I) or a deletion (D) of one or more nucleotides. In some embodiments, the one or more ancestry-specific genetic variants, or the one or more individual-specific genetic variants comprise a Copy Number Variant (CNV). In some embodiments, the one or more units of risk comprises an insertion or a deletion of a nucleic acid sequence. In some embodiments, the nucleic acid sequence comprises about two, three, four, five, six, seven, eight, nine, or ten, nucleotides. In some embodiments, the nucleic acid sequence comprises more than three nucleotides. In some embodiments, the nucleic acid sequence comprises an entire gene. In some embodiments, the methods further comprise providing a notification to the individual of the risk that the individual has, or will develop, the specific trait. In some embodiments, the specific trait comprises a nutritional trait, a clinical trait, a subclinical trait, a physical exercise trait, a skin trait, a hair trait, an allergy trait, or a mental trait. In some embodiments, the clinical trait comprises a disease or condition. In some embodiments, the subclinical trait comprises a phenotype of a disease or condition. In some embodiments, the physical exercise trait comprises exercise aversion, aerobic performance, difficulty losing weight, endurance, power, fitness benefits, reduced heart beat response to exercise, lean body mass, muscle soreness, muscle damage risk, muscle repair impairment, stress fracture, overall injury risk, potential for obesity, or resting metabolic rate impairment. In some embodiments, the skin trait comprises collagen breakdown, dryness, antioxidant deficiency, detoxification impairment, skin glycation, pigmented spots, youthfulness, photoaging, dermal sensitivity, or sensitivity to sun. In some embodiments, the nutritional trait comprises vitamin deficiency, mineral deficiency, antioxidant deficiency, fatty acid deficiency, metabolic imbalance, metabolic impairment, metabolic sensitivity, allergy, satiety, or the effectiveness of a healthy diet. In some embodiments, the hair trait comprises hair thickness, hair thinning, hair loss, baldness, oiliness, dryness, dandruff, or hair volume. In some embodiments, the vitamin deficiency comprises a deficiency of a vitamin comprising Vitamin A, Vitamin B1, Vitamin B2, Vitamin B3, Vitamin B5, Vitamin B6, Vitamin B7, Vitamin B8, Vitamin B9, Vitamin B12, Vitamin C, Vitamin D, Vitamin E, and Vitamin K. In some embodiments, the mineral deficiency comprises a deficiency of a mineral comprising calcium, iron, magnesium, zinc, or selenium. In some embodiments, the antioxidant deficiency comprises a deficiency of an antioxidant comprising glutathione, or coenzyme Q10 (CoQ10). In some embodiments, the fatty acid deficiency comprises a deficiency in polyunsaturated fatty acids or monounsaturated fatty acids. In some embodiments, the metabolic imbalance comprises glucose imbalance. In some embodiments, the metabolic impairment comprises impaired metabolism of caffeine or drug therapy. In some embodiments, the metabolic sensitivity comprises gluten sensitivity, glycan sensitivity, or lactose sensitivity. In some embodiments, the allergy comprises an allergy to food (food allergy) or environmental factors (environmental allergy). In some embodiments, the methods further comprise administering a treatment to the individual effective to ameliorate or prevent the specific trait in the individual, provided the genetic risk score indicates a high likelihood that the individual has, or will develop, the specific trait. In some embodiments, the treatment comprises a supplement or drug therapy. In some embodiments, the supplement comprises a vitamin, mineral, probiotic, anti-oxidant, anti-inflammatory, or combination thereof. In some embodiments, the genetic risk score is calculated by: a) calculating a raw score comprising a total number of the one or more units of risk for each ancestry-specific genetic variant for each subject of the subject group, thereby generating an ancestry-specific observed range of raw scores; b) calculating a total number of the one or more units of risk for each of the one or more individual-specific genetic variants, thereby generating an individual raw score; and c) comparing the individual raw score with the ancestry-specific observed range to generate the genetic risk score. In some embodiments, the genetic risk score is calculated by: a) determining an odds ratio for each of the ancestry-specific genetic risk variants; and b) if two or more ancestry-specific genetic variants are selected, then multiplying the odds ratio for each of the two or more ancestry-specific genetic variants together. In some embodiments, the genetic risk score is calculated by: a) determining a relative risk for each of the ancestry-specific genetic risk variants; and b) if two or more ancestry-specific genetic variants are selected, then multiplying the relative risks for each of the two or more ancestry-specific genetic variants together. In some embodiments, the predetermined genetic variant is determined by a) providing unphased genotype data from an individual; b) phasing the unphased genotype data to generate individual-specific phased haplotypes based on the ancestry of the individual; c) imputing individual-specific genotypes not present in the phased individual-specific phased haplotypes using phased haplotype data from a reference group that has the same ancestry as the individual; and d) selecting a genetic variant from the imputed individual-specific genotypes that is in linkage disequilibrium (LD) an individual-specific genetic variant associated with a likelihood that the individual has, or will develop, a specific trait.

Disclosed herein, in certain embodiments, are wellness reporting systems comprising: a) a computing device comprising at least one processor, a memory, and a software program including instructions executable by at least one processor to assess a likelihood that an individual has, or will develop, a specific trait, the instructions comprising the steps of: (i) providing the genotype of the individual, the genotype comprising one or more individual-specific genetic variants; (ii) assigning an ancestry to the individual based, at least in part, on the genotype of the individual; (iii) using a trait-associated variants database comprising ancestry-specific genetic variants derived from subjects with the same ancestry as the individual (subject group) to select one or more ancestry-specific genetic variants based, at least in part, on the ancestry of the individual, wherein each of the one or more ancestry-specific genetic variants correspond to: (1) an individual-specific genetic variant of the one or more individual-specific genetic variants, or (2) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk; and (iv) calculating a genetic risk score for the individual based on the selected one or more ancestry-specific genetic variants, wherein the genetic risk score is indicative of the likelihood that the individual has, or will develop the specific trait; b) a reporting module generate a report comprising the genetic risk score of the individual for the specific trait; and c) an output module configured to display the report to the individual. In some embodiments, the genetic risk score comprises a percentile or z-score. In some embodiments, the LD is defined by (i) D' value of at least about 0.20, or (ii) an $r^2$ value of at least about 0.70. In some embodiments, the LD is defined by a D' value comprising between about 0.20 and 0.25, 0.25 and 0.30, 0.30 and 0.35, 0.35 and 0.40, 0.40 and 0.45, 0.45 and 0.50, 0.50 and 0.55, 0.55 and 0.60, 0.60 and 0.65, 0.65 and 0.70, 0.70 and 0.75, 0.75 and 0.80, 0.80 and 0.85, 0.85 and 0.90, 0.90 and 0.95, or 0.95 and 1.0. In some embodiments, the LD is defined by a $r^2$ value comprising between about 0.70 and 0.75, 0.75 and 0.80, 0.80 and 0.85, 0.85 and 0.90, 0.90 and 0.95, or 0.95 and 1.0. In some embodiments, the LD is defined by a D' value comprising at least about 0.20, 0.25, 0.30, 0.35, 0.40, 0.45, 0.50, 0.55, 0.60, 0.65, 0.70, 0.75, 0.80, 0.85, 0.85, 0.90, 0.95 and 1.0. In some embodiments, the LD is defined by a $r^2$ value comprising at least about 0.70, 0.75, 0.80, 0.85, 0.90, 0.95 and 1.0. In some embodiments, the genotype of the individual is obtained by subjecting, or having subjected, genetic material obtained from the individual to a genotyping assay. In some embodiments, genotype of the individual is obtained by subjecting the genetic material obtained from the individual to a deoxyribonucleic acid (DNA) array, ribonucleic acid (RNA) array, sequencing assay, or a combination thereof. In some embodiments, the sequencing assay comprises next generation sequencing (NGS). In some embodiments, the methods further comprise updating the trait-associated variants database with the assigned ancestry, a specific trait, and the genotype of the individual. In some embodiments, ancestry is assigned to the individual in (b) using a principle component analysis (PCA), or a maximum likelihood estimation (MLE), or a combination thereof. In some embodiments, the one or more ancestry-specific genetic variants, the one or more individual-specific genetic variants, and the genetic variants in LD with the one or more individual-specific genetic variants comprise a Single Nucleotide Variant (SNV). In some embodiments, the one or more units of risk comprises a risk allele. In some embodiments, the one or more ancestry-specific genetic variants, the one or more individual-specific genetic variants, and the genetic variants in LD with the one or more individual-specific genetic variants comprise an indel characterized by an insertion or a deletion of one or more nucleotides. In some embodiments, the one or more units of risk comprises a insertion (I) or a deletion (D) of one or more nucleotides. In some embodiments, the one or more ancestry-specific genetic variants, or the one or more individual-specific genetic variants comprise a Copy Number Variant (CNV). In some embodiments, the one or more units of risk comprises an insertion or a deletion of a nucleic acid sequence. In some embodiments, the nucleic acid sequence comprises about two, three, four, five, six, seven, eight, nine, or ten, nucleotides. In some embodiments, the nucleic acid sequence comprises more than three nucleotides. In some embodiments, the nucleic acid sequence comprises an entire gene. In some embodiments, the methods further comprise providing a notification to the individual of the risk that the individual has, or will develop, the specific trait. In some embodiments, the specific trait comprises a nutritional trait, a clinical trait, a subclinical trait, a physical exercise trait, a skin trait, a hair trait, an allergy trait, or a mental trait. In some embodiments, the clinical trait comprises a disease or condition. In some embodiments, the subclinical trait comprises a phenotype of a disease or condition. In some embodiments, the physical exercise trait comprises exercise aversion, aerobic performance, difficulty losing weight, endurance, power, fitness benefits, reduced heart beat response to exercise, lean body mass, muscle soreness, muscle damage risk, muscle repair impairment, stress fracture, overall injury risk, potential for obesity, or resting metabolic rate impairment. In some embodiments, the skin trait comprises collagen breakdown, dryness, antioxidant deficiency, detoxification impairment, skin glycation, pigmented spots, youthfulness, photoaging, dermal sensitivity, or sensitivity to sun. In some embodiments, the hair trait comprises hair thickness, hair thinning, hair loss, baldness, oiliness, dryness, dandruff, or hair volume. In some embodiments, the nutritional trait comprises vitamin deficiency, mineral deficiency, antioxidant deficiency, fatty acid deficiency, metabolic imbalance, metabolic impairment, metabolic sensitivity, allergy, satiety, or the effectiveness of a healthy diet. In some embodiments, the vitamin deficiency comprises a deficiency of a vitamin comprising Vitamin A, Vitamin B1, Vitamin B2, Vitamin B3, Vitamin B5, Vitamin B6, Vitamin B7, Vitamin B8, Vitamin B9, Vitamin B12, Vitamin C, Vitamin D, Vitamin E, and Vitamin K. In some embodiments, the mineral deficiency comprises a deficiency of a mineral comprising calcium, iron, magnesium, zinc, or selenium. In some embodiments, the antioxidant deficiency comprises a deficiency of an antioxidant comprising glutathione, or coenzyme Q10 (CoQ10). In some embodiments, the fatty acid deficiency comprises a deficiency in polyunsaturated fatty acids or monounsaturated fatty acids. In some embodiments, the metabolic imbalance comprises glucose imbalance. In some embodiments, the metabolic impairment comprises impaired metabolism of caffeine or drug therapy. In some embodiments, the metabolic sensitivity comprises gluten sensitivity, glycan sensitivity, or lactose sensitivity. In some embodiments, the allergy comprises an allergy to food (food allergy) or environmental factors (environmental allergy). In some embodiments, the methods further comprise administering a treatment to the individual effective to ameliorate or prevent the specific trait in the individual, provided the genetic risk score indicates a high likelihood that the individual has, or will develop, the specific trait. In some embodiments, the treatment comprises a supplement or drug therapy. In some embodiments, the supplement comprises a vitamin, mineral, probiotic, anti-oxidant, anti-inflammatory, or combination thereof. In some embodiments, the instructions further comprise a survey to the individual comprising one or more questions relating to the specific trait. In some embodiments, the instructions further comprise receiving, from the individual, one or more answers to one or more questions relating to the specific trait in a survey provided to the individual. In some embodiments, the instructions further comprise: (i) providing a survey to the individual comprising one or more questions relating to the specific trait; and (ii) receiving, from the individual, one or more answers to the one or more questions. In some embodiments, the instructions further comprise storing, in a trait-associated variants database, the ancestry-specific genetic variants associated with the specific trait derived from the subject group. In some embodiments, the output module is configured to display the report on a user interface of a personal electronic device. In some embodiments, the system further comprises a personal electronic device with an application configured to communicate with the output module via a computer network to access the report. In some embodiments, the genetic risk score is calculated by: (1) calculating a raw score comprising a total number of the one or more units of risk for each ancestry-specific genetic variant for each subject of the subject group, thereby generating an ancestry-specific observed range of raw scores; (2) calculating a total number of the one or more units of risk for each of the one or more individual-specific genetic variants, thereby generating an individual raw score; and (3) comparing the individual raw score with the ancestry-specific observed range to generate the genetic risk score. In some embodiments, the genetic risk score is calculated by: (1) determining an odds ratio for each of the ancestry-specific genetic risk variants; and (2) if two or more ancestry-specific genetic variants are selected, then multiplying the odds ratio for each of the two or more ancestry-specific genetic variants together. In some embodiments, the system further comprises the steps of determining the predetermined genetic variant by: a) providing unphased genotype data from an individual; b) phasing the unphased genotype data to generate individual-specific phased haplotypes based on the ancestry of the individual; c) imputing individual-specific genotypes not present in the phased individual-specific phased haplotypes using phased haplotype data from a reference group that has the same ancestry as the individual; and d) selecting a genetic variant from the imputed individual-specific genotypes that is in linkage disequilibrium (LD) the individual-specific genetic variant associated with a likelihood that the individual has, or will develop, a specific trait.

Disclosed herein, in certain embodiments, are non-transitory computer readable storage media, comprising computer-executable code configured to cause at least one processor to perform steps of: a) providing the genotype of the individual, the genotype comprising one or more individual-specific genetic variants; b) assigning an ancestry to the individual based, at least in part, on the genotype of the individual; c) using a trait-associated variants database comprising ancestry-specific genetic variants derived from subjects with the same ancestry as the individual (subject group) to select one or more ancestry-specific genetic variants based, at least in part, on the ancestry of the individual, wherein each of the one or more ancestry-specific genetic variants correspond to: (ii) an individual-specific genetic variant of the one or more individual-specific genetic variants, or (ii) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk; and d) calculating a genetic risk score for the individual based on the selected one or more ancestry-specific genetic variants, wherein the genetic risk score is indicative of the likelihood that the individual has, or will develop the specific trait. In some embodiments, the media further comprises providing a survey to the individual comprising one or more questions relating to the specific trait. In some embodiments, the media further comprises receiving, from the individual, one or more answers to one or more questions relating to the specific trait in a survey provided to the individual. In some embodiments, the media further comprises: a) providing a survey to the individual comprising one or more questions relating to the specific trait; and c) receiving, from the individual, one or more answers to the one or more questions. In some embodiments, the media further comprising storing, in a trait-associated variants database, the ancestry-specific genetic variants associated with the specific trait derived from the subject group. In some embodiments, the genetic risk score comprises a percentile or z-score. In some embodiments, the LD is defined by (i) D' value of at least about 0.20, or (ii) an $r^2$ value of at least about 0.70. In some embodiments, the LD is defined by a D' value comprising between about 0.20 and 0.25, 0.25 and 0.30, 0.30 and 0.35, 0.35 and 0.40, 0.40 and 0.45, 0.45 and 0.50, 0.50 and 0.55, 0.55 and 0.60, 0.60 and 0.65, 0.65 and 0.70, 0.70 and 0.75, 0.75 and 0.80, 0.80 and 0.85, 0.85 and 0.90, 0.90 and 0.95, or 0.95 and 1.0. In some embodiments, the LD is defined by a $r^2$ value comprising between about 0.70 and 0.75, 0.75 and 0.80, 0.80 and 0.85, 0.85 and 0.90, 0.90 and 0.95, or 0.95 and 1.0. In some embodiments, the LD is defined by a D' value comprising at least about 0.20, 0.25, 0.30, 0.35, 0.40, 0.45, 0.50, 0.55, 0.60, 0.65, 0.70, 0.75, 0.80, 0.85, 0.85, 0.90, 0.95 and 1.0. In some embodiments, the LD is defined by a $r^2$ value comprising at least about 0.70, 0.75, 0.80, 0.85, 0.90, 0.95 and 1.0. In some embodiments, the genotype of the individual is obtained by subjecting, or having subjected, genetic material obtained from the individual to a genotyping assay. In some embodiments, genotype of the individual is obtained by subjecting the genetic material obtained from the individual to a deoxyribonucleic acid (DNA) array, ribonucleic acid (RNA) array, sequencing assay, or a combination thereof. In some embodiments, the sequencing assay comprises next generation sequencing (NGS). In some embodiments, the methods further comprise updating the trait-associated variants database with the assigned ancestry, a specific trait, and the genotype of the individual. In some embodiments, ancestry is assigned to the individual in (b) using a principle component analysis (PCA), or a maximum likelihood estimation (MLE), or a combination thereof. In some embodiments, the one or more ancestry-specific genetic variants, the one or more individual-specific genetic variants, and the genetic variants in LD with the one or more individual-specific genetic variants comprise a Single Nucleotide Variant (SNV). In some embodiments, the one or more units of risk comprises a risk allele. In some embodiments, the one or more ancestry-specific genetic variants, the one or more individual-specific genetic variants, and the genetic variants in LD with the one or more individual-specific genetic variants comprise an indel characterized by an insertion or a deletion of one or more nucleotides. In some embodiments, the one or more units of risk comprises a insertion (I) or a deletion (D) of one or more nucleotides. In some embodiments, the one or more ancestry-specific genetic variants, or the one or more individual-specific genetic variants comprise a Copy Number Variant (CNV). In some embodiments, the one or more units of risk comprises an insertion or a deletion of a nucleic acid sequence. In some embodiments, the nucleic acid sequence comprises about two, three, four, five, six, seven, eight, nine, or ten, nucleotides. In some embodiments, the nucleic acid sequence comprises more than three nucleotides. In some embodiments, the nucleic acid sequence comprises an entire gene. In some embodiments, the methods further comprise providing a notification to the individual of the risk that the individual has, or will develop, the specific trait. In some embodiments, the specific trait comprises a nutritional trait, a clinical trait, a subclinical trait, a physical exercise trait, a skin trait, a hair trait, an allergy trait, or a mental trait. In some embodiments, the clinical trait comprises a disease or condition. In some embodiments, the subclinical trait comprises a phenotype of a disease or condition. In some embodiments, the physical exercise trait comprises exercise aversion, aerobic performance, difficulty losing weight, endurance, power, fitness benefits, reduced heart beat response to exercise, lean body mass, muscle soreness, muscle damage risk, muscle repair impairment, stress fracture, overall injury risk, potential for obesity, or resting metabolic rate impairment. In some embodiments, the skin trait comprises collagen breakdown, dryness, antioxidant deficiency, detoxification impairment, skin glycation, pigmented spots, youthfulness, photoaging, dermal sensitivity, or sensitivity to sun. In some embodiments, the hair trait comprises hair thickness, hair thinning, hair loss, baldness, oiliness, dryness, dandruff, or hair volume. In some embodiments, the nutritional trait comprises vitamin deficiency, mineral deficiency, antioxidant deficiency, fatty acid deficiency, metabolic imbalance, metabolic impairment, metabolic sensitivity, allergy, satiety, or the effectiveness of a healthy diet. In some embodiments, the vitamin deficiency comprises a deficiency of a vitamin comprising Vitamin A, Vitamin B1, Vitamin B2, Vitamin B3, Vitamin B5, Vitamin B6, Vitamin B7, Vitamin B8, Vitamin B9, Vitamin B12, Vitamin C, Vitamin D, Vitamin E, and Vitamin K. In some embodiments, the mineral deficiency comprises a deficiency of a mineral comprising calcium, iron, magnesium, zinc, or selenium. In some embodiments, the antioxidant deficiency comprises a deficiency of an antioxidant comprising glutathione, or coenzyme Q10 (CoQ10). In some embodiments, the fatty acid deficiency comprises a deficiency in polyunsaturated fatty acids or monounsaturated fatty acids. In some embodiments, the metabolic imbalance comprises glucose imbalance. In some embodiments, the metabolic impairment comprises impaired metabolism of caffeine or drug therapy. In some embodiments, the metabolic sensitivity comprises gluten sensitivity, glycan sensitivity, or lactose sensitivity. In some embodiments, the allergy comprises an allergy to food (food allergy) or environmental factors (environmental allergy). In some embodiments, the methods further comprise administering a treatment to the individual effective to ameliorate or prevent the specific trait in the individual, provided the genetic risk score indicates a high likelihood that the individual has, or will develop, the specific trait. In some embodiments, the treatment comprises a supplement or drug therapy. In some embodiments, the supplement comprises a vitamin, mineral, probiotic, anti-oxidant, anti-inflammatory, or combination thereof. In some embodiments, the genetic risk score is calculated by: (1) calculating a raw score comprising a total number of the one or more units of risk for each ancestry-specific genetic variant for each subject of the subject group, thereby generating an ancestry-specific observed range of raw scores; (2) calculating a total number of the one or more units of risk for each of the one or more individual-specific genetic variants, thereby generating an individual raw score; and (3) comparing the individual raw score with the ancestry-specific observed range to generate the genetic risk score. In some embodiments, the genetic risk score is calculated by: (1) determining an odds ratio for each of the ancestry-specific genetic risk variants; and (2) if two or more ancestry-specific genetic variants are selected, then multiplying the odds ratio for each of the two or more ancestry-specific genetic variants together. In some embodiments, the wherein the computer-executable code is further configured to cause at least one processor to perform step of determining the predetermined genetic variant by: a) providing unphased genotype data from an individual; b) phasing the unphased genotype data to generate individual-specific phased haplotypes based on the ancestry of the individual; c) imputing individual-specific genotypes not present in the phased individual-specific phased haplotypes using phased haplotype data from a reference group that has the same ancestry as the individual; and d) selecting a genetic variant from the imputed individual-specific genotypes that is in linkage disequilibrium (LD) the individual-specific genetic variant associated with a likelihood that the individual has, or will develop, a specific trait.

BRIEF DESCRIPTION OF THE DRAWINGS

FIG. 5 is a flow chart illustrating an exemplary process for determining the ancestry-specific genetic risk score for an individual using one or more ancestry-specific genetic variants from the trait-associated database.

DETAILED DESCRIPTION OF THE INVENTION

Figure 1:
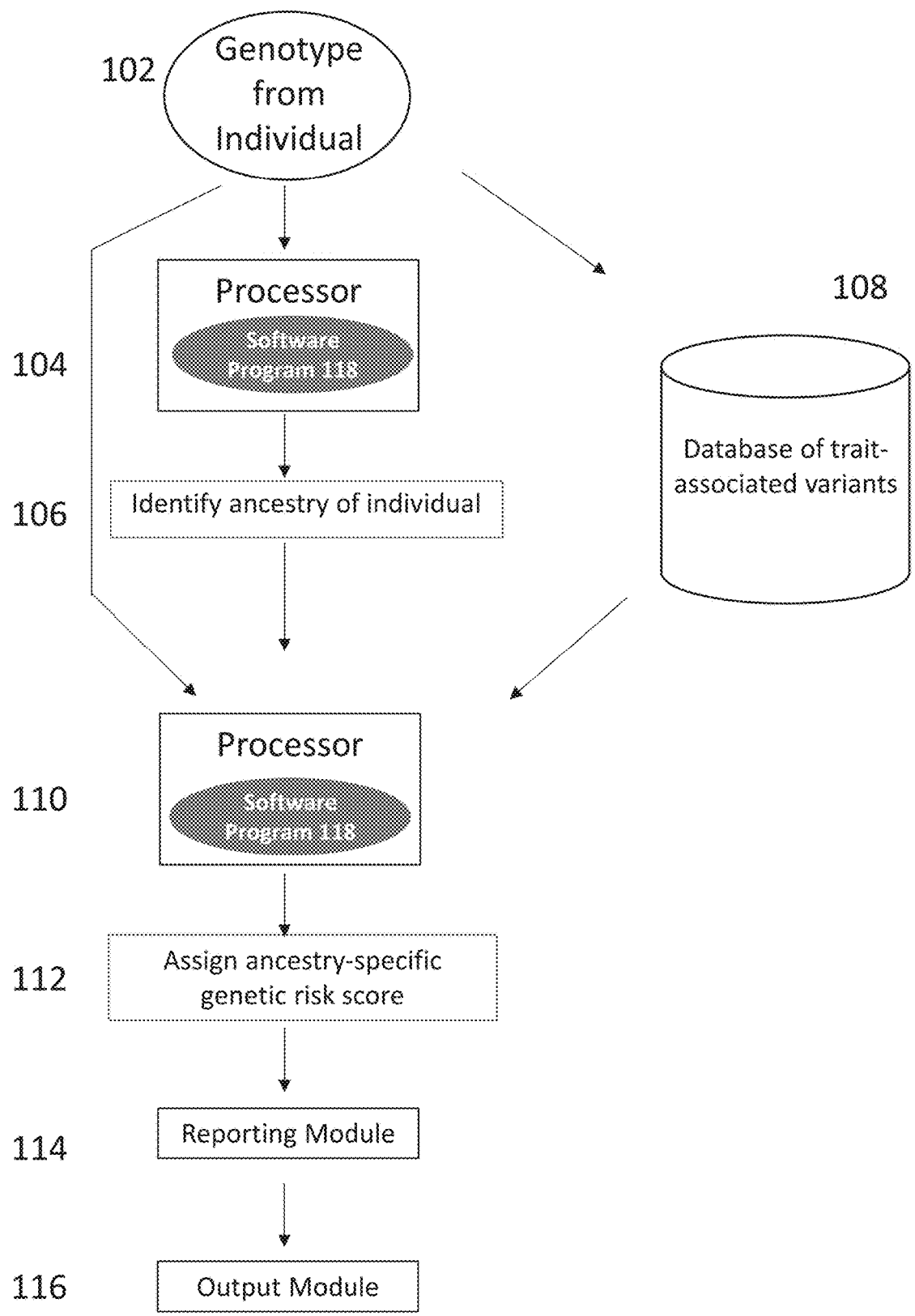
FIG. 1 is a block diagram illustrating an exemplary system for determining the ancestry-specific genetic risk score for an individual.

It is believed that differences in haplotype heterogeneity, as well as recombination rates, contribute significantly to the variance found in linkage disequilibrium (LD) between different ancestral populations. Current genetic risk prediction methods fail to account for the ancestry of the subject group when selecting a proxy genetic variant, which results in selection of a poor indicator of risk in given population. The methods, media, and systems disclosed herein, provide a solution to this problem, by selecting a proxy genetic variant based on LD within the particular ancestral population of which the individual belongs. Further, the methods, media, and systems disclosed herein utilize a software program configured to use predetermined LD patterns, which may be leveraged when calculating a genetic risk score (GRS) for which an individual-specific genetic variant was previously undisclosed. Thus, the present solution, disclosed herein, increases the accuracy and efficiency of a genetic risk prediction, as compared to existing methods.

Current risk prediction methods do not utilize ancestry-specific LD information. However, whether a genetic variant is in LD with another genetic variant is heavily influenced by what ancestral population is studied. In a non-limiting example, two genetic variants that are in LD in a predominantly Caucasian population may not necessarily be in LD in, for example, a Chinese population. The inverse may also be true. Taking into account ancestry-specific LD patterns when calculating a GRS for an individual is advantageous over the state of the art for many reasons including, but not limited to, (i) avoidance of errors (e.g., the two genetic variants are not in LD within that population at all), and (ii) avoidance of counting of a genetic variant more than once. Taking into account ancestry-specific LD patterns yields more accurate GRS predictions by ensuring genetic risk variants in LD are identified, and preventing inflation of a GRS caused by counting a single genetic variant more than once.

Disclosed herein in some embodiments are genetic risk prediction methods, media, and systems for calculating a genetic risk score (GRS) representing a likelihood that an individual will develop a specific phenotype trait, based on the ancestry of the individual. In some embodiments, the GRS is calculated based on a number and type of genetic variants making up the genotype of the individual detected in a sample obtained from the individual, as compared to a subject population of the same ancestry as the individual. In some embodiments, ancestry of the individual is determined by analysis of the genotype of the individual. Also disclosed herein, are methods, media, and systems for recommending a behavioral modification related to the specific phenotypic trait to the individual, based on the calculated GRS for that trait.

Certain Terminologies

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by about 10%, 5%, or 1%.

As used herein "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure, such as compositions for treating skin disorders like acne, eczema, psoriasis, and rosacea.

The terms "increased," or "increase" are used herein to generally mean an increase by a statically significant amount; in some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased" or "decrease" are used herein generally to mean a decrease by a statistically significant amount. In some embodiments, "decreased" or "decrease"

means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

"Ancestry" as disclosed herein, refers to the genetic lineage of an individual.

The term, "genotype" as disclosed herein, refers to the chemical composition of polynucleotide sequences within the genome of an individual.

"Treatment" and "treating" as used herein refer to both therapeutic treatment and prophylactic or preventative measures, wherein the object is to prevent or slow down (lessen) the targeted condition, prevent the condition, pursue or obtain good overall result, or lower the chances of the individual developing the condition even if the treatment is ultimately unsuccessful. In some aspects provided herein, subjects in need of treatment include those already with a disease or condition, as well as those susceptible to develop the disease or condition or those in whom the disease or condition is to be prevented. In some instances, the treatment comprises a supplement. Non-limiting examples of a supplement includes a vitamin, a mineral, an antioxidant, a probiotic, and an anti-inflammatory. In some instances, the treatment comprises a drug therapy. In some instances, the drug therapy comprises an antibiotic, or an antibody or small molecule compound targeting a gene, or gene expression product thereof, disclosed herein.

Non-limiting examples of "sample" include any material from which nucleic acids and/or proteins can be obtained. As non-limiting examples, this includes whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. In various embodiments, the sample comprises tissue from the large and/or small intestine. In various embodiments, the large intestine sample comprises the cecum, colon (the ascending colon, the transverse colon, the descending colon, and the sigmoid colon), rectum and/or the anal canal. In some embodiments, the small intestine sample comprises the duodenum, jejunum, and/or the ileum. Alternatively, a sample can be obtained through primary patient derived cell lines, or archived patient samples in the form of preserved samples, or fresh frozen samples.

Genotype and Genetic Variants

Genome-wide association studies (GWAS) consider hundreds of thousands of genetic variants, including single nucleotide variants, (SNVs), insertions/deletions (indels), and copy-number variants (CNVs) to identify associations between genetic variants within a population and complex clinical conditions and phenotypic traits. Detecting genetic variants associated with specific phenotypic traits in a sample obtained from an individual is considered indicative that the individual has, or will develop, the specific phenotypic trait. In some embodiments, the individual obtains his or her own sample, and provides the sample to a laboratory for processing and analysis. In some embodiments, genetic material is extracted from the sample obtained from the subject. In some embodiments, genetic variants are detected in the genetic material from the sample obtained from an individual using a genotyping assay (e.g., genotyping array, quantitative polymerase chain reaction (qPCR), and/or fluorogenic qPCR). In some embodiments, the genetic information is analyzed to determine the ancestry of the individual.

The term, "genotype" as disclosed herein, refers to the chemical composition of polynucleotide sequences within the genome of an individual. In some embodiments, the genotype comprises SNVs, single nucleotide polymorphisms (SNPs), indels, and/or CNVs. The term, "single nucleotide variant" or "single nucleotide variation" or SNV, as disclosed herein, refers to a variation in a single nucleotide within a polynucleotide sequence. The variation of an SNV may have multiple different forms. A single form of an SNV is referred to as an "allele." By way of example, a reference polynucleotide sequence reading 5' to 3' is TTACG. A SNV at allele position 3 (of 5'-TTACG-3') comprise a substitution of the reference allele, "A" to a non-reference allele, "C." If the "C" allele of the SNV is associated with an increased probability of developing a phenotypic trait, the allele is considered a "risk" allele. However, the same SNV may also comprise a substitution of the "A" allele to a "T" allele. If the T allele of the SNV is associated with a decreased probability of developing a phenotypic trait, the allele is considered a "protective" allele. The SNV may comprise a single nucleotide polymorphism (SNP), in some cases, is an SNV observed in at least 1% of a given population. In some embodiments, the SNV is represented by an "rs" number, which refers to the accession of reference cluster of one more submitted SNVs in the dbSNP bioinformatics database, and which is characterized by a sequence that comprises the total number of nucleobases from 5' to 3', including the variation that was submitted. In some embodiments, a SNV may be further defined by the position of the SNV (nucleobase) within a provided sequence, the position of which is always located at the 5' length of the sequence plus 1. In some embodiments, a SNV is defined as the genomic position in a reference genome and the allele change (e.g. chromosome 7 at position 234,123,567 from G allele to A allele in the reference human genome build 37). In some embodiments, the SNV is defined as the genomic position identified with [brackets] in a sequence disclosed herein. The term, "indel," as disclosed herein, refers to an insertion, or a deletion, of a nucleobase within a polynucleotide sequence. In some embodiments, the indel is represented by an "rs" number, which refers to the accession of reference cluster of one more submitted indels in the dbSNP bioinformatics database, and which is characterized by a sequence that comprises the total number of nucleobases from 5' to 3', including the variation that was submitted. In some embodiments, a indel may be further defined by the position of the insertion/deletion within a provided sequence, the position of which is always located at the 5' length of the sequence plus 1. In some embodiments, an indel is defined as the genomic position in a reference genome and the allele change. In some embodiments, the indel is defined as the genomic position identified with [brackets] in a sequence disclosed herein. The term "copy number variant" or "copy number variation" or "CNV" disclosed herein, refers a phenomenon in which sections of a polynucleotide sequence are repeated or deleted, the number of repeats in the genome varying between individuals in a given population. In some embodiments, the section of the polynucleotide sequence is "short," comprising about two nucleotides (bi-nucleotide CNV) or three nucleotides (tri-nucleotide CNV). In some embodiments, the section of the polynucleotide sequence is "long," comprising a number of nucleotides between four nucleotides and an entire length of a gene.

A genetic variant (e.g., SNV, SNP, indel, CNV) may fall within coding regions of a gene, a non-coding region of a gene, or in an intergenic region between genes. A genetic variant within a coding region of a gene may, or may not, result in a different protein isoform produced due to redundancy in the genetic code. A genetic variant within a non-coding region or intergenic region of a gene may influence the expression and/or activity of the gene, or gene expression products expressed from the gene.

Disclosed herein in some embodiments are methods and systems for determining the genotype of an individual. In some embodiments, the individual is suffering from a disease or condition, or symptoms related to the disease or condition. In some embodiments, the disease or condition comprises a deficiency disease, a hereditary disease, or psychological disease. In some embodiments the disease or condition comprises an immunological disease and/or a metabolic disease. In some embodiments, the immunological disease comprises an autoimmune disease or disorder. Non-limiting examples of an autoimmune disease or disorder include Grave's disease, Hashimoto's thyroiditis, systemic lupus erythematosus (lupus), multiple sclerosis, rheumatoid arthritis, inflammatory bowel disease, Crohn's disease, ulcerative colitis, and cancer. Non-limiting examples of metabolic diseases or conditions include Type 1 diabetes, Type 2, diabetes, diseases affecting absorption of macronutrients (e.g., amino acids, carbohydrates, or lipids), diseases affecting absorption of micronutrients (e.g., vitamins or minerals), diseases affecting mitochondrial function, diseases affecting liver function (e.g., nonalcoholic fatty liver diseases), and diseases affecting kidney function.

Disclosed herein in some embodiments are methods and systems for calculating a genetic risk score (GRS) representing a likelihood that an individual has, or will develop, a specific phenotypic trait, using the genotype and/or genetic variants disclosed herein. In some embodiments, a single genetic variant is used. In some embodiments, two genetic variants are used. In some embodiments, three genetic variants are used. In some embodiments, four genetic variants are used. In some embodiments, five genetic variants are used. In some embodiments, six genetic variants are used. In some embodiments, seven genetic variants are used. In some embodiments, eight genetic variants are used. In some embodiments, nine genetic variants are used. In some embodiments, ten genetic variants are used. In some embodiments, at least about two genetic variants are used. In some embodiments, at least about three genetic variants are used. In some embodiments, at least about four genetic variants are used. In some embodiments, at least about five genetic variants are used. In some embodiments, at least about six genetic variants are used. In some embodiments, at least about seven genetic variants are used. In some embodiments, at least about eight genetic variants are used. In some embodiments, at least about nine genetic variants are used. In some embodiments, at least about ten genetic variants are used. In some embodiments, two genetic variants are used. In some embodiments, at least one genetic variant listed in any one of Tables 1-43 is used. In some embodiments, at least one genetic variant provided in SEQ ID NOS: 1-218 is used. In some embodiments, the genetic variants are used using the methods of detection disclosed herein.

Methods and systems disclosed herein are generally suitable for analyzing a sample obtained from an individual. Similarly, methods disclosed herein comprises processing and/or analysis of the sample. In some instances, the sample is obtained directly, or indirectly, from the individual. In some instances, the sample is obtained by a fluid draw, swab or fluid collection. In some instances, the sample comprises whole blood, peripheral blood, plasma, serum, saliva, cheek swab, urine, or other bodily fluid or tissue.

In some embodiments, the genotype of the individual is determined by subjecting a sample obtained from the individual to a nucleic acid-based detection assay. In some instances, the nucleic acid-based detection assay comprises quantitative polymerase chain reaction (qPCR), gel electrophoresis (including for e.g., Northern or Southern blot), immunochemistry, in situ hybridization such as fluorescent in situ hybridization (FISH), cytochemistry, or sequencing. In some embodiments, the sequencing technique comprises next generation sequencing. In some embodiments, the methods involve a hybridization assay such as fluorogenic qPCR (e.g., TaqMan™ or SYBR green), which involves a nucleic acid amplification reaction with a specific primer pair, and hybridization of the amplified nucleic acid probes comprising a detectable moiety or molecule that is specific to a target nucleic acid sequence. An additional exemplary nucleic acid-based detection assay comprises the use of nucleic acid probes conjugated or otherwise immobilized on a bead, multi-well plate, array, or other substrate, wherein the nucleic acid probes are configured to hybridize with a target nucleic acid sequence. In some instances, the nucleic acid probe is specific to a genetic variant (e.g., SNP, SNV, CNV, or indel) is used. In some instances, the nucleic acid probe specific to a SNP or SNV comprises a nucleic acid probe sequence sufficiently complementary to a risk or protective allele of interest, such that hybridization is specific to the risk or protective allele. In some instances, the nucleic acid probe specific to an indel comprises a nucleic acid probe sequence sufficiently complementary to an insertion of a nucleobase within a polynucleotide sequence flanking the insertion, such that hybridization is specific to the indel. In some instances, the nucleic acid probe specific to an indel comprises a probe sequence sufficiently complementary to a polynucleotide sequence flanking a deletion of a nucleobase within the polynucleotide sequence, such that hybridization is specific to the indel. In some instances, a plurality of nucleic acid probes are required to detect a CNV, specific to various regions within a polynucleotide sequence comprising the CNV. In a non-limiting example, a plurality of nucleic acid probes specific to a single exon CNV within a gene may comprise a high-density of between 2 and 3, 3 and 4, 4 and 5, 5 and 6, and 6 and 7 nucleic acid probes, each nucleic acid probe sufficiently complementary to exonic regions of the gene may be used. In another non-limiting example, long CNVs may be detected utilizing a plurality of nucleic acid probes dispersed throughout the genome of the individual.

In some embodiments, the methods of detecting a genotype of an individual comprise subjecting a sample obtained from the individual to a nucleic acid amplification assay. In some instances, the amplification assay comprises polymerase chain reaction (PCR), qPCR, self-sustained sequence replication, transcriptional amplification system, Q-Beta Replicase, rolling circle replication, or any suitable other nucleic acid amplification technique. A suitable nucleic acid amplification technique is configured to amplify a region of a nucleic acid sequence comprising the risk variant (e.g., SNP, SNV, CNV, or indel). In some instances, the amplification assays requires primers. The known nucleic acid sequence for the genes, or genetic variants, within the genotype is sufficient to enable one of skill in the art to select primers to amplify any portion of the gene or genetic variants. A DNA sample suitable as a primer may be obtained, e.g., by polymerase chain reaction (PCR) amplification of genomic DNA, fragments of genomic DNA, fragments of genomic DNA ligated to adaptor sequences or cloned sequences. Any suitable computer program can be used to design of primers with the desired specificity and optimal amplification properties, such as Oligo version 7.0 (National Biosciences).

In some embodiments, detecting the presence or absence of a genotype comprises sequencing genetic material from a sample obtained from the subject. Sequencing can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. Sequencing methods also include next-generation sequencing, e.g., modern sequencing technologies such as Illumina sequencing (e.g., Solexa), Roche 454 sequencing, Ion Torrent sequencing, and SOLiD sequencing. In some cases, next-generation sequencing involves high-throughput sequencing methods. Additional sequencing methods available to one of skill in the art may also be employed.

In some instances, a number of nucleotides that are sequenced are at least 5, 10, 15, 20, 25, 30, 35, 40, 45, 50, 100, 150, 200, 300, 400, 500, 2000, 4000, 6000, 8000, 10000, 20000, 50000, 100000, or more than 100000 nucleotides. In some instances, the number of nucleotides sequenced is in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5 to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000 nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100 nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500 nucleotides, about 50 to about 300 nucleotides, about 50 to about 200 nucleotides, or about 50 to about 100 nucleotides.

In some instances, the nucleic acid sequence of the genotype comprises a denatured DNA molecule or fragment thereof. In some instances, the nucleic acid sequence comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented. In some instances, the nucleic acid sequence comprises RNA. In some instances, the nucleic acid sequence comprises fragmented RNA. In some instances, the nucleic acid sequence comprises partially degraded RNA. In some instances, the nucleic acid sequence comprises a microRNA or portion thereof. In some instances, the nucleic acid sequence comprises an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof.

Determining a Likelihood that an Individual has, or Will Develop a Specific Phenotypic Trait Aspects disclosed herein provide methods, media, and systems of calculating a genetic risk score (GRS) representing the likelihood that an individual will develop a specific phenotypic trait. In some embodiments, the specific phenotypic trait comprises a phenotypic trait discussed herein, including, but not limited to a clinical trait, a subclinical trait, a physical exercise trait, or a mental trait.

Figure 2:
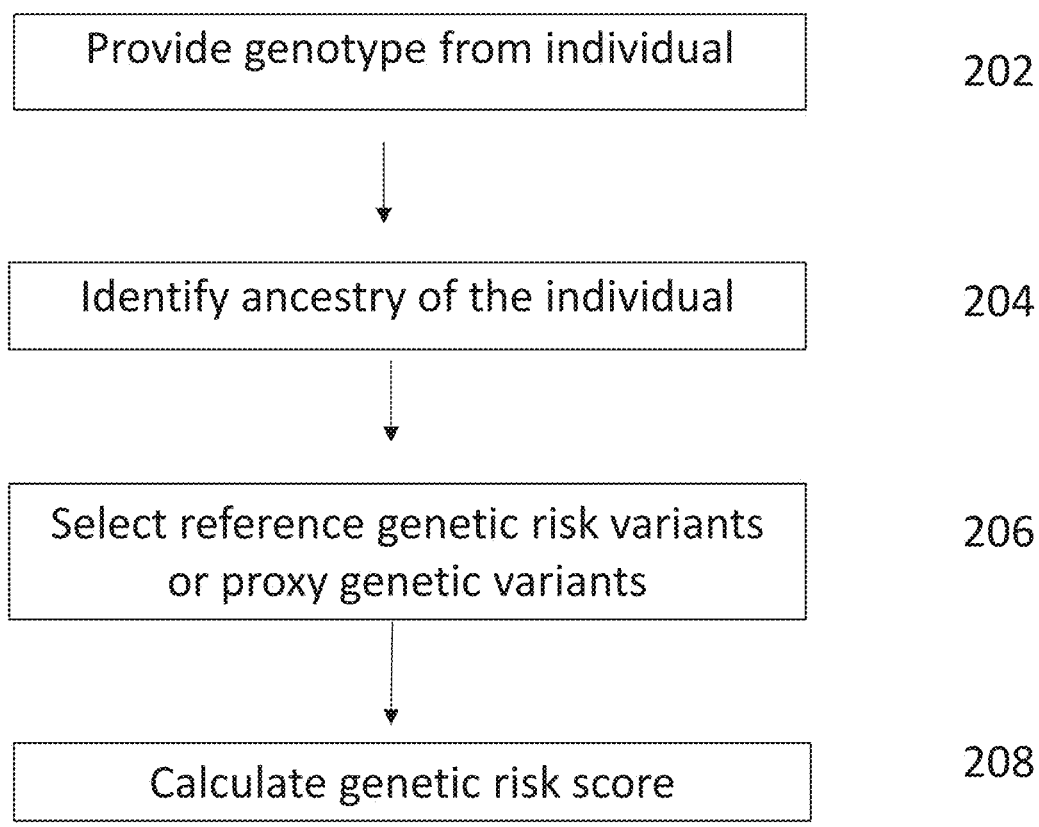
FIG. 2 is a flowchart illustrating an exemplary process for determining a genetic risk score for an individual.

FIG. 2 describes an exemplary workflow to determine a likelihood that an individual has, or will develop, a specific trait by calculating a genetic risk score (GRS). The genotype of the individual is provided 202; the genotype comprising one or more individual-specific genetic variants. Next, the ancestry of the individual is assigned 204 based, at least in part, on the genotype of the individual. Next, one or more reference genetic variants based is selected 206, wherein each of the one or more reference genetic variants correspond to an individual-specific genetic variant of the one or more individual-specific genetic variants or a predetermined genetic variant in a linkage disequilibrium (LD) with an individual-specific genetic variant of the one or more individual-specific genetic variants in a subject population. Next, calculating a genetic risk score for the individual 208 based on the selected one or more reference genetic variants within a subject population, wherein the genetic risk score is indicative of the likelihood that the individual has, or will develop the specific trait. In some instances, the GRS is calculated using any one of the methods disclosed herein.

Figure 3:
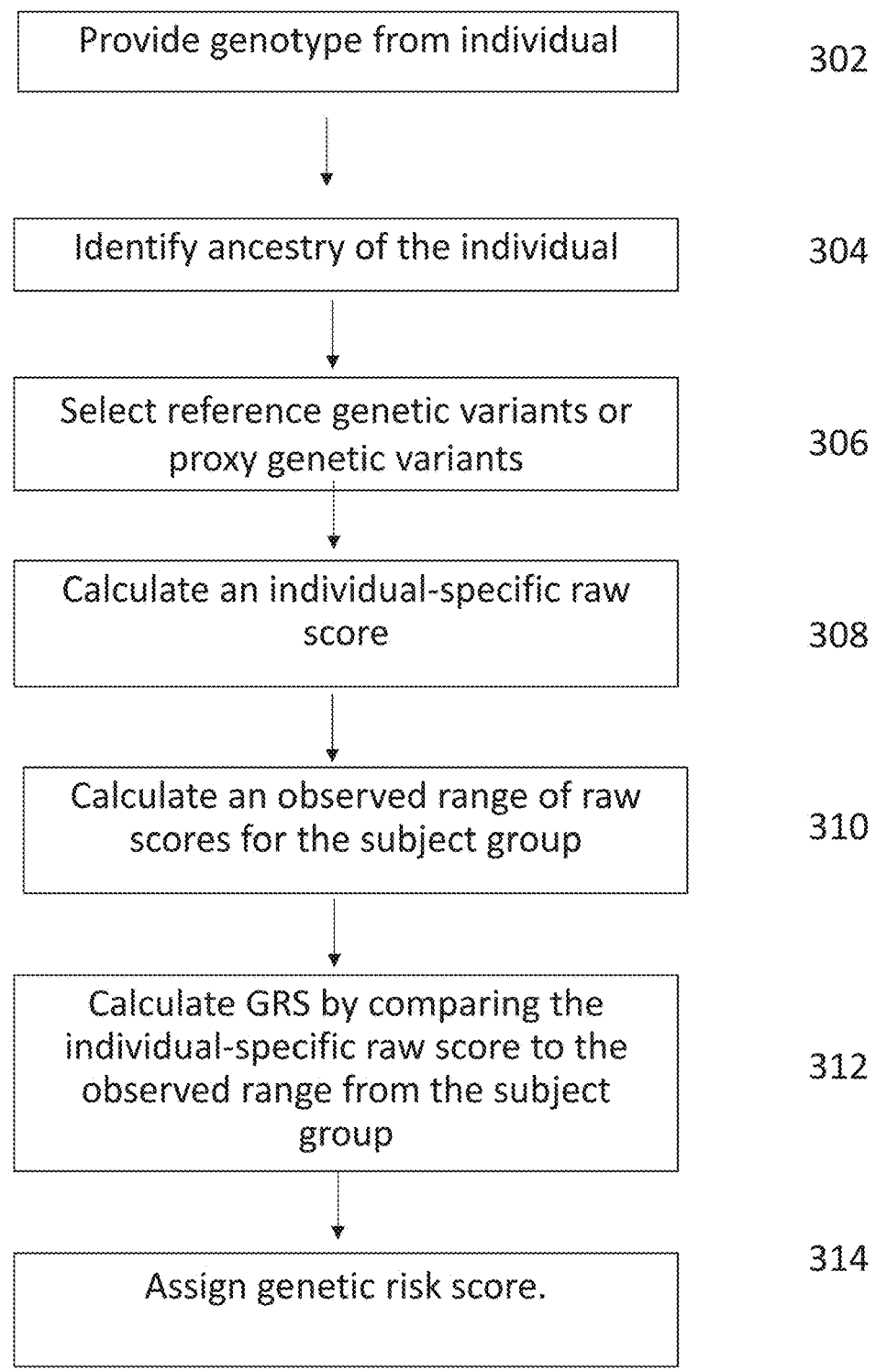
FIG. 3 is a flow chart illustrating an exemplary process for determining the ancestry-specific genetic risk score for an individual using one or more reference genetic variants.

FIG. 3 describes an exemplary workflow to determine a likelihood that an individual has, or will develop, a specific trait based by calculating a GRS as compared to a subject population that is not ancestry specific. The genotype of the individual is provided 302; the genotype comprising one or more individual-specific genetic variants. Next, the ancestry of the individual is assigned based, at least in part, on the genotype of the individual 304. Next, one or more reference genetic variants based is selected 306, wherein each of the one or more reference genetic variants corresponds to an individual-specific genetic variant of the one or more individual-specific genetic variants or a predetermined genetic variant in a linkage disequilibrium (LD) with an individual-specific genetic variant of the one or more individual-specific genetic variants in a subject population. Next an individual-specific raw score is calculated 308. Numerical values are assigned to units of risk within the individual-specific genetic variants, and all numerical values for each individual-specific genetic variant are added together to generate a individual-specific raw score. The same calculations are performed to generate a raw score for each individual within the subject group, thereby generating an observed range of raw scores (observed range) 310. Next, the individual-specific raw score is compared to the observed range to calculate a percentage of risk relative to the subject population 312. Next, a genetic risk score (GRS) is assigned to the individual 314. In some instances, the GRS is in the form as a percentile. In some instances, the percentile is in the form of a z-score.

Figure 4:
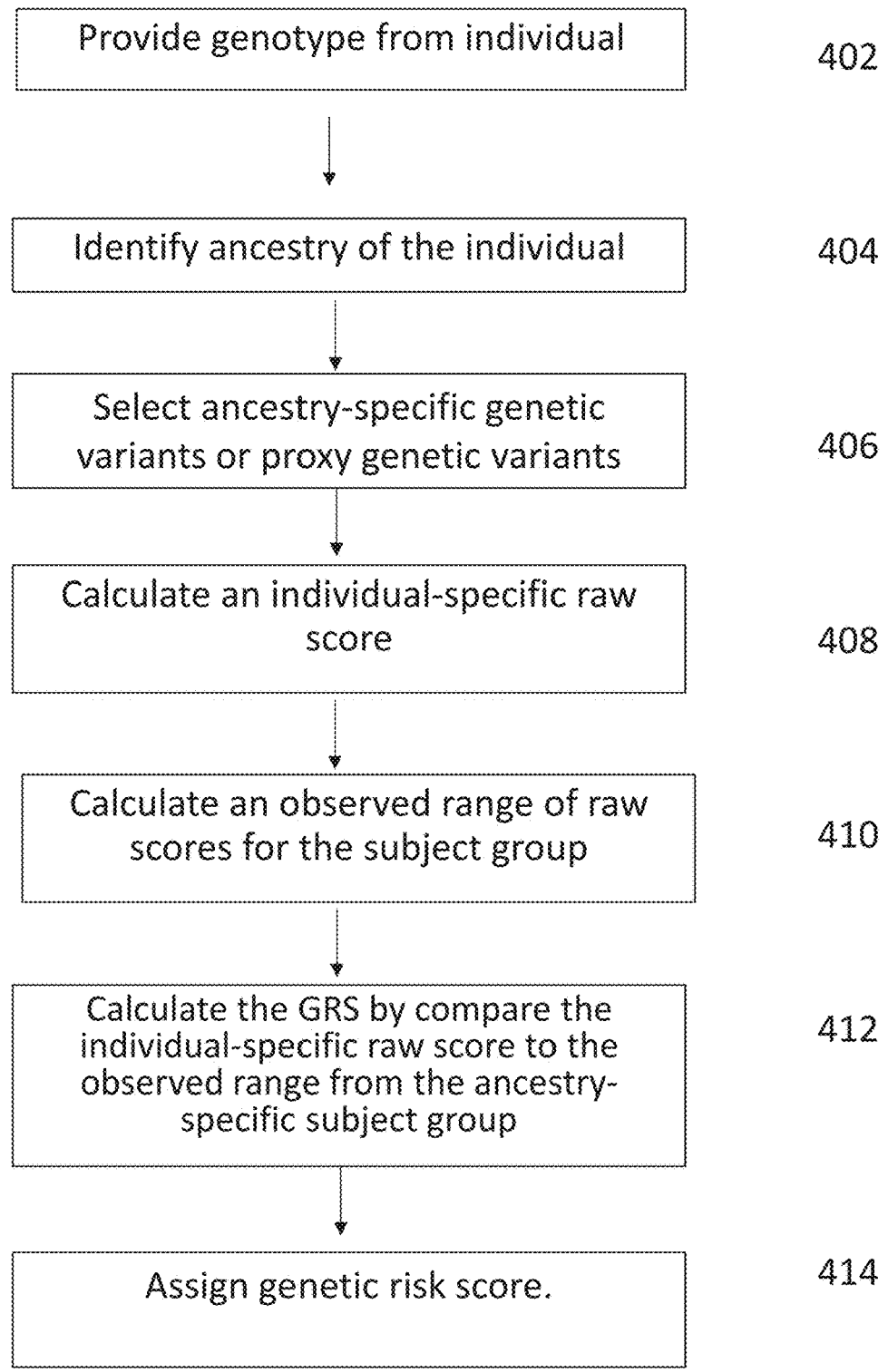
FIG. 4 is a flow chart illustrating an exemplary process for determining the ancestry-specific genetic risk score for an individual using one or more ancestry-specific genetic variants from the trait-associated database.

FIG. 4 describes an exemplary workflow to determine a likelihood that an individual has, or will develop, a specific trait based on the ancestry of the individual. The genotype of the individual is provided 402; the genotype comprising one or more individual-specific genetic variants. Next, the ancestry to the individual is assigned 404 based, at least in part, on the genotype of the individual. Next, ancestry-specific genetic variants derived from subjects with the same ancestry as the individual (ancestry-specific subject group) are selected from a trait-associated variants database 406, selected based, at least in part, on the ancestry of the individual, wherein each of the one or more ancestry-specific genetic variants correspond to: (i) an individual-specific genetic variant of the one or more individual-specific genetic variants, or (ii) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk. Next an individual-specific raw score is calculated 408. Numerical values are assigned to units of risk within the individual-specific genetic variants, and all numerical values for each individual-specific genetic variant are added together to generate an individual-specific raw score. The same calculations are performed to generate a raw score for each individual within the ancestry-specific subject group, thereby generating an observed range of raw scores (observed range) 410. Next, the individual-specific raw score is compared to the ancestry-specific observed range to calculate a percentage of risk relative to the ancestry-specific subject population 412. Next, a genetic risk score (GRS) is assigned to the individual 414. In some instances, the GRS is in the form as a percentile. In some instances, the percentile is in the form of a z-score.

FIG. 5 describes an exemplary workflow to determine a likelihood that an individual has, or will develop, a specific trait based on the ancestry of the individual. The genotype of the individual is provided 502; the genotype comprising one or more individual-specific genetic variants. Next, the ancestry to the individual is assigned 504 based, at least in part, on the genotype of the individual. Next, ancestry-specific genetic variants derived from subjects with the same ancestry as the individual (ancestry-specific subject group) are selected from a trait-associated variants database 506, selected based, at least in part, on the ancestry of the individual, wherein each of the one or more ancestry-specific genetic variants correspond to: (i) an individual-specific genetic variant of the one or more individual-specific genetic variants, or (ii) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk. Next, a genetic risk score (GRS) for the individual is calculated based on the selected one or more ancestry-specific genetic variants 508, wherein the genetic risk score is indicative of the likelihood that the individual has, or will develop the specific trait. In some instances, the GRS is calculating using any one of the methods disclosed herein.

Assigning Ancestry of the Individual

In some instances, ancestry is assigned to the individual by analyzing the genotype of the individual. In some instances, the genotype of the individual is analyzed using a method comprising: maximum likelihood or principal component analysis (PCA). In some instances, a computer program comprising SNPRelate, ADMIXTURE, PLINK, or STRUCTURE is used. For example, after PCA has been performed by SNPRelate, the first two principal components (PC1 and PC2) from populations of known ancestry are each combined into a single data point or centroid. An individual ancestry is classified by its proximity to the nearest centroid of known ancestry. This method relies upon the nearest centroid classification model Trait-Associated Database In some embodiments, a trait-associated database is used. In some instances, the trait-associated database comprises a genotype, a phenotype, and/or an ancestry data of the subject group. In some instances, the subject group is derived from a published genome wide association study (GWAS). In some instances, the published GWAS is recorded in a peer-reviewed journal. In some instances, the trait-associated database enables selection of genetic variants present in a subject group of the same ancestry as the individual. In some instances, the trait-associated database is updated with the genotype, phenotype, and/or ancestry data from the individual. Many databases are suitable for storage and retrieval of genotypic, phenotypic data, and ancestry data. Suitable databases include, by way of non-limiting examples, relational databases, non-relational databases, feature oriented databases, feature databases, entity-relationship model databases, associative databases, and) ML databases. In some embodiments, a database is internet-based. In some embodiments, a database is web-based. In some embodiments, a database is cloud computing-based. In some embodiments, a database is connected to a distributed ledger. In some embodiments, the distributed ledger comprises a blockchain. A database may be based on one or more local computer storage devices.

Selecting One or More Reference Genetic Variants or Ancestry-Specific Genetic Variants In some embodiments, reference genetic variants or ancestry-specific genetic variants are used to calculate a GRS for an individual. In some instances, the one or more genetic variants comprise reference genetic variants from a subject group of any ancestry. In some embodiments, the subject group comprises individuals of one or more ancestries comprising Japanese, German, Irish, African, South African, English, Mexican, Italian, Polish, French, Native American, Scottish, Dutch, Norwegian, Scotch-Irish, Swedish, Puerto Rican, Russian, Hispanic, French Canadian, Filipino, South Korean, North Korean, Indonesian, Chinese, Taiwanese, Malaysian, Afro-Caribbean, Caucasian, American Indian/Alaskan Native (includes people of Central and South American origin with tribal affiliation), Pacific Islander (includes Hawaii, Guam, Samoa, etc.), South Asian (includes people from Afghanistan, India, Pakistan, Bangladesh, Sri Lanka and Nepal), Japanese, Thai, Indigenous Australian (Aboriginal, Torres Strait Islander). In some instances, the one or more reference genetic variant comprises an ancestry-specific genetic variant derived from a subject group comprising individuals of the same ancestry as the individual (ancestry-specific genetic variants).

In some instances, the reference genetic variants are selected, at least in part, because they are derived from a subject group of the same ancestry as the individual (ancestry-specific genetic variants). In some instances, the ancestry of the individual is determined by analyzing the genotype of the individual using the methods disclosed herein. In some instances, the ancestry-specific genetic variants are selected from the trait-associated variants database disclosed herein.

In some instances, the ancestry-specific genetic variants correspond to the individual-specific genetic variant within the genotype of the individual. In some instances, a corresponding individual-specific genetic variant is unknown, in which case another genetic variant is selected to serve as a proxy for the unknown individual-specific genetic variant.

Selecting a Proxy Genetic Variant

In some embodiments, proxy genetic variants are used to calculate a GRS when an individual-specific genetic variant is unknown. In some instances, a predetermined genetic variant is selected to serve as the proxy is provided. Disclosed herein, in some embodiments, are methods of predetermining a proxy genetic variant corresponding to an unknown individual-specific genetic variant, the method comprising: (i) providing unphased genotype data from an individual; (ii) phasing the unphased genotype data to generate individual-specific phased haplotypes based on the ancestry of the individual; (iii) imputing individual-specific genotypes not present in the phased individual-specific phased haplotypes using phased haplotype data from a reference group that has the same ancestry as the individual; and (iv) selecting a genetic variant from the imputed individual-specific genotypes that is in linkage disequilibrium (LD) an individual-specific genetic variant associated with a likelihood that the individual has, or will develop, a specific trait.

In some instances, methods comprise selecting an indel (insertion/deletion) as a proxy for an unknown individual-specific indel. In some instances, methods comprises selecting a copy-number variant (CNV) as a proxy for an unknown individual-specific CNV.

"Linkage disequilibrium," or "LD," as used herein refers to the non-random association of units of risk with genetic risk variants in a given population. LD may be defined by a D' value corresponding to the difference between an observed and expected unit of risk frequencies in the population (D=Pab-PaPb), which is scaled by the theoretical maximum value of D. LD may be defined by an $r^2$ value corresponding to the difference between an observed and expected unit of risk frequencies in the population (D=Pab-PaPb), which is scaled by the individual frequencies of the different loci. In some embodiments, D' comprises at least 0.20. In some embodiments, $r^2$ comprises at least 0.70. In some embodiments, LD is defined by a D' value comprising at least about 0.20, 0.25, 0.30, 0.35, 0.40, 0.45, 0.50, 0.55, 0.60, 0.65, 0.70, 0.75, 0.80, 0.85, 0.90, 0.95 or 1. In some embodiments, LD is defined by an $r^2$ value comprising at least about 0.70, 0.75, 0.75, 0.80, 0.85, 0.90, 0.95, or 1.0. LD differs amongst subject populations belonging to different ancestries. In a non-limiting example, a SNV in LD with a proxy SNV in a subject population of Chinese individuals may not necessarily be in LD within a subject population of Caucasian individuals. Thus, predetermination of a proxy genetic variant based on ancestry-specific phased haplotype data provides increases accuracy of genetic risk predictions based, at least in part, on the proxy.

Calculating a Genetic Risk Score

In some embodiments, methods of calculating a genetic risk score (GRS) for the individual based on the ancestry of the individual are provided. The genetic variants disclosed herein comprise SNVs, indels, and/or CNVs. Each genetic variant comprises units of risk used to calculate a GRS. In some instances, a unit of risk within an SNV comprises the risk allele. In some instances, a unit of risk within an indel comprises the insertion or deletion. In some instances, a unit of risk within a CNV comprises an increase or a decrease in a number of copies of a gene or segment of a gene as compared to a wild-type copy number. A person of skill in the art would understand that many methods of calculating a GRS may be used to calculate the GRS of the individual according to the present methods and systems.

Disclosed herein, in some embodiments, are methods of calculating a GRS of an individual. In some instances, the units of risk within an SNV (e.g., risk allele), an Indel (e.g., insertion or deletion), and/or CNV (e.g., copy number) may be assigned an arbitrary numerical value. In a non-limiting example of calculating a GRS involving SNVs, a homozygous genotype for a risk allele within a SNV (RR) is assigned a numerical value 2; a heterozygous genotype for a risk allele within a SN (R) is assigned a numerical value 1; a genotype that is nonrisk (N) is assigned a numerical value 0. Next, each numerical value for all individual SNVs corresponding to an ancestry-specific SNV, are added together, a divided by a total number of genetic variants used in the model, to generate a raw score for the individual (individual raw score). The same calculations are performed for each individual belonging to the subject group, thereby generating a range of raw scores (observed range). In some instances, the subject group comprises individuals with the same ancestry as the individual. Next, the individual raw score is compared to the observed range to calculate a percentage of risk relative to the subject population.

In another non-limiting example of calculating a GRS involving SNVs, an allelic odds ratio (OR) of each selected ancestry-specific SNV corresponding to an individual-specific SNV is provided and multiplied together. In some instances, the OR is obtained from a replicated, published, and/or peer reviewed GWAS. In some instances, an OR of each selected ancestry-specific SNV corresponding to an individual-specific SNV is provided. Next, the genotypic ORs for each ancestry-specific SNV are added together; the genotypic ORs for the individual are multiplied together. The genotypic ORs for the individual and the subject group are compared, and a percentile GRS is calculated.

In another non-limiting example of calculating a GRS involving an indel, a homozygous genotype for an insertion within the indel (II) is assigned a numerical value 2; a heterozygous genotype for an insertion within the indel (I) is assigned a numerical value 1; a genotype that is nonrisk (N) is assigned a numerical value 0. Next, each numerical value for all individual indels corresponding to an ancestry-specific indel, are added together, a divided by a total number of genetic variants used in the model, to generate a raw score for the individual (individual raw score). The same calculations are performed for each individual belonging to the subject group, thereby generating a range of raw scores (observed range). In some instances, the subject group comprises individuals with the same ancestry as the individual. Next, the individual raw score is compared to the observed range to calculate a risk percentile relative to the subject population.

In another non-limiting example of calculating a GRS involving indels, an odds ratio (OR) of each selected ancestry-specific indel corresponding to an individual-specific indel is provided and multiplied together. In some instances, the OR is obtained from a replicated, published, and/or peer reviewed GWAS. In some instances, an OR of each selected ancestry-specific indel corresponding to an individual-specific indel is provided and the ORs for each risk indel allele are multiplied to generate a genotypic OR for each subject in the subject group. Next, the same calculations are performed for the individual, to generate a genotypic OR for the individual. The genotypic ORs for the individual and the subject group are compared, and a percentile GRS is calculated.

In a non-limiting example of calculating a GRS involving CNVs, a genotype that is nonrisk (e.g., copy number is the same as wild-type, or a normal control) is assigned a numerical value 0, a genotype which comprises of 1 CNV is assigned a numerical value 1, a genotype which comprises of 2 CNVs is assigned a numerical value 2. Next, each numerical value for all individual CNVs corresponding to an ancestry-specific CNV, are added together, a divided by a total number of genetic variants used in the model, to generate a raw score for the individual (individual raw score). The same calculations are performed for each individual belonging to the subject group, thereby generating a range of raw scores (observed range). In some instances, the subject group comprises individuals with the same ancestry as the individual. Next, the individual raw score is compared to the observed range to calculate a risk percentile relative to the subject population.

In another non-limiting example of calculating a GRS involving CNVs, an odds ratio (OR) of each selected ancestry-specific CNV corresponding to an individual-specific CNV is provided and multiplied together. In some instances, the OR is obtained from a replicated, published, and/or peer reviewed GWAS. In some instances, an OR of each selected ancestry-specific CNV corresponding to an individual-specific CNV is provided and the ORs for each CNV are multiplied together to generate a genotypic OR for each subject in the subject group. Next, the same calculations are performed for the individual, to generate a genotypic OR for the individual. The genotypic ORs for the individual and the subject group are compared, and a percentile GRS is calculated.

Disclosed herein, in some embodiments, are methods, media, and systems for calculating a genetic risk score (GRS) using the methods disclosed above involving one or more SNVs and one or more CNVs, one or more SNVs and one or more indels, one or more CNVs and one or more indels, or one or more SNVs, one or more CNVs, and one or more indels.

Phenotypic Traits

The majority of phenotypic traits and complex disease are the result of a combination of genetic and environmental factors, each of which increases or decreases susceptibility to developing the phenotypic trait. An ability to predict whether an individual has, or will develop, a phenotypic trait is useful for a variety of purposes, including, but not limited to, selecting a treatment regimen for the individual, proscribing a diet to the individual, recommending a product (e.g., skin care, hair care, cosmetics, supplements, vitamins, exercise, and the like).

The terms "phenotypic trait," and "specific phenotypic trait" are used interchangeably herein to refer to an observable characteristic of an individual resulting from, at least, the genotype of the individual. The genetic risk prediction methods, media, and systems disclosed herein quantify the load of genetic variation in an individuals' genotype by analyzing the number and type of genetic variants, as compared to a reference population. The number and type of genetic variants present in a sample obtained from an individual can tell you whether the individual has an increased or decreased likelihood (or risk) of developing a certain phenotypic trait. In some cases, the specific phenotypic trait adversely affects the health or wellness of the individual. Disclosed herein, in some embodiments are methods, systems, and media for recommending behavioral change to prevent, mitigate, or ameliorate adverse effects of the specific phenotypic trait in an individual.

Aspects disclosed herein provide methods and systems of calculating a genetic risk score (GRS) representing the likelihood that an individual will develop a specific phenotypic trait. The GRS is based one or more genetic variants present in the genome of the individual, or genotype. In some embodiments, the one or more genetic variants is detected in a sample obtained from the individual using the methods disclosed herein. In some embodiments, the one or more genetic variants comprise a SNV, an indel, and/or a CNV. In some embodiments, the one or more genetic variants present in the genotype of the individual are associated with an increased likelihood that the individual has, or will develop, a specific phenotypic trait. In some embodiments, the one or more genetic variants present in the genotype of the individual are associated with a decreased likelihood that the individual has, or will develop, a specific phenotypic trait. In some embodiments, the phenotypic trait comprises a clinical trait, a subclinical trait, a physical exercise trait, a skin trait, a hair trait, an allergy trait, a nutrition trait, or a mental trait.

Clinical and Subclinical Traits

In some embodiments, a clinical trait comprises a disease or condition, or subclinical trait of the disease or condition. In some embodiments, the clinical trait comprises a diagnosable disease or condition. In some embodiments, the subclinical trait comprises a sub-diagnosable disease, condition, or other phenotype associated with a disease or condition. In some embodiments, the disease or condition comprises a deficiency disease, a hereditary disease, or psychological disease. In some embodiments the disease or condition comprises an immunological disease and/or a metabolic disease cataract risk, glaucoma risk, joint inflammation risk, kidney stone risk, overall inflammation risk, pelvic floor dysfunction, inflammatory biomarker CRP, ESR, IL18, age-related cognitive decline, age-related hearing loss, vitiligo, elevated homocysteine risk. Non-limiting examples include insomnia risk, kidney stone risk, and periodontitis. In some embodiments, the immunological disease comprises autoimmune disease or disorders. Non-limiting examples of autoimmune diseases or disorders include Grave's disease, Hashimoto's thyroiditis, systemic lupus erythematosus (lupus), multiple sclerosis, rheumatoid arthritis, inflammatory bowel disease, Crohn's disease, ulcerative colitis, and cancer. Non-limiting examples of metabolic diseases or conditions include Type 1 diabetes, Type 2 diabetes, diseases affecting absorption of macronutrients (e.g., amino acids, carbohydrates, or lipids), diseases affecting absorption of micronutrients (e.g., vitamins or minerals), diseases affecting mitochondrial function, diseases affecting liver function (e.g., nonalcoholic fatty liver diseases), and diseases affecting kidney function. A subclinical trait may include a subdiagnosable condition or disorder associated with the disease or conditions disclosed herein.

Skin Traits

In some embodiments, the phenotypic trait comprises a trait related to the skin of the individual (skin trait). In some embodiments, the skin trait comprises a rate of collagen breakdown. The rate of collagen breakdown may be affected by genetic variations within genes encoding MMP, MMP-3, MMP-1 collagen breakdown enzymes. Non-limiting examples of genetic variations within genes encoding collagen breakdown enzymes includes the single nucleotide variants (SNVs) disclosed in Table 1.

TABLE 1

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 1 | rs495366 | 11 | 102695108 | G | A | MMP | 0.64 | 6E-34 | 0.44 | TGTCCTTTCTTAGCAGAGCAGGATTTTGACCTAAATTTCTGCAAACTATA[G/A]TCTTATGGTTATGACTCTTTTTGTAAGTTGATCACTCATTCACAAGGATG |
| 2 | rs11226373 | 11 | 104334239 | G | A | MMP-3, MMP-1 | 0.15 | 1E-18 | 0.44 | AATAAGCCCCCTCCCACTACTTCCCATTTATGAATCTGTGGCATACTAC[A/C/G]TTACTATTTTCTATGAACCTTTCCTGGATCACTTAACATGTTTACTACAA |

In some embodiments, the skin trait comprises a level of dryness. Skin hydration, and therefore level of dryness, may be affected by genetic variations within the gene encoding aquaporin 3. A non-limiting example of a genetic variation within the gene encoding aquaporin 3 associated with a level of dryness of the skin includes the SNV disclosed in Table 2.

TABLE 2

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 3 | rs17553719 | 9 | 33447579 | G | A | aquaporin 3 | 0.3 | NR | NR | GGCGGGGCAGGCGGCGGCGCTGTCGGGCGGGCAGGGGTGGCGGGAGGCGG[T/C/G]GGCGCAGCGAGCAGCGGCCTCCAGCGCTGGTGGCTCCCTTTATAGGAGCG |

In some embodiments, the skin trait comprises an antioxidant deficiency of the skin. Antioxidant deficiency of the skin may be affected by genetic variations within genes encoding NQO1, SOD2, NFE2L2, GPX1, and/or CAT. Non-limiting examples of genetic variations within genes encoding NQO1, SOD2, NFE2L2, GPX1, and CAT that are associated with antioxidant deficiency of the skin include the SNVs disclosed in Table 3.

TABLE 3

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 4 | rs1800566 | 16 | 69745145 | T | C | NAD(P)H dehydrogenase[quinone] 1 | NR | NR | NR | TTGAATTCGGGCGTCTGCTGGAGTGTGCCCAATGCTATATGTCAGTTGAG[G/A]TTCTAAGACTTGGAAGCCACAGAAATGCAGAATGCCACTCTGAGGATACA |
| 5 | rs4880 | 6 | 160113872 | T | C | Superoxide dismutase II | NR | NR | NR | AGGGCAGGTCGGGGAGGCTGTGCTTCTGCCTGGAGCCCAGATACCCCAA[A/G]CCGGAGCCAGCTGCCTGCTGGTGCTGAAGACGAGAAAGCACAGCCCGGTC |

TABLE 3-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 6 | rs6706649 | 2 | 178130071 | T | C | Nuclear factor erythroid 2-related factor 2 | NR | NR | NR | GGGAGATGTGGACAGCTCCGGCAGCTCGTGTTCGCAGTCACCCTGAACGC[C/T]CTCCTCTGAACTCCCACGTGTCTCCATTCTCCTAAGCTCAGGTCGTCAAA |
| 7 | rs6721961 | 2 | 178130037 | T | G | Nuclear factor erythroid 2-related factor 2 | NR | NR | NR | CCTTCCCGGGCTGGGGCCAGTGGGCCCTGCCTAGGGGAGATGTGGACAGC[T/C/G]CCGGCAGCTCGTGTTCGCAGTCACCCTGAACGCCCTCCTCTGAACTCCCA |
| 8 | rs1050450 | 3 | 49394834 | C | T | Glutathione peroxidase 1 | NR | NR | NR | ACTGCAACTGCCAAGCAGCCGGGGTAGGAGGGGCGCCCTAGGCACAGCTG[G/A]GCCCTTGAGACAGCAGGGCTTCGATGTCAGGCTCGATGTCAATGGTCTGG |
| 9 | rs1001179 | 11 | 34460231 | G | A | Catalase | NR | NR | NR | GCGGCCTGAAGGATGCTGATAACCGGGAGCCCCGCCCTGGGTTCGGCTAT[C/T]CCGGGCACCCCGGGCCGGCGGGGCGAGGCTCTCCAATTGCTGGGCCAGAG |

In some embodiments, the skin trait comprises an impairment to detoxify the skin. The ability of skin to detoxify may be affected by genetic variations within genes encoding LOC157273, SGOL1, TBC1D22B, FST, MIR4432, RNASEH2C, and/or TGFB2. Non-limiting examples of genetic variations within genes encoding LOC157273, SGOL1, TBC1D22B, FST, MIR4432, RNASEH2C, and TGFB2 associated with an impairment to detoxify the skin include the SNVs disclosed in Table 4.

TABLE 4

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 10 | rs330071 | 8 | 9159895 | G | A | LOC157273 | 0.65 | 9E−07 | 0.21 | GAAACTAAGGATAAGTCTCCCCTCTCCCCTGAATTTCAAGATACCTGTGC[G/A]GTTATCAATATGTAAATAAATGTAATTTGAAAGTCACTTTAAAGATTACT |
| 11 | rs75430906 | 3 | 20717929 | A | G | SGOL1 | 0.00 | 1E−07 | 1.24 | TACTTCTAATACATTTTATTGGCACAAAATTGTCACACTGGCCTTACCTA[G/A]AGGTAGAGGACTAGGAAATATAGCTTAACCCTGTGCTCAGGGAGAAGAAA |
| 12 | rs149709 | 6 | 37278933 | C | T | TBC1D22B | 0.20 | 2E−06 | 0.17 | TATATTGTGCCTACTGTGTGCCAGGCACTATATTTAGCACTTTATATATA[T/C]TAACTGCAGCTGGCCTTCAAGTTGGATTTTTTTTTTTTAGGTCATTCCT |
| 13 | rs38055 | 5 | 52560644 | A | G | FST | 0.32 | 5E−09 | 0.17 | CAATTCCATGGCCCATAGAGTTACCCTTTTCCATATGCCTTTGAAATGCC[A/G]GAGATATTTGATCAGTCAGTGTCCCTCCTTTCATGTGCACCCCCTGCCAG |
| 14 | rs4671386 | 2 | 60514993 | C | A | MIR4432 | 0.43 | 2E−06 | 0.17 | TTACGTGAATGGAAGCAAAGTCAAGGCAAGTGTCAAGGATGTGTTGAAAA[C/A]CAGATATTCAAAATGGTGGGCAAAACTATGCAAATGACAAGGGCAATGCT |

TABLE 4-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 15 | rs478304 | 11 | 65494260 | T | G | RNASE H2C | 0.55 | 3E−11 | 0.18 | TAAGATTCCACTTGTGAG CAAGGAGACCATATACAG TGCCTTCTCCCAGA[G/T]CA GAACATACAGAGAAAAA AACAACTGCCTAATCTGG GAAGGTGAGATTA |
| 16 | rs1159268 | 1 | 218844906 | A | G | TGFB2 | 0.35 | 4E−08 | 0.16 | GGGATAGAACCAATTGTAT TCAGTGAGGGCCAAGAAA ATTGTAATGCTGT[G/A]CCC ACTAAACAAAAACCATCTG GGAGCCAGATTCACACTAG GGTGGCCAG |

In some embodiments, the skin trait comprises skin glycation. Glycation may be affected by genetic variations within genes encoding SLC24A5, SLC45A2, BCN2, MC1R, C16orf55, SPATA33, ASIP, RALY, and/or NAT2. Non-limiting examples of genetic variations within genes encoding SLC24A5, SLC45A2, BCN2, MC1R, C16orf55, SPATA33, ASIP, RALY, and NAT2, associated with skin glycation include the SNVs disclosed in Table 5.

TABLE 5

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 17 | rs1834640 | 15 | 48392165 | G | A | SLC24A5 | 0.08 | 1E−50 | 2.53 | CTTGTAGTGACTGAGACA CAGTGACATTATATCACA ACCTCAGAAACCAC[A/G] ACATAAACCAAGGAATAA TCAATGCCATAGTTTTTA ATAGTGCAACTAGA |
| 18 | rs16891982 | 5 | 33951693 | C | G | SLC45A2 | 0.83 | 3E−11 | 1.58 | AGAGAGAAAGACTTACA AGAATAAAGTGAGGAAAA CACGGAGTTGATGCA[C/G] AAGCCCCAACATCCAAC CTCGACTCCTCTTTCGTA GATGAGAAA |
| 19 | rs62543565 | 9 | 16901067 | A | C | BCN2 | 0.63 | 2E−07 | 0.15 | CTGTCGCCCAGGCTGGAG TGCAGTGGCGTGATCTCG GCTCACTGCAAGCT[C/A] CGCCTCCCACGTTCACGC CATTCTCCTGCCTCAGCC TCCCGAGTAGCTGG |
| 20 | rs35063026 | 16 | 89736157 | T | C | MC1R, C16orf55, SPATA33 | 0.07 | 9E−15 | 0.33 | GCCGTGGCCCCCTTCTCC AGTGCTCTCAGGGAGGGT GCACCAGGCCTGCC[C/T]C CGCCGTGAGAAACTGCAG TCCCCTTCTCCAGTGCTC TCGGGGAGGGTGC |
| 21 | rs6059655 | 20 | 32665748 | A | G | ASIP, RALY | 0.08 | 3E−09 | 0.30 | TCCCACATTTTACCCTGT GAGGAAATCGAGGCTCAG AAAGGCTGAGTGGC[A/G] TGCTCAGGGCATCAGCTC GTAGGGACTGAGCCAGGG TTGGAGTCCAGACT |
| 22 | rs4921914 | 8 | 18272438 | T | C | NAT2 | 0.81 | 8E−42 | 0.11 | TCAATATTTGGATTTAGT CTTCCCTTTATAGAAAAT AAGGACATGTTGTA[C/T]T GTATTCTTGCACACTGAA GTCTGGGGGCTACGATTC ATTCAGCTCATTG |

In some embodiments, the skin trait comprises pigmented spots. Pigmented spots of the skin may be affected by genetic variations in genes encoding SEC5L1, IRF4, MC1R, SLC45A2, TYR, NTM, ASIP, RALY. Non-limiting examples of genetic variations within genes encoding SEC5L1, IRF4, MC1R, SLC45A2, TYR, NTM, ASIP, RALY, associated with pigmented spots include the SNVs disclosed in Table 6.

TABLE 6

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 23 | rs1805007 | 16 | 89986117 | T | C | MC1R | 0.05 | 1E-96 | 1.47 | TCCTGGGCGCCATCGCCGTGGACCGCTACATCTCCATCTTCTACGCACTG[C/A/G/T]GCTACCACAGCATCGTGACCCTGCCGCGGGCGCGGCGAGCCGTTGCGGCC |
| 24 | rs12931267 | 16 | 89818732 | C | G | MC1R | 0.91 | 8E-23 | 0.44 | AGTTCCCAGTTCTCCTCCTGCCTCCGGAGCTGAGTGATGGCTGTGCTTCT[C/G]TGACAGTGTGACCCTCACATTAGTCAACAATAAACAACAAAAACTGCCAC |
| 25 | rs1540771 | 6 | 466033 | A | G | SEC5L1, IRF4 | 0.42 | 4E-18 | 0.34 | TATGGTAGAAGAGAGAGGAGGGTTTCTGTGTTATGAACTGCACGAGTTGG[C/T]TGAGCTCAGTCTATCACGTGTGTGGTGGGCACATGGCCAGACTCCATGTG |
| 26 | rs4268748 | 16 | 90026512 | T | C | MC1R | 0.72 | 3E-15 | 0.01 | CAGCCCTGTGGTTGATATAAGGAGGAGCAGAGAGCCAGGTGGGGCTGCAG[T/C]TCTGTTTCTGGGGGAGGTGGGCTCAGAGGTGGCTGGGGCTTTTCTTTAAG |
| 27 | rs16891982 | 5 | 33951693 | C | G | SLC45A2 | 0.83 | 3E-11 | 1.58 | AGAGAGAAAGACTTACAAGAATAAAGTGAGGAAAACACGGAGTTGATGCA[C/G]AAGCCCCAACATCCAACCTCGACTCCTCTTTCGTAGATGAGAAACTCTGT |
| 28 | rs1126809 | 11 | 89017961 | A | G | TYR | NR | 2E-08 | 0.60 | TCTTAGTCTGAATAACCTTTTCCTCTGCAGTATTTTTGAGCAGTGGCTCC[G/A]AAGGCACCGTCCTCTTCAAGAAGTTTATCCAGAAGCCAATGCACCCATTG |
| 29 | rs6059655 | 20 | 32665748 | G | A | ASIP, RALY | 0.90 | 1E-07 | 0.22 | TCCCACATTTTACCCTGTGAGGAAATCGAGGCTCAGAAAGGCTGAGTGGC[A/G]TGCTCAGGGCATCAGCTCGTAGGGACTGAGCCAGGGTTGGAGTCCAGACT |

In some embodiments, the skin trait comprises youthfulness. "Youthfulness" as disclosed herein refers to a quality of the skin comprising a slow rate of aging, or appears newer or younger than it is. Youthfulness may be affected by genetic variations within genes encoding EDEM1. A non-limiting example of a genetic variation within the gene encoding EDEM1 associated with youthfulness includes the SNV disclosed in Table 7. In some embodiments, Youthfulness refers to a quality of the skin comprising a rate of aging that is slower by 1 month, 2 months, 3 months, 4 months, 5 months, 6 months, 7 months, 8 months, 9 months, 10 months, 11 months, 12 months, 1 year, 2 years 3 years, 4 years or 5 years, as compared to a rate of aging in an individual who does not express the SNV disclosed in Table 7.

TABLE 7

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 30 | rs7616661 | 3 | 5965543 | G | T | EDEM1 | 0.04 | 5E-08 | NR | ATCCTAGACTTAATTTATCAAAGGAATCCCATGACTTCAGGAATAGCCA[T/G]GCACTACTCAGTAATTAAACAGGAGCAGCCTGTGGAAGAAAGGACTTCAT |

In some embodiments, the skin trait comprises photoaging. "Photoaging" as disclosed herein refers to the damage to the skin due to ultraviolet radiation and is a major contributor to premature aging. Photoaging may be affected by genetic variations within genes encoding MC1R, NTM, TYR, FBXO40, STXBP5L, ASIP, RALY, FANCA, ID4-RPL29P17. Non-limiting examples of genetic variations within genes encoding MC1R, NTM, TYR, FBXO40, STXBP5L, ASIP, RALY, FANCA, and ID4-RPL29P17 associated with photoaging include the SNVs disclosed in Table 8.

TABLE 8

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 31 | rs1805007 | 16 | 89986117 | T | C | MC1R | 0.14 | 2e−55 | 1.08 | TCCTGGGCGCCATCGCCGTGGACCGCTACATCTCCATCTTCTACGCACTG[C/A/G/T]GCTACCACAGCATCGTGACCCTGCCGCGGGCGCGGCGAGCCGTTGCGGCC |
| 32 | rs12421680 | 11 | 131350968 | A | G | NTM | NR | 6e−06 | 0.41 | ATTTCTAGACCGATGACTGCATATAAAGCAATGCTTGAGTGAAGAAAACA[G/A]TAGAGTAGGTAGAAATGGACATCGATATAGAGAATTTGATACTGATGGAT |
| 33 | rs1126809 | 11 | 89017961 | A | G | TYR | NR | 2e−08 | 0.60 | TCTTAGTCTGAATAACCTTTTCCTCTGCAGTATTTTTGAGCAGTGGCTCC[G/A]AAGGCACCGTCCTCTTCAAGAAGTTTATCCAGAAGCCAATGCACCCATTG |
| 34 | rs322458 | 3 | 120585315 | G | A | FBXO40, STXBP5L | NR | 2e−08 | NR | TACTTTTTAGCTGTGTGACCTTAGATAAATTATTAAACCTTTCTGAGCTT[C/T]AGTTACCTCTTTTTTATCTACAAAATGGAGATAATAAGACATACCTTTTA |
| 35 | rs6059655 | 20 | 32665748 | G | A | ASIP, RALY | 0.10 | 1e−07 | 0.22 | TCCCACATTTTACCCTGTGAGGAAATCGAGGCTCAGAAAGGCTGAGTGGC[A/G]TGCTGCAGGGCATCAGCTCGTAGGGACTGAGCCAGGGTTGGAGTCCAGACT |
| 36 | rs12931267 | 16 | 89818732 | C | G | FANCA | 0.91 | 8e−23 | 0.44 | AGTTCCCAGTTCTCCTCCTGCCTCCGGAGCTGAGTGATGGCTGTGCTTCT[C/G]TGACAGTG |

TABLE 8-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 37 | rs9350204 | 6 | 19996808 | C | A | ID4-RPL29P17 | 0.15 | 2e−06 | NR | TGACCCTCACATTAGTCAACAATAAACAACAAAAACTGCCACAAGCAAACGGAACGATGCTTCCCTCAACTCACTTCTGGGAAAACAATTCA[A/C]AGCACACAGTGGCAGTTCTTGTTTTTAAACAAAGTGGAGCTGAGAGAGGT |

In some embodiments, the skin trait comprises dermal sensitivity. "Dermal sensitivity" as disclosed herein refers to genetic variations that may cause skin barrier defects and promote skin sensitivity and irritation. Dermal sensitivity may be affected by genetic variations within genes encoding RNASEH2C, DDB2, C11orf49, SELL, TGFB2, SGOL1, ER11, LOC157273, MFHAS1, MIR597, MIR4660, PPP1R3B, U6, TNKS, BC017578, TBC1D22B, AL833181, BCL11A, JB153659, PAPOLG, MIR4432, Mir_562. Non-limiting examples of genetic variations within genes encoding RNASEH2C, DDB2, C11orf49, SELL, TGFB2, SGOL1, ER11, LOC157273, MFHAS1, MIR597, MIR4660, PPP1R3B, U6, TNKS, BC017578, TBC1D22B, AL833181, BCL11A, JB153659, PAPOLG, MIR4432, and Mir_562, associated with dermal sensitivity, include the SNVs disclosed in Table 9.

TABLE 9

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 38 | rs478304 | 11 | 65494260 | T | G | RNASEH2C | 0.55 | 3.00E−11 | 0.18 | TAAGATTCCACTTGTGAGCAAGGAGACCATATACAGTGCCTTCTCCCAGA[G/T]CAGAACATACAGAGAAAAAACAACTGCCTAATCTGGGAAGGTGAGATTA |
| 39 | rs747650 | 11 | 47176005 | G | A | DDB2 | 0.32 | 4.00E−09 | 0.22 | GCTGAGCAGAGGATGAACATAGCCTTGGTCGGATCCCTTTATGAGTCAGA[C/T]GGTTTTCTTCCTGTGAGGTGGGTCCTCAGTGGGAGGGACTAGAGACAGGA |
| 40 | rs38055 | 5 | 52560644 | A | G | C11orf49 | 0.32 | 5.00E−09 | 0.17 | CAATTCCATGGCCCATAGAGTTACCCTTTTCCATATGCCTTTGAAATGCC[A/G]GAGATATTTGATCAGTCAGTGTCCCTCCTTTCATGTGCACCCCCTGCCAG |

TABLE 9-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 41 | rs7531806 | 1 | 169651044 | A | G | SELL | 0.42 | 1.00E−08 | 0.20 | TGAGCTTCAGTTTCTTAAAATTTAAAATGAGGACAATACCATCTATGGCC[G/A]GGGATTAAATGCTATGAGGAATGTAAACCAGATGTCAGGTACCATCTCTC |
| 42 | rs1159268 | 1 | 218844906 | A | G | TGFB2 | 0.35 | 4.00E−08 | 0.16 | GGGATAGAACCAATTGTATTCAGTGAGGGCCAAGAAAATTGTAATGCTGT[G/A]CCCACTAAACAAAAACCATCTGGGAGCCAGATTCACACTAGGGTGGCCAG |
| 43 | rs75430906 | 3 | 20717929 | A | G | SGOL1 | 0.00 | 1.00E−07 | 1.24 | TACTTCTAATACATTTATTGGCACAAAATTGTCACACTGGCCTTACCTA[G/A]AGGTAGAGGACTAGGAAATATAGCTTAACCCTGTGCTCAGGGAGAAGAAA |
| 44 | rs330071 | 8 | 9159895 | G | A | ERI1, LOC157273, MFHAS1, MIR597, MIR4660, PPP1R3B, U6, TNKS, BC017578 | 0.65 | 9.00E−07 | 0.21 | GAAACTAAGGATAAGTCTCCCCTCTCCCCTGAATTTCAAGATACCTGTGC[G/A]GTTATCAATATGTAAATAAATGTAATTTGAAAGTCACTTTAAAGATTACT |

In some embodiments, the skin trait comprises a sensitivity to the sun. Sensitivity to the sun refers to the predisposition of some skin types to damage as a result of moderate sun exposure. Sensitivity to the sun may be affected by genetic variations within genes encoding NTM, TYR, MC1R. Non-limiting examples of genetic variations within genes encoding NTM, TYR, MC1R, associated with sensitivity to the sun, include the SNV disclosed in Table 10.

TABLE 10

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 45 | rs12421680 | 11 | 131350968 | A | G | NTM | NR | 6.00E−06 | 0.41 | ATTTCTAGACCGATGACTGCATATAAAGCAATGCTTGAGTGAAGAAAACA[G/A]TAGAGTAGGTAGAAATGGACATCGATATAGAGAATTTGATACTGATGGAT |

TABLE 10-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 46 | rs1126809 | 11 | 89017961 | A | G | TYR | NR | 2.00E−08 | 0.60 | TCTTAGTCTG AATAACCTT TTCCTCTGCA GTATTTTTGA GCAGTGGCT CC[G/A]AAG GCACCGTCC TCTTCAAGA AGTTTATCC AGAAGCCAA TGCACCCAT TG |
| 47 | rs1805007 | 16 | 89986117 | T | C | MC1R | NR | 2.00E−19 | 1.66 | TCCTGGGCG CCATCGCCG TGGACCGCT ACATCTCCA TCTTCTACGC ACTG[C/A/G/T]GCTACCAC AGCATCGTG ACCCTGCCG CGGGCGCGG CGAGCCGTT GCGGCC |

Physical Exercise Trait

Disclosed herein, in some embodiments are physical exercise traits comprising a trait related to the fitness of the individual (fitness trait). In some embodiments, the fitness trait comprises exercise aversion. "Exercise aversion" refers to avoidance and/or or dislike of experience exercise. Exercise aversion may be affected by genetic variations within genes encoding PAPSS2, C18orf2, DNAPTP6, TMEM18, LEP, MC4R. Non-limiting examples of genetic variations within genes encoding PAPSS2, C18orf2, DNAPTP6, TMEM18, LEP, and MC4R, associated with exercise aversion, include the single nucleotide variants (SNVs) disclosed in Table 11.

TABLE 11

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 48 | rs10887741 | 10 | 89443310 | C | T | PAPSS2 | NR | 4E−06 | 0.28 | ACAAGAACG AAACAGAGT TCAATGGTC TAAATTTGC ATTCACGTG CAGGG[T/C]T CCTAGAAAT GATGATCCT GCATAATTG TTGTGGAAA TCATTTGTCT TCT |
| 49 | rs8097348 | 18 | 1595021 | A | G | C18orf2 | NR | 7E−06 | 0.31 | AAAATGAAC TTTGTGATGT CTTTTCTCTA TATTTTTGGT TGGGAGGAG TA[G/A]CTAG AATTCCTCTC CTAAATTAG CATTGAATA GCATTCTGT AGAATATTA |
| 50 | rs12612420 | 2 | 201158122 | G | A | DNAPTP6 | NR | 8E−06 | 0.36 | AAACTAGAT CAGTGGTTA CCTGGCAGA ATGTTGGGT GAGGGAAGG TCTCC[G/A]G ATCGGGAGG GAAGTAAAT GAGGATGGG ATTACAAAG |

TABLE 11-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 51 | rs6548238 | 2 | 634905 | T | C | TMEM18 | 0.18 | 1E-02 | 11.80 | GGACACAAAGAGAACAGGAGAAGGGAGGGGAAGGGCAGAAGTCCACAGCTGGGAGCACAGGGA[T/C]TCGGGTGACTTATGCTGGGGCCTATTTCTCGTTCATCCCTACAACTGGCT |
| 52 | rs2167270 | 7 | 127881349 | A | G | LEP | NR | 2E-02 | NR | GCTATAAGAGGGGCGGGCAGGCATGGAGCCCCGTAGGAATCGCAGCGCCA[G/A]CGGTTGCAAGGTAAGGCCCCGGCGCGCTCCTTCCTCCTTCTCTGCTGGTC |
| 53 | rs17782313 | 18 | 57851097 | C | T | MC4R | 0.79 | 2E-02 | 10.10 | CTTTAATGACTACAACATTATAGAAGTTTAAAGCAGGAGAGATTGTATCC[T/C]GATGGAAATGACAAGAAAAGCTTCAGGGGGAAGGTGACATTTAAGTTGGA |

In some embodiments, the fitness trait comprises aerobic performance. Aerobic performance may be affected by genetic variations within genes encoding TSHR, ACSL1, PRDM1, DBX1, GRIN3A, ESRRB, ZIC4, CDH13. Non-limiting examples of genetic variations within genes TSHR, ACSL1, PRDM1, DBX1, GRIN3A, ESRRB, ZIC4, and CDH13, associated with aerobic performance, include the SNVs disclosed in Table 12.

TABLE 12

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 54 | rs7144481 | 14 | 81610942 | C | T | TSHR | NR | 9E-08 | NR | AAGTTAGGCTACCAGCATATTTGAATGCCAGGTGAAATCAAAATAATCTA[C/T]ACTATCTAGAAGACTTTCTTGATGCCAAGTCCAGAGATGTCATTGTGTAG |
| 55 | rs6552828 | 4 | 185725416 | G | A | ACSL1 | NR | 1E-06 | NR | TTTAAACCAACCACCAGATATCTAAAGAGGGAATACAGCACAGTGTTGGA[A/G]AGAAAGTACAGAATAGTATTTGAGATCC |

TABLE 12-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 56 | rs10499043 | 6 | 106247137 | A | G | PRDM1 | 0.13 | 4E-06 | NR | TAGATGCAGCCGGACGCGGTGGGCAATGTCCTTGTTTGTGTTCTCTCCCAGTGTTCCAGGTTCTACTGTCAA[C/T]CCAGGCTCAGGCTGTCCCACATCCTCCCACAGAGGTCTTGCTTTGTTTTG |
| 57 | rs10500872 | 11 | 20245723 | A | G | DBX1 | NR | 6E-06 | NR | TGAGAGGAATTCAATCTGAACAAATTTAAGCAAAAGGGATCTTTAGTATG[T/C]GGATTTTGTCATTTTCTAGTAGACACCAAGGACAGGGCTGTAGTGGGGCC |
| 58 | rs1535628 | 9 | 105016749 | G | A | GRIN3A | 0.09 | 7E-06 | NR | AGAGGATGCTAGGTATCTCAAGGTAGGAAAGCATATCTGTGGACAGAAAG[G/A]ACTGTAGAATAGCCAAATCAGAGGGAAGGGCCACTCTACCTAGTTCAGTG |
| 59 | rs12893597 | 14 | 76812695 | T | C | ESRRB | NR | 7E-06 | NR | AACTGCTATGTGTCCTAAGTGGGAATGCTAACCCCTCTGATCGGCTGAGA[C/T]GCCTACAGCCCAGCCTTCTCTAAATCCCCAAAGGCCAGACCCTGAAATGA |
| 60 | rs11715829 | 3 | 146957166 | A | G | ZIC4 | 0.08 | 9E-06 | NR | TCACCAATATATTATTTTACTTATCAGTGAAATCAAAGGACTTTACATAT[T/C]TAGATTCCAAAACAACCTATTGTGATAATTTCTTACCTAGAAAGGTTTCT |

In some embodiments, the fitness trait comprises difficulty losing weight. Difficulty losing weight may be affected by genetic variations within genes encoding FTO, TMEM18, MC4R, KCTD15, CHST8, PPARG, NEGR1, IRS1, SFRS10, ETV5, DGKG, ATP2A1, SH2B1, BDNF, SEC16B, RASAL2, NOS1AP, AIF1, NCR3, MSRA, TNKS, SPRY2, SH3PXD2B, NEURL1B, BCDIN3D, FAIM2, CHRNA9, RBM47, RGMA, MCTP2, MIR4275, PCDH7, TENM2, PRR16, FTMT, SLC24A5, SDCCAG8, COL25A1, NEURL1B, SH3PXD2B, ERBB4, MIR4776-2, STXBP6, NOVA1, DEFB112, TFAP2D, EEF1A1P11-LOC105378866, MTIF3-RNU6-63P, NRXN3, CEP120, and/or LOC105378866-RN7SL831P. Non-limiting examples of genetic variations within genes encoding FTO, TMEM18, MC4R, KCTD15, CHST8, PPARG, NEGR1, IRS1, SFRS10, ETV5, DGKG, ATP2A1, SH2B1, BDNF, SEC16B, RASAL2, NOS1AP, AIF1, NCR3, MSRA, TNKS, SPRY2, SH3PXD2B, NEURL1B, BCDIN3D, FAIM2, CHRNA9, RBM47, RGMA, MCTP2, MIR4275, PCDH7, TENM2, PRR16, FTMT, SLC24A5, SDCCAG8, COL25A1, NEURL1B, SH3PXD2B, ERBB4, MIR4776-2, STXBP6, NOVA1, DEFB112, TFAP2D, EEF1A1P11-LOC105378866, MTIF3-RNU6-63P, NRXN3, CEP120, and/or LOC105378866-RN7SL831P, associated with difficulty losing weight, include SNVs disclosed in Table 13.

TABLE 13

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 61 | rs9939609 | 16 | 53820527 | A | T | FTO | 0.41 | 4E−51 | 0.33 | TTAGAATGTCTGAATTATTATTCTAGGTTCCTTGCGACTGCTGTGAATTT[T/A]GTGATGCACTTGGATAGTCTCTGTTACTCTAAAGTTTTAATAGGTAACAG |
| 62 | rs8050136 | 16 | 53816275 | A | C | FTO | 0.41 | 1E−47 | 8.04 | TGCCAGCTTCATAGCCTAGTCTAGGCATGCCAGTTGCCCACTGTGGCAAT[C/A]AATATCTGAGCCTGTGGTTTTTGCCTTAGGTAAACTGTAGAGATGGACTC |
| 63 | rs7561317 | 2 | 644953 | G | A | TMEM18 | 0.84 | 2E−18 | 6.47 | AGCACTGGCTTAGAAGATGTAGGCAGAGATGACAAGTGACACTTCCTGTC[A/G]TCTGCCTACAAGTTCCCAAAGATCCTCCCCTTTCTTGCTCTGTTTTCACC |
| 64 | rs6499640 | 16 | 53769677 | A | G | FTO | 0.65 | 6E−14 | 5.50 | ATAAGCTTTCTGCCTCAATCTATCTGTGTAAGGAACAGGGTTTCTCTGAA[G/A]GTATCTTTGAAATACTCTACCATCAGTTCATATTTCTACTTTCACCTAAG |
| 65 | rs12970134 | 18 | 57884750 | A | G | MC4R | 0.30 | 5E−13 | 4.66 | CGGTTCTAAGCAACAGATACTGATACTGACTCTTACCAAACAAAGCATGA[G/A]CAAACAAAGAAAACAAAGA |

TABLE 13-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 66 | rs9941349 | 16 | 53825488 | T | C | FTO | 0.43 | 6E−12 | 0.40 | TTTATCAGA AGGGTGCTT GTTAGTACC TGTATTCAA AGGG TTTACAGCA TGATGAAAT TACATATAT GATGGTTAG CAAGT[C/T]T TGGAATATA TGCAGAGGA ATAACTTTA TTACAATGA CTATTTACTT TTT |
| 67 | rs29941 | 19 | 34309532 | C | T | KCTD15, CHST8 | 0.69 | 7E−12 | 4.18 | TAGACAAGC AGAGCCCTG CCAGGCCCA TGGTGACCT CTGCAGACC TAGGA[A/G]C TGCAGGCAG AGTTGGGGG CTCGTTCCTG GGGAGGGGC CCACCCCTG AGG |

In some embodiments, the fitness trait comprises endurance. Endurance may be affected by genetic variations within genes encoding PPARGC1A, PPAR-a, TSHR, ESRRB, and/or CDH13. Non-limiting examples of genetic variations within genes encoding PPARGC1A, PPAR-a, TSHR, ESRRB, and CDH13, associated with endurance, include the SNVs disclosed in Table 14.

TABLE 14

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 68 | rs8192678 | 4 | 23815662 | G | A | PPARGC1A | 0.59 | 3E−03 | NR | AGGTAGTTT GGAGAATTG TTCATTACTG AAATCACTG TCCCTCAGTT CAC[C/T]GGT CTTGTCGCTT CGTCGTCAA AAACAGCTT GACTGGGAT GACCGAAGT |
| 69 | rs4253778 | 22 | 46630634 | G | C | PPAR-a | 0.63 | 1E−03 | 0.81 | ACAATCACT CCTTAAATA TGGTGGAAC ACTTGAAGC TTGATATCT AGTTT[G/C/T] GATTCAAAA GCTTCATTTC CCATATTAT GCAAAACTG GTGGTTGTG ATCT |
| 70 | rs7144481 | 14 | 81610942 | C | T | TSHR | NR | 9E−08 | NR | AAGTTAGGC TACCAGCAT ATTTGAATG CCAGGTGAA ATCAAAATA ATCTA[C/T]A |

TABLE 14-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 71 | rs12893597 | 14 | 76812695 | T | C | ESRRB | NR | 7E-06 | NR | CTATCTAGA AGACTTTCTT GATGCCAAG TCCAGAGAT GTCATTGTG TAG AACTGCTAT GTGTCCTAA GTGGGAATG CTAACCCCT CTGATCGGC TGAGA[C/T]G CCTACAGCC CAGCCTTCT CTAAATCCC CAAAGGCCA GACCCTGAA ATGA |
| 72 | rs9922134 | 16 | 83143453 | C | T | CDH13 | NR | 9E-06 | NR | ACTGTATCC ATTATATTCT CATCACCAT CACATGTGG TTGAACGGG CTTC[C/T]GA CTAAAGAAT CTAAACATG TTTAAAACA TTTTTCACCT CCAGTAAAA CT |

In some embodiments, the fitness trait comprises power. Power may be affected by genetic variations within genes encoding TSHR, ESRRB, and/or CDH13. Non-limiting examples of genetic variations within genes encoding TSHR, ESRRB, and CDH13, associated with power, include SNVs disclosed in Table 15.

TABLE 15

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 73 | rs7144481 | 14 | 81610942 | T | C | TSHR | NR | 9E-08 | NR | AAGTTAGGC TACCAGCAT ATTTGAATG CCAGGTGAA ATCAAAATA ATCTA[C/T]A CTATCTAGA AGACTTTCT TGATGCCAA GTCCAGAGA TGTCATTGT GTAG |
| 74 | rs12893597 | 14 | 76812695 | C | T | ESRRB | NR | 7E-06 | NR | AACTGCTAT GTGTCCTAA GTGGGAATG CTAACCCCT CTGATCGGC TGAGA[C/T]G CCTACAGCC CAGCCTTCT CTAAATCCC CAAAGGCCA GACCCTGAA ATGA |
| 75 | rs9922134 | 16 | 83143453 | T | C | CDH13 | NR | 9E-06 | NR | ACTGTATCC ATTATATTCT CATCACCAT CACATGTGG TTGAACGGG CTTC[C/T]GA CTAAAGAAT CTAAACATG |

TABLE 15-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| | | | | | | | | | | TTTAAAACA TTTTTCACCT CCAGTAAAA CT |

In some embodiments, the fitness trait comprises fitness benefits. "Fitness benefits" refers to individuals having certain genetic variations resulting in showing quicker and stronger benefits from exercise while others genetic variation may take longer and results are less apparent. Fitness benefits may be affected by genetic variations within genes encoding KLKB1, F12, CETP, APOE, APOC1, EDN1, SORT1, PLA2G7, LPL, LIPC, GALNT2, SCARB1, LIPG, MS4A4E, ABCA1, TMEM49, LOC101928635, MVK, MMAB, FLJ41733, FADS1, RREB1, COL8A1, and/or GCKR. Non-limiting examples of genetic variations within genes encoding KLKB1, F12, CETP, APOE, APOC1, EDN1, SORT1, PLA2G7, LPL, LIPC, GALNT2, SCARB1, LIPG, MS4A4E, ABCA1, TMEM49, LOC101928635, MVK, MMAB, FLJ41733, FADS1, RREB1, COL8A1, and GCKR, associated with fitness benefits, include the SNVs disclosed in Table 16.

TABLE 16

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 76 | rs4253238 | 4 | 187148387 | T | C | KLKB1 | 0.54 | 1E−122 | 5.14 | CCTATACAC TTCTATGTGT CTTTTCTTAT TTCTGTGCTG CAACCAGGT GG[C/T]ATAA CCTCTCACCT GATTCCTTA GCTCTAGTG AAGTTATTTT CGTGCATG |
| 77 | rs2731672 | 5 | 176842474 | C | T | F12 | 0.76 | 1E−67 | 4.61 | ATTTTTGCTG GAATTATAA AGCTAGAGG CCTTCTCTTT CCATGGAGG TTG[T/C]CAC ATTCCTAAC AAATGAGCC TGGAGCTGC TGGCAGCCA TCTTTAACAT C |
| 78 | rs1532624 | 16 | 57005479 | A | C | CETP | NR | 1E−66 | 3.09 | GATTAGTTA TGAGCATAC TTTGGCAAA TCTCTGCCCC TTTGGGCTG CAGC[C/A]TC ACAAGCTGT GTGGCGTTG GGCAAGTCT ATAGAACTC AGGACAAAT GGG |
| 79 | rs445925 | 19 | 45415640 | T | C | APOE, APOC1 | 0.89 | 1E−56 | 0.07 | CAGCAACCA TCCACAGAG ACATCCTGG AGCCTGGGA AGGAGAAGG ACAAA[G/A/C] AGCCCCCTT TTTTAAATTT TTTTTATGTT TTTGAGACG GAGTCTCAC TCT |
| 80 | rs1864163 | 16 | 56997233 | G | A | CETP | 0.80 | 7E−39 | 4.12 | CCCTACCCC CACCCTCCA TCCCCTGGT GCCCTGGGG |

TABLE 16-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 81 | rs9989419 | 16 | 56985139 | G | A | CETP | 0.65 | 3E-31 | 1.72 | GGATTTATTGGAGT[G/A]TATCAACCTCTCCAACAGCCCCTCTAAGAGTCAGGCTTCAAAGGGTCCTTGGAGCAGCAGAGTCTGATGTTGTGTACTTCAGGGAGCTGGAGTTCTATGA[A/G]GGAAGAGCGAGGAGGCATGTGGGAGGAAGAACAGCCCCACTGAGGCCTGC |
| 82 | rs5370 | 6 | 12296255 | G | T | EDN1 | 0.78 | 1E-27 | 2.96 | ATGAGAAACAGCGTCAAATCATCTTTCATGATCCCAAGCTGAAAGGCAA[G/T]CCCTCCAGAGAGCGTTATGTGACCCACAACCGAGCACATTGGTGACAGAC |

In some embodiments, the fitness trait comprises reduced heart beat in response to exercise (e.g., recovery rate). Reduced heart beat in response to exercise may be affected by genetic variations within genes encoding RBPMS, PIWIL1, OR6N2, ERBB4, CREB1, MAP2, and/or IKZF2. Non-limiting examples of genetic variations within genes encoding RBPMS, PIWIL1, OR6N2, ERBB4, CREB1, MAP2, and IKZF2, associated with a reduced heart beat in response to exercise include the SNVs disclosed in Table 17.

TABLE 17

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 83 | rs2979481 | 8 | 30262786 | C | T | RBPMS | NR | NR | NR | TCTTCCCTGGAGGGGCTGTTTTCACTGTGATGCCCGCAACATACCAAGAG[T/C]GGAATCCTGTCTGAGGAGTGCAGCTCCGGTCTCACCATGTGGGCAGGGCA |
| 84 | rs11060842 | 12 | 130850356 | C | T | PIWIL1 | NR | NR | NR | AGATGCTGTCATGAAGTCCTAGATAGTCATCACTTTCTAACAAGGCCCTA[T/C]GCTGAACTTAATCTCTGTAAGTGGCAGAGGCATTTGAAACAGAGGGCTGC |
| 85 | rs857838 | 1 | 158750550 | A | C | OR6N2 | NR | NR | NR | AAAGTAGAAAAATTGTAAGTAGAATTATCGTTCATTG |

TABLE 17-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 86 | rs10932380 | 2 | 212390350 | G | A | ERBB4 | NR | NR | NR | GGGACTGTC TATA[A/C]CT CATTAGATG TTCTCAGTC ACAGCCTCT ATTTTATGA ATAATTGTTT TA CTCTGAGAT GTGCTGGCT TCAGGCACC AGGTCGGCC ACACACTGG AGTAG[G/A] GCACCAAAC AGGTTCTTG AAGTCCCCA ATTTTAGGC CTTGGTTCTT GGAT |
| 87 | rs2254137 | 2 | 208444028 | A | C | CREB1 | NR | NR | NR | AAACCTTTA ACTTAAAAT TAGAAGCAA GTCTGATCA AGAAGTCTC AAGCA[C/A] AGGCTGAGT AGTAATATT TAAGACAAC ACTGCTTAC TAAAGAAAA GAGTT |
| 88 | rs3768815 | 2 | 210552162 | T | C | MAP2 | NR | NR | NR | TTTCTATTCC AACGTTCCT TGGTTATTCT GACTTGTTT GAGAGGAAT GTA[C/T]AGA TGATTTTTAT TTTGCCGCA GGGCTGTCA ATGCTTTTG |
| 89 | rs1394782 | 2 | 213200920 | G | A | ERBB4 | NR | NR | NR | GTTCACTTAG GTGTTTTACC ATACTTCAA TTTGTTTTCA TTGTGTTTTT GGCTTATCT GT[G/A]ACAG CTTTTCAATC AGCTTCCTTT AATTGAGGA CTTGACTTG GTTTCTAA |

In some embodiments, the fitness trait comprises lean body mass. Lean body mass may be affected by genetic variations within genes encoding TRHR, DARC, GLYAT, FADS1, and/or FADS2. Non-limiting examples of genetic variations within genes encoding TRHR, DARC, GLYAT, FADS1, and FADS2, associated with lead body mass, include the SNVs disclosed in Table 18.

TABLE 18

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 90 | rs7832552 | 8 | 110115676 | T | C | TRHR | 0.32 | 4E−10 | 0.06 | CTTTATTTTG CTACTGCCTT GACCTCAAA GGAATGTGA TAGTGTGAG GTA[C/T]GAA TGCTCTTAAT |

TABLE 18-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 91 | rs3027009 | 1 | 159173887 | A | G | DARC | NR | 7E-07 | NR | AAACAGGATCGATCAAGGGTGCTTGACTCTTGTTGTTGGGCAATGGTCCCATTTTAAAATATGCTGTCCCATTGTCCCCTAGAGCCT[A/G]CTTTAACTTGTCAGACCATGTATTCCACTTCATATGCAAG |
| 92 | rs2507838 | 11 | 58472799 | A | C | GLYAT | 0.03 | 2E-08 | NR | AGGCATGCACTCAATAAAGCAACTATACAATCAAGAAATGCAACACAGATACCTAATAAC[C/A/G]ACACGGCAAGAAAAAAACCTAACATATCAATATTAATCTTGAACATAAAC |
| 93 | rs174549 | 11 | 61571382 | G | A | FADS1, FADS2 | 0.30 | 8E-07 | 0.56 | TGGTTATCCAGACTCACTCATCTTCAGCTTCTCAGGGGTCCAATCCTGCA[G/A]TATCTAGTGCCACTGCTCCTTTCTTCCATTCCCATTGGCACCCCCAGCC |

In some embodiments, the fitness trait comprises muscle soreness. Muscle soreness may be affected by genetic variations within genes encoding CD163L1, DARC, CD163, ABO, CRP, CD163, CADM3, CR1, NRNR, NINJ1, CFH, DARC, CPN1, CSF1, HBB, CCL2, and/or IGF2. Non-limiting examples of genetic variations within genes encoding CD163L1, DARC, CD163, ABO, CRP, CD163, CADM3, CR1, NRNR, NINJ1, CFH, DARC, CPN1, CSF1, HBB, CCL2, and IGF2, associated with muscle soreness, include the SNVs disclosed in Table 19.

TABLE 19

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 94 | rs4072797 | 12 | 7549009 | C | T | CD163L1 | 0.04 | 1E-88 | 0.24 | TCCCGAGCAGCGGTTGCTGCCGCCCACCAGCCTCAGGCCCCATGTTGCAT[C/T]ACCTGCACCAAGAACAATGAAGCAAGTAGTTAATGGGTGTGATGGTTTAT |
| 95 | rs12075 | 1 | 159175354 | A | G | DARC | 0.49 | 4E-51 | 0.30 | ATGGAATTCTTCCTATGGTGTGAATGATTCCTTCCCAGATGGAGACTATG[G/A]TGCCAACCTGGAAGCAGCTGCCCCCTGCC |

TABLE 19-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 96 | rs117692263 | 12 | 7625014 | C | T | CD163 | 0.09 | 6E-28 | 0.09 | ACTCCTGTA ACCTGCTGG ATG GAGGAATGA GAAGGCAGC AATCTTTGCT GTTCTGCAG CCTTCGCTG GTAA[T/C]AC CCAGGCAAA TAGGGTCTG GAGTGGACC TCCATCAAA CTGCAGCAG AAT |
| 97 | rs643434 | 9 | 136142355 | G | A | ABO | 0.26 | 9E-25 | 0.25 | CTATGTAAA ATTTTAGAA TCAGCTGTC AACTTTACA AAAATTTCT TCTGG[G/A]G TTTTAAGTG AGATTATGT GGACTCTGT AGATCCATC TGGGGAGAA GTGA |
| 98 | rs7305678 | 12 | 7681181 | T | G | NR | 0.16 | 3E-21 | 0.07 | TATGTTTAA CAGCAGCAT GAAAACAGA CTAATATAG TAAATTTCT GCCAG[T/G]G GAGTGGGGC ATTGCTTAG AAGATACCC AAAAATGTA GAAGTGAGT TTGG |
| 99 | rs1341665 | 1 | 159691559 | G | A | CRP | 0.96 | 2E-20 | 0.20 | AGAATTAAT ACCATGAAA AGGGGGCAG TTCACTCAA CAATATAC TGATA[G/A]G AAACAGAAT ATAAGAGCC AATAGAGAA GTTTTTTGTT GAGAAGTAT AAT |
| 100 | rs3026968 | 1 | 159147452 | T | C | CADM3 | 0.12 | 9E-14 | 0.24 | TTCTTGGTTA TGCTCCCCG ACCTGTTCC ACCACAAAC ACATGACAA AACT[C/T]TG AGATATAGA TCTAGAAAG CCATCTGAT CAACTGCAG AAA |

In some embodiments, the fitness trait comprises muscle damage risk. "Muscle damage" refers to having a predisposition to increase muscle damage risk. Muscle damage risk may be affected by genetic variations within genes encoding IGF-II, MLCK, ACTN3, IL-6, and/or COL5A1. Non-limiting examples of genetic variations within genes encoding IGF-II, MLCK, ACTN3, IL-6, and COL5A1, associated with muscle damage, include the SNVs disclosed in Table 20.

TABLE 20

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 101 | rs3213221 | 11 | 2157044 | G | C | IGF-II | 0.37 | 0.03 | NR | CCTTCCATTTGCAAGAAGCACTAGTAATTTTACACGAGGGGTGACCATCT[C/G]CACGGTCATTATTGCAGGAGCTCAGCGGCATCCACAGCTGCAGGGGCCCA |
| 102 | rs680 | 11 | 2153634 | A | G | IGF-II | 0.28 | 0.00 | NR | GAGAAGGGAGATGGCGGTAGCAGCGACGTGCCCACCTGTGATTTCTGGGG[T/C/G]CCTTCTTTTCTCTTTGCTGGTTCAGGGACTCAAGTCCAGGCCAATTTGAC |
| 103 | rs2700352 | 3 | 123550463 | T | C | MLCK | 0.20 | 0.02 | NR | TTGTTGTGGCAACTGGGCCAGTGGGACAGGAAAGGCGTCCTGAAGCTCTC[G/A]GCTGGGAAGCTCCTGAAGTTGCTCTGAACTGCAGCAGAGGCAGCCGGGAG |
| 104 | rs1815739 | 11 | 66328095 | C | T | ACTN3 | 0.48 | 0.03 | NR | GCCTGCTGACAGCGCACGATCAGTTCAAGGCAACACTGCCCGAGGCTGAC[T/C]GAGAGCGAGGTGCCATCATGGGCATCCAGGGTGAGATCCAGAAGATCTGC |
| 105 | rs1800795 | 7 | 22766645 | C | G | IL-6 | 0.20 | 0.01 | 1.19 | TAGCCTCAATGACGACCTAAGCTGCACTTTTCCCCCTAGTTGTGTCTTGC[C/G]ATGCTAAAGGACGTCACATTGCACAATCTTAATAAGGTTTCCAATCAGCC |
| 106 | rs12722 | 9 | 137734416 | T | C | COL5A1 | 0.61 | 0.01 | 0.60 | CCTAGCTGCACCCCAGCGCCTGGGCCCGCCCCACGCTCTGTCCACACCCA[C/T]GCGCCCCGGGAGCGGGGCCATGCCTCCAGCCCCCCAGCTCGCCCGACCCA |

In some embodiments, the fitness trait comprises muscle repair impairment. Muscle repair impairment may be affected by genetic variations within genes encoding HCP5, HCG26, MICB, ATP6V1G2, and/or DDX39B. Non-limiting examples of genetic variations within genes encoding HCP5, HCG26, MICB, ATP6V1G2, and DDX39B, associated with muscle repair, include the SNVs disclosed in Table 21.

TABLE 21

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 107 | rs115902351 | 6 | 31434621 | G | A | HCP5, HCG26 | NR | 2E-45 | 0.81 | AATCCCCAATGTGAGGGGGTCATGATGATGCTGTGGGCCTCTGGGCATCA[A/G]TGTCATCTCACACCCAAAGTCAGTACTCCCCAAGTTCTCCCTATTTCCC |
| 108 | rs3130614 | 6 | 31476458 | A | T | MICB | NR | 4E-48 | 0.84 | CCCGTGGAGGGATTGTCACTTCTGGTTCCCTGTGGGCAGGAATGGTTTCC[T/A]CGTAGGTCACTGGGGTTTTGGCCAGGAAAAGGGTATGAAATTCATGTGCC |
| 109 | rs9267488 | 6 | 31514247 | G | A | ATP6V1G2, DDX39B | NR | 6E-49 | 0.84 | CTGTCCCCCACCCCCAATTTTCTTTCCAAACTCCTAAGGGAGGAAAGAGG[A/G]GACTCACTCTTTCTGGCATCTGCCACCTTCTCAGCTGCCCGCTTCTCAGC |

In some embodiments, the fitness trait comprises a stress fracture risk. A stress fracture risk may be affected by genetic variations within genes encoding LOC101060363-LOC105376856, ZBTB40, EN1, F1142280, COLEC10, WNT16, ESR1, ATP6V1G1, CLDN14, ESR1FABP3P2, ADAMTS18, SOST, CLDN14, MEF2C, KCNH1, C6orf97, CKAP5, C17orf53, SOST, TNFRSF11A, LOC105373519-LOC728815, PTCH1, SMOC1, LOC646794-LOC101928765, and/or LOC105377045-MRPS31P1. Non-limiting examples of genetic variations within genes encoding LOC101060363-LOC105376856, ZBTB40, EN1, F1142280, COLEC10, WNT16, ESR1, ATP6V1G1, CLDN14, ESR1FABP3P2, ADAMTS18, SOST, CLDN14, MEF2C, KCNH1, C6orf97, CKAP5, C17orf53, SOST, TNFRSF11A, LOC105373519-LOC728815, PTCH1, SMOC1, LOC646794-LOC101928765, and LOC105377045-MRPS31P1, associated with stress fracture risk, include the SNVs disclosed in Table 22.

TABLE 22

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 110 | rs7524102 | 1 | 22698447 | A | G | LOC101060363-LOC10 | 0.18 | 1E-16 | 0.15 | TGACAAGGAGAAATAGATTAGAGAGAA |

TABLE 22-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| | | | | | | 5376856 | | | | TCACAGGAG AAATTTGAG ATGCA[A/G]G GCCAAACCA AAAAGCCCA CCAAGGTCA AAACTAAAT GAAATGTGA ACTT |
| 111 | rs115242848 | 2 | 119507607 | C | T | EN1 | 0.99 | 8E−13 | 0.35 | AAAGGCTCT TACCCTTGG CTCTCCCTTT CCCCTCAGC CTCCTGACC AACC[C/T]CC ACATGGCCC TGTGTGGCA TCCCGTGCC CCCTCCTCTT GGGAACTGT AA |
| 112 | rs10429035 | 7 | 96119481 | G | A | FLJ42280 | NR | 4E−12 | NR | AAAAAATTT CTTGAATGG ATGAGCCTG TATACCCTCT ACTTCCAAT TCAC[G/A]GT CATCACAAC ATAACAGAT GAAAAACAC TCTTCATTTG TCTTAAAAG CT |
| 113 | rs6993813 | 8 | 120052238 | C | T | COLEC10 | 0.50 | 3E−11 | 0.09 | TCCCTTGGG TGTGTAATC TAACATAGT GACAAGTTC TGGAGATTA GGGCA[T/C]G GGCATCTTT GGGGGTTAT TATTCTGCTT ATCCCAAGA ATGTTACCC TTT |
| 114 | rs10242100 | 7 | 120983343 | A | G | WNT16 | NR | 2E−10 | NR | GTGACCTTA TGTTTTGGC AGCTTTAAA ACTATGTGA TATGCACAG TAAGT[A/G]T TTTAAAACA CATTTTAATT TTCTCCAGG ACTGTTAGT ACTAATATG ATA |
| 115 | rs1038304 | 6 | 151933175 | G | A | ESR1 | 0.53 | 4E−10 | 0.08 | TGAGCCACT GCGCCTGGC CAAAACTGG TTTCTAGTTT ATGAGTTCA GCAG[A/G]TA TTTGACTCTG GATTCCTCA ATTTAGTGA TATCACACA AAATGGTAT AA |
| 116 | rs10817638 | 9 | 117322542 | A | G | ATP6V1G1 | 0.65 | 3E−09 | 0.22 | CCTTTGAGA GTTTTTAATC TATCCTAGA CACAGGCAC AGCACGAAA AGAG[A/G]A AACATCCCA |

TABLE 22-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| | | | | | | | | | | GCTTCATTA GGGGAAATT TATAGCTTG CCTAGGGTC ACCA |

In some embodiments, the fitness trait comprises overall injury risk. Overall injury risk may be affected by genetic variations within genes encoding HAO1, RSPO2, EMC2, EIF3E, CCDC91, PTHLH, LOC100506393, LINC00536, EIF3H, CDC5L, SUPT3H, and/or MIR4642. Non-limiting examples of genetic variations within genes encoding HAO1, RSPO2, EMC2, EIF3E, CCDC91, PTHLH, LOC100506393, LINC00536, EIF3H, CDC5L, SUPT3H, and MIR4642, associated with overall injury risk, include the SNVs disclosed in Table 23.

TABLE 23

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 117 | rs2423294 | 20 | 7819768 | T | C | HAO1 | 0.16 | 1E-13 | 0.34 | GTCTAATCC TACAATATT TCCAAACCT CACCCATCC CAGAATAAA TAAAT[G/A]T ATGAGATGA CATTGCAAA TTGGACGCC CAATGTTCA CAAAAGCTG ACTC |
| 118 | rs374810 | 8 | 109096029 | G | A | RSPO2, EMC2, EIF3E | 0.61 | 2E-13 | 0.29 | GACAGCCAA CAGCGCGCC TAACTTGGA GCGAATCCT CTTCGGGCT TTCCA[G/A]A GTGCGGGGG ATAGATAAA GAGTAGCTG GGGAGACGC CCCCTGACC TTGC |
| 119 | rs1979679 | 12 | 28406515 | T | C | CCDC91, PTHLH | 0.36 | 4E-12 | 0.26 | TACTTGACTT TCAGTACCT CCCATTGCT GAGCCTTTT GAGGATTCT CTTA[T/C]GT ATTCATAAG TGTGATTCTC ATTTTTCCAG TGACTCATTT TCCTTGTAT |
| 120 | rs11045000 | 12 | 20184146 | A | G | LOC10 0506393 | 0.46 | 3E-11 | 0.25 | TTCTCCTCTC TTAACTCTC ATTAGGCCA ACTGGCAAG TTTAGATGA TGTC[G/A]TT TAGAAAAAT TGGTCAAAA CTAGAATAT AAACATAAC GTGCAATAT TCC |
| 121 | rs13279799 | 8 | 117541607 | G | A | LINC00 536, EIF3H | 0.32 | 1E-10 | 0.25 | AGGAGACAT TCAGATCAC AAATGGTTG AACCCTGGG AGGACATCA AAAGA[T/C]T GTTTCCAAA GATAAGTTT |

TABLE 23-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 122 | rs927485 | 6 | 44538139 | C | T | CDC5L, SUPT3H, MIR4642 | 0.14 | 9E-09 | 0.29 | CTCAGAACT GGAATCCTC CGAAATGCT CTGC GCTCATGGA GCTTCCTCC AGCCCAGCC TCTGTTCAGT TTTTCCAAG GCTT[G/A]TC ACAGAAAGA GGGCTGGGG TGTTATTTTT AAGTCTTAG CTACCCAGA AT |

In some embodiments, the fitness trait comprises resting metabolic heart rate impairment. Resting metabolic heart rate impairment may be affected by genetic variations within genes encoding FTO. A non-limiting example of genetic variation within genes encoding FTO associated with resting metabolic heart rate impairment, includes the SNV disclosed in Table 24.

TABLE 24

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 123 | rs17817449 | 16 | 53813367 | T | G | FTO | 0.61 | 0.04 | NR | ATTGTTAAA GAAGAGTGA TCCCTTTGTG TTTCAGCTTG GCACACAGA AAC[T/G]GTT TTAATTTAA CAGTCCAGC TCCTTTAATA GATCAATTC TCTATTGTG G |

Nutritional Trait

Disclosed herein, in some embodiments, is a nutritional trait comprising a vitamin deficiency, a mineral deficiency, an antioxidant deficiency, a metabolic imbalance, a metabolic impairment, a metabolic sensitivity, an allergy, satiety, and/or the effectiveness of a healthy diet.

In some embodiments, the nutritional trait comprises a vitamin deficiency. In some instances, the vitamin deficiency comprises a deficiency in Vitamin A, Vitamin B1, Vitamin B2, Vitamin B3, Vitamin B5, Vitamin B6, Vitamin B7, Vitamin B8, Vitamin B9, Vitamin B12, Vitamin C, Vitamin D, Vitamin E, or Vitamin K. A vitamin deficiency may be affected by genetic variations within genes encoding GC, FUT2, HAAO, BCMO1, ALPL, CYP2R1, MS4A3, FFAR4, TTR, CUBN, FUT6, ZNF259, LOC100128347, APOA5, SIK3, BUD13, ZNF259, APOA5, BUD13, KYNU, NBPF3, TCN1, CYP4F2, PDE3B, CYP2R1, CALCA, CALCP, OR7E41P, APOA5, CLYBL, NADSYN1, DHCR7, SCARB1, RNU7-49P, COPB1, RRAS2, PSMA1, PRELID2, CYP2R1, PDE3B, CALCA, CALCP, OR7E41P, MUT, ZNF259, CTNAA2, CDO1, SLC23A1, KCNK9, CYP4F2, LOC729645, ZNF259, BUD13, ST6GALNAC3, NKAIN3, VDAC1P12, RASIP1, MYT1L, PAX3, NPY, ADCYAP1R1, HSF5, RNF43, MTMR4, TMEM215-ASS1P12, FAM155A, CD44, BRAF, CD4, LEPREL2, GNB3, MKLN1, SLC6A1, PRICKLE2, SVCT1, and/or SVCT2. Non-limiting examples of genetic variations within genes encoding GC, FUT2, HAAO, BCMO1, ALPL, CYP2R1, MS4A3, FFAR4, TTR, CUBN, FUT6, ZNF259, LOC100128347, APOA5, SIK3, BUD13, ZNF259, APOA5, BUD13, KYNU, NBPF3, TCN1, CYP4F2, PDE3B, CYP2R1, CALCA, CALCP, OR7E41P, APOA5, CLYBL, NADSYN1, DHCR7, SCARB1, RNU7-49P, COPB1, RRAS2, PSMA1, PRELID2, CYP2R1, PDE3B, CALCA, CALCP, OR7E41P, MUT, ZNF259, CTNAA2, CDO1, SLC23A1, KCNK9, CYP4F2, LOC729645, ZNF259, BUD13, ST6GALNAC3, NKAIN3, VDAC1P12, RASIP1, MYT1L, PAX3, NPY, ADCYAP1R1, HSF5, RNF43, MTMR4, TMEM215-ASS1P12, FAM155A, CD44, BRAF, CD4, LEPREL2, GNB3, MKLN1, SLC6A1, PRICKLE2, SVCT1, and SVCT2, that are associated with vitamin deficiency include the SNVs listed in Table 25.

TABLE 25

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 124 | rs7041 | 4 | 72618334 | T | G | GC | 0.35 | 1E-246 | 2109.34 | GCAAAGTCTGAGTGCTTGTTAACCAGCTTTGCCAGTTCCGTGGGTGTGGC[A/C]TCAGGCAATTTTGCTTTTAGTCGCTCTGCCAGTCTGAAAAACCATTTAAA |
| 125 | rs705117 | 4 | 72608115 | G | A | GC | 0.13 | 5E-91 | 2026.78 | TTCCCTCTTCCAAGACAATATAATATAGTTATGTCACAGTTCTATTTGCA[C/T]GGTGTAAAAAATTCCATGTTTCATTGTCTTCAACGAGTTTATGCTTTGGA |
| 126 | rs2282679 | 4 | 72608383 | C | A | GC | 0.26 | 2E-49 | 0.38 | CAGAGGGACTACTACTTGCTTCCAAAGCTAACAATAAAAAATACCTGGCT[T/G]TGTGAGATAATTAAGAGACAGAGATTTGCTGGGCATGGTGGCTCACGCCT |
| 127 | rs1047781 | 19 | 49206631 | A | T | FUT2 | NR | 4E-36 | 70.21 | CCTGGCAGAACTACCACCTGAACGACTGGATGGAGGAGGAATACCGCCAC[A/T]TCCCGGGGGAGTACGTCCGCTTCACCGGCTACCCCTGCTCCTGGACCTTC |
| 128 | rs4953657 | 2 | 42993782 | T | C | HAAO | 0.39 | 2E-32 | 0.42 | GCTAGTGTTTTAAAGTTATGTAAAAAGACAGACTGGGCAACATGGTGAAA[T/C]CCCCATCTCTACAAAAAAGAAAAAAAAAATTAACAGGGTGTGGTGGTGCA |
| 129 | rs6564851 | 16 | 81264597 | T | G | BCMO1 | 0.61 | 2E-24 | 0.15 | AAAGAAAGGGGGAAAGAATGCTCTGAGTGCCTACTGTATTTTAAGCACTG[T/G]GACATACACAGTTTTACACTGTTTAATTTAAACTTTGTAGCCAGTCAATG |
| 130 | rs602662 | 19 | 49206985 | G | A | FUT2 | 0.53 | 3E-20 | 49.77 | TCACCAGTAATGGCATGGCCTGGTGTCGGGAGAACATTGACACCT |

TABLE 25-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| | | | | | | | | | | CCCAC[G/A]GTGATGTGGTGTTTGCTGGCGATGGCATTGAGGGCTCACCTGCCAAAGAT |

In some embodiments, the nutritional trait comprises a mineral deficiency. In some instances, the mineral deficiency comprises a deficiency in calcium, iron, magnesium, zinc, and/or selenium. In some instances, the mineral deficiency may be affected by genetic variations within genes encoding CASR, TF, TFR2, SCAMPS, PPCDC, ARSB, BHMT2, DMGDH, ATP2B1, DCDC5, TRPM6, SHROOM3, CYP24A1, BHMT, BHMT2, JMY, TMPRSS6, GCKR, KIAA0564, DGKH, HFE, GATA3, VKORC1L1, MDS1, MUC1, CSTA, JMY, HOMER1, MAX, FNTB, SLC36A4, CCDC67, MIR379, FGFR2, LUZP2, PAPSS2, HOXD9, LOC102724653-IGLV4-60, HOOK3, FNTA, MEOX2, LOC101928964, PRPF8, MGC14376, SMYD4, SERPINF2, SERPINF1, WDR81, MIR4778, MEIS1-AS3, PRDM9, CALCOCO1, HOXC13, GPR39, SLC22A16, CDK19, TMOD1, TXNRD1, NFYB, MYOM2, CSMD1, KBTBD11, ARHGEF10, DYNC2H1, DCUN1D5, PDGFD, PRMT7, SERPINF2, WDR81, CRMP1, FLJ46481, KHDRBS2-LOC100132056, CD109, LOC100616530, SLC16A7, FLRT2, KYNU, ARHGAP15, RARB, C3orf58, PLOD2, RPRM, GALNT13, EPHA6, RGS14, SLC34A1, SLC22A18, PHLDA2, CDKN1C, NAP1L4, LOC101929578, ZNF14, ZNF101, ATP13A1, PYGB, CHD5, SDCCAG8, XDH, SRD5A2, CMYA5, RP11-314C16.1, TFAP2A, PTPRN2, CA1, KNOP1P1, RNU7-14P-LOC107987283, FNDC4, IFT172, GCKR, C2orf16, CBLB, LINC00882, LOC107983965, MIR4790, AC069277.1, IRX2, C5orf38, ZNF521, SS18, ATG4C, LPHN2, TTLL7, SAG, DGKD, RN7SKP61-MRPS17P3, GPBP1, STXBP6, NOVA1, TMEM211, and/or MT2A. Non-limiting examples of genetic variations within genes encoding CASR, TF, TFR2, SCAMPS, PPCDC, ARSB, BHMT2, DMGDH, ATP2B1, DCDC5, TRPM6, SHROOM3, CYP24A1, BHMT, BHMT2, JMY, TMPRSS6, GCKR, KIAA0564, DGKH, HFE, GATA3, VKORC1L1, MDS1, MUC1, CSTA, JMY, HOMER1, MAX, FNTB, SLC36A4, CCDC67, MIR379, FGFR2, LUZP2, PAPSS2, HOXD9, LOC102724653-IGLV4-60, HOOK3, FNTA, MEOX2, LOC101928964, PRPF8, MGC14376, SMYD4, SERPINF2, SERPINF1, WDR81, MIR4778, MEIS1-A53, PRDM9, CALCOCO1, HOXC13, GPR39, SLC22A16, CDK19, TMOD1, TXNRD1, NFYB, MYOM2, CSMD1, KBTBD11, ARHGEF10, DYNC2H1, DCUN1D5, PDGFD, PRMT7, SERPINF2, WDR81, CRMP1, FLJ46481, KHDRBS2-LOC100132056, CD109, LOC100616530, SLC16A7, FLRT2, KYNU, ARHGAP15, RARB, C3orf58, PLOD2, RPRM, GALNT13, EPHA6, RGS14, SLC34A1, SLC22A18, PHLDA2, CDKN1C, NAP1L4, LOC101929578, ZNF14, ZNF101, ATP13A1, PYGB, CHD5, SDCCAG8, XDH, SRD5A2, CMYA5, RP11-314C16.1, TFAP2A, PTPRN2, CA1, KNOP1P1, RNU7-14P-LOC107987283, FNDC4, IFT172, GCKR, C2orf16, CBLB, LINC00882, LOC107983965, MIR4790, AC069277.1, IRX2, C5orf38, ZNF521, SS18, ATG4C, LPHN2, TTLL7, SAG, DGKD, RN7SKP61-MRPS17P3, GPBP1, STXBP6, NOVA1, TMEM211, and MT2A, associated with mineral deficiency, include the SNVs listed in Table 26.

TABLE 26

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 131 | rs1801725 | 3 | 122003757 | G | T | CASR | 0.15 | 9E-86 | 0.07 | GCAGCGGCACGGTCACCTTCTCACTGAGCTTTGATGAGCCTCAGAAGAAC[G/T]CCATGGCCCACAGGAATTCTACGCACCAGAACTCCCTGGAGGCCCAGAAA |
| 132 | rs8177240 | 3 | 133477701 | T | G | TF | 0.67 | 7E-20 | 0.07 | TGTTGGAGCTTCTGTTCTCCTGCAGAAAACCTGACAATAAACAATGAACA[T/C/G]ATAAATAAGAACACCTCCAGTAGTTAA |

TABLE 26-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 133 | rs7385804 | 7 | 100235970 | C | A | TFR2 | 0.38 | 1E−18 | 0.06 | GTGCTATCTGAAAAACAAGAAGGCTGACCTGTAATTTAATTTAAAAGCCCTGAGCAGGCTGGGTGCGGTACCT[C/A]ATTCCTATAATCCCAGCATTTTGGGAGGCTGAGGTGGGAGGATTGTTTGA |
| 134 | rs2120019 | 15 | 75334184 | C | T | SCAMP5, PPCDC | NR | 2E−18 | 0.29 | TTCTACTCCTTGGTCCTAGCTTTGTTCCTAGGCGCTGTGCCGCTGTGTCA[T/C]CACCCTGCCCTGTACAATATGCAGGAAGCAAGCGAGGAGGGGGTGCCTC |
| 135 | rs17823744 | 5 | 78344976 | A | G | ARSB, BHMT2, DMGDH | 0.12 | 1E−16 | 0.05 | TTCTCAAGGACCTCCTTTCCCTGCCCTCCTGCACCCCATCACCCCACAAG[A/G]TTTCACAGCTGCAGAGAAAGCTTCATCTGGTAACTAGTGTTACGGGTTTA |
| 136 | rs7965584 | 12 | 90305779 | G | A | ATP2B1 | 0.29 | 1E−16 | 0.01 | TTTACTGTTATTCTGGCCAAGTTTGAGTGGTGATGGTGATAAGTAAGTGC[A/G]TGTGTGTGTGTGTGTGTGTGTGTGTGTGTGTGTGTGTGTGTGTGTTCAATTT |
| 137 | rs3925584 | 11 | 30760335 | C | T | DCDC5 | 0.45 | 5E−16 | 0.01 | GAACAAAAAACCAAATGCATACCTTTGACTACAAAGTTCTACTTCCTCTG[T/C]GTAACTCAAAACTTAAATTCCGGGAGCACAAAAGCTGCTTCAGAGTTGTA |

In some embodiments, the nutritional trait comprises an antioxidant deficiency. In some instances, the antioxidant deficiency comprises a deficiency in glutathione, and/or coenzyme Q10 (CoQ10). The antioxidant deficiency may be affected by genetic variations within genes encoding GGT1, GGTLC2, MYL2, C12orf27, HNF1A, OAS1, C14orf73, ZNF827, RORA, EPHA2, RSG1, MICAL3, DPM3, EFNA1, PKLR, GCKR, C2orf16, NEDD4L, MYO1B, STAT4, CCBL2, PKN2, SLC2A2, ITGA1, DLG5, FUT2, ATP8B1, EFHD1, CDH6, CD276, FLJ37644, SOX9, DDT, DDTL, GSTT1, GSTT2B, MIF, MLIP, MLXIPL, DYNLRB2, CEPT1, DENND2D, COLEC12, LOC101927479-ARHGEF19, LOC105377979, MMP26, DNM1, LUZP1, ADH5P2-L00553139, FST, MIR4708-LOC105370537, LOC105373450-KCNS3, LOC107984041-GRIK2, LINC01520, and/or NQO1. Non-limiting examples of genetic variations within genes encoding GGT1, GGTLC2, MYL2, C12orf27, HNF1A, OAS1, C14orf73, ZNF827, RORA, EPHA2, RSG1, MICAL3, DPM3, EFNA1, PKLR, GCKR, C2orf16, NEDD4L, MYO1B, STAT4, CCBL2, PKN2, SLC2A2, ITGA1, DLG5, FUT2, ATP8B1, EFHD1, CDH6, CD276, FLJ37644, SOX9, DDT, DDTL, GSTT1, GSTT2B, MIF, MLIP, MLXIPL, DYNLRB2, CEPT1, DENND2D, COLEC12, LOC101927479-ARHGEF19, LOC105377979, MMP26, DNM1, LUZP1, ADH5P2-L00553139, FST, MIR4708-LOC105370537, LOC105373450-KCNS3, LOC107984041-GRIK2, LINC01520, and NQO1, associated with antioxidant deficiency, include the SNVs listed in Table 27.

TABLE 27

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 138 | rs2073398 | 22 | 24999104 | C | G | GGT1, GGTLC2 | 0.66 | 1E−109 | 12.30 | CCTGCAGCAGTTCCTGTGCCTTTAAAGCCTCCCCTCCCCCCGCCCCGCCC[C/G]CAGGCCACTAGGGGAGGGAAGGAGGAGCTGGGTCACAGCAGGGAATCTTA |
| 139 | rs12229654 | 12 | 111414461 | T | G | MYL2 | 0.86 | 9E−58 | 0.01 | ATGTCCCCCACATCCCAATACTGTTTTGGAGAAAGGTACTTGCATTTGCA[T/G]TATGGAAATTATTTGTATTATTCAAACATTTGGAGCATCTGCTTGCCTG |
| 140 | rs7310409 | 12 | 121424861 | A | G | C12orf27, HNF1A | 0.41 | 7E−45 | 6.80 | GTTCCCCCACAGGGAGACCCACAGCAGAGACATGACTCACAGGTGGCATC[A/G]GGTCCCTTTGAGTCTCTCTGGTGGGAGAATCTCAACCCACAGAGTAGGAT |
| 141 | rs11066453 | 12 | 113365621 | A | G | OAS1 | 0.87 | 6E−44 | 0.01 | TTTTTTTTTCCGCTGTGCTAATGTAGGGAGAAGTTGTTGGAGGTCACGTC[A/G]CAGTTCACAGCAACCATCTATGTTTGGAGCAAGGATGCTGGAAATAGAA |
| 142 | rs944002 | 14 | 103572815 | A | G | C14orf73 | 0.79 | 6E−29 | 6.30 | GTTTCCTCAACAGTGAAATAGGGACATGGTCACCTTCAGGGGGCAGTTAT[A/G]AGGCTCAGGGTAGGGTATGTTCCAGGCATGGCTATGCCGCACTGTTTATC |
| 143 | rs4547811 | 4 | 146794621 | T | C | ZNF827 | 0.82 | 3E−27 | 6.40 | AGCAATCAGAAGTGCTTTCCCTGGATTTAATAATTAGATGGGAGATAAGA[T/C]CTTTGAAGTAAAGTTAAAG |

TABLE 27-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 144 | rs339969 | 15 | 60883281 | C | A | RORA | 0.38 | 7E-20 | 4.50 | GCCTTTCTACCTAGACCACAGCATTACTGAATAAACCCAGCGCAGATACCGAACTGGTGTCCTTCATTCCAGATTGCAACA[C/A]AACCCCAAACTAGCAAACGTTTAACAGGCGCTTGGCACCCGCACCGGTGG |

In some embodiments, the nutritional trait comprises a metabolic imbalance. In some instances, the metabolic imbalance comprises a glucose imbalance. A metabolic imbalance may be affected by genetic variations within genes encoding G6PC2, MTNR1B, GCK, ADCY5, MADD, ADRA2A, GCKR, MRPL33, ABCB11, FADS1, PCSK1, CRY2, ARAP1, SIX2, SIX3, PPP1R3B, SLC2A2, GLIS3, DPYSL5, SLC30A8, PROX1, CDKN2A, CDKN2B, FOXA2, TMEM195, DGKB, PDK1, RAPGEF4, PDX1, CDKAL1, KANK1, IGF1R, C2CD4B, LEPR, GRB10, LMO1, RREB1, FBXL10, and/or FOXN3. Non-limiting examples of genetic variations within genes encoding G6PC2, MTNR1B, GCK, ADCY5, MADD, ADRA2A, GCKR, MRPL33, ABCB11, FADS1, PCSK1, CRY2, ARAP1, SIX2, SIX3, PPP1R3B, SLC2A2, GLIS3, DPYSL5, SLC30A8, PROX1, CDKN2A, CDKN2B, FOXA2, TMEM195, DGKB, PDK1, RAPGEF4, PDX1, CDKAL1, KANK1, IGF1R, C2CD4B, LEPR, GRB10, LMO1, RREB1, FBXL10, and FOXN3, associated with metabolic imbalance, include the SNVs listed in Table 28.

TABLE 28

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 145 | rs560887 | 2 | 169763148 | C | T | G6PC2 | 0.70 | 9E-218 | 0.08 | TCTGATGTCACCCCCTCTAATTTTGAGTGATCCAGTTTCTTTGCTTTTTA[T/C]GCTTGTATCTATTCTTCCATCGTAGACTGACCTGGTCATTTCTTTGGAGT |
| 146 | rs10830963 | 11 | 92708710 | G | C | MTNR1B | 0.30 | 6E-175 | 0.07 | AAGCTGCCCCTCCTCCAGGCCCCCAGTGATGCTAAGAATTCACACCATCT[C/G]CTATCCAGAACCAGTAACTGCCTGGGAGGTTCCTGATGGGAATATTCTGC |
| 147 | rs4607517 | 7 | 44235668 | A | G | GCK | 0.16 | 7E-92 | 0.06 | TCACTTTTGTGATTTTGTGATGTGTCAGTGCTGGGACTGAATCCAAGTTG[G/A]GTGACAGCTGGGGCGATGCAGCAGAAGGCAGGTCTTGCTTTTTGGTAACA |

TABLE 28-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 148 | rs11708067 | 3 | 123065778 | A | G | ADCY5 | 0.78 | 7E-22 | 0.03 | AGGCCACTGTATCGCTTCGTGTCCCCGTGGAACTCATAAGCAGATTTTGC[A/G]CTCTATTAATCTACATCTGTTTGCACGTCCCTGCTGTCAGCAGCTTCTGT |
| 149 | rs7944584 | 11 | 47336320 | A | T | MADD | 0.75 | 2E-18 | 0.02 | CTGAGGTCAAGTTTTTTTCATATACCTCAACCAAAGCAACATACTGCAAC[A/T]GACTCAATGCAGAGGCAGATAGGAGAATGCAACTATTTGATTCTAAGCCA |
| 150 | rs10885122 | 10 | 113042093 | G | T | ADRA2A | 0.87 | 3E-16 | 0.02 | ACTCTCTTATTTGTCATTGGGGACGGTGTGGTATCAACAGGTTTCACAAG[T/G]TAGGGGGATATGCACCAGGGCTGGAACCCCTCTGCCTTGACGGCACCAGG |
| 151 | rs3736594 | 2 | 27995781 | C | A | MRPL33 | 0.73 | 1E-15 | 0.00 | ATTTTCCCTCCTGCTGAACTGAGCTACTTCTGTGAGCATTGAAATACTTG[A/C]AGGAACCTTTGCTGCTTTCTAGTCCCAGGATTTGTGAGCTCACTGTCTG |

In some embodiments, the nutritional trait comprises a metabolic impairment. In some instances, the metabolic impairment comprises impaired metabolism of caffeine and/or a drug. A metabolic impairment may be affected by genetic variations within genes encoding MTNR1B, CACNA2D3, NEDD4L, AC105008.1, P2RY2, RP11-479A21.1, MTUS2, PRIMA1, and/or RP11-430J3.1. Non-limiting examples of genetic variations within genes encoding MTNR1B, CACNA2D3, NEDD4L, AC105008.1, P2RY2, RP11-479A21.1, MTUS2, PRIMA1, and RP11-430J3.1, associated with metabolic impairment, include the SNVs listed in Table 29.

TABLE 29

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 152 | rs10830964 | 11 | 92719681 | C | T | MTNR1B | 0.88 | 5E-06 | 0.48 | CTGTTTCTTCTGGCAAAAAAGGTTCATCAGAGTTTACAAACTCCGTGTCC[C/T]GAGCTTCATCAGGGTCATCCCACACATCCCCATTCCAA |

TABLE 29-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 153 | rs11706236 | 3 | 55188273 | A | G | CACNA2D3 | 0.86 | 4E−06 | 0.46 | GTTGCAGGGTCC CACTTCCTC ATCCTAAAA TTTGGCTGCT AATTTCTGCT GATGCTCAT GGA[A/G]AA TTTCCCAAA GACCCTGCT CCTGAATGA ATTGAAAGC CTTTGAGTT GAG |
| 154 | rs158856 | 18 | 55910523 | C | T | NEDD4L | 0.66 | 7E−06 | 0.34 | TGGATTCTG TATGTGCGT GTGTGTGCA CGTGTGTTCT GCATGCATC TCCA[C/T]GG CACATTATC TGGAGGTAA CATGATCAT CAGGCCTTG AGCTCTTTTA TA |
| 155 | rs16905439 | 8 | 136989204 | C | T | AC105008.1 | 0.99 | 9E−06 | 1.20 | AAATCCTTA AGGAATAGA GAAGGCTTG AAATGAAGT AGGTGCTTA CTAAA[C/T]G TTTGTCAAA TAAAATAAA TGAGTGGAT TTATGATGC TATGCATGA ATTT |
| 156 | rs1791933 | 11 | 72894848 | C | T | P2RY2 | 0.98 | 8E−06 | 1.31 | AGCTTTGTTC AATGTATTTT AATATTTATT TTAATTTGCT TGCATTATCT [T/C]TCTTTC TATTAATATT CATTATTTTT CTTTACCTTC TTTTATAATG TTGG |
| 157 | rs2065779 | 10 | 112877801 | G | C | RP11-479A21.1 | 0.93 | 3E−06 | 0.60 | ATTGTCTGA TGCATCGTG ACTAAGCTT GGAATGTGC CAACTGTCC CCCAG[G/C]A GTGGCCCTT GGACAGCAG AGCTGGAGC GCCGGGACT CTGAGTGCA GGAA |
| 158 | rs2388082 | 13 | 29961332 | C | G | MTUS2 | 0.89 | 4E−06 | 0.52 | TTCAGAACT TTACAGACG TGTCATAAG TGGCTCAGG AGAGAGGCC CACTG[C/G]A CAGTGGCTG CACATGGAA GGCAGAGCT GACCTTGAA GAGATGAAG GAAA |

In some embodiments, the nutritional trait comprises a metabolic sensitivity. In some instances, the metabolic sensitivity comprises gluten sensitivity, sensitive to salt, glycan sensitivity, and/or lactose sensitivity. A metabolic sensitivity may be affected by genetic variations within genes encoding PIBF1, IRAK1BP1, PRMT6, CDCA7, NOTCH4, HLA-DRA, BTNL2, ARSJ, CSMD1, ALX4, NSUN3, RAB9BP1, GPR65, C15orf32, TSN, CREB1, and/or ARMC9. Non-limiting examples of genetic variations within genes encoding PIBF1, IRAK1BP1, PRMT6, CDCA7, NOTCH4, HLA-DRA, BTNL2, ARSJ, CSMD1, ALX4, NSUN3, RAB9BP1, GPR65, C15orf32, TSN, CREB1, and ARMC9, associated with metabolic sensitivity, include the SNVs listed in Table 30.

TABLE 30

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 159 | rs8002688 | 13 | 73559982 | T | C | PIBF1 | 0.04 | 2E−09 | 2.04 | CTGAAGTTG ATGCTGAAA ATCAACAAG AATATGCAA CAAAACCCA TCAAA[C/T]A CTACTGAAA TAGTAAAGG CCAGGGTCC AGCACAGTG GGTCACACC TATA |
| 160 | rs16890334 | 6 | 79556166 | T | C | IRAK1BP1 | 0.94 | 4E−09 | 5.43 | TTGCAATAT AATGGGTAT TATATGAAA TTATCTTGG GTTTGTGCTT ACAT[T/C]GC AGGAGTGGC AACAAAACA CCATAATCT TTTCAATGCT TATTGCAGC TG |
| 161 | rs1330225 | 1 | 106835943 | T | C | PRMT6 | 0.99 | 7E−09 | 5.16 | GAATATAAT GTTAAACAA CAAGCTCAA ACAACAAAC AACAAACTT CCTGT[T/C]T GCATAACTT GTATTCTAG TGGAGAACG TCGAAAATA AATAAATAA ATAA |
| 162 | rs10930597 | 2 | 174326845 | C | T | CDCA7 | 0.95 | 4E−08 | 3.37 | TGTTGATGT ACCCTTTAG GGTGGGGGA AAGGTTTGG AGAACTCTC TGGTG[C/T]G AAGAGCATG CTTGAGGTA ACCACAAGT GGTGAACAA AGTGCCCCC AAGA |
| 163 | rs3135350 | 6 | 32392981 | G | A | NOTCH4 HLA-DRA, BTNL2 | 0.05 | 9E−08 | 0.51 | AGAGCATAG TCCTCCATG ACTTTCAAT GAAAAACCC GATAGCTTT CATCT[C/T]C TCAATCCTG AAGAGCTGA AGGAGATTT AGGCTGAAC TTAAAGAAA TTTT |
| 164 | rs7658266 | 4 | 114863706 | C | T | ARSJ | 0.79 | 3E−07 | 2.35 | CTTCATTTGG AATAAATCT TTGATCTGG AACCATTTC CATATTTAA AGGC[T/C]AC |

TABLE 30-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 165 | rs2627282 | 8 | 2780956 | G | A | CSMD1 | 0.98 | 3E-07 | 2.33 | TTCGAATGC CATCTCTGTC ATGGACTTT CCTCTCTCCT TTAAGCACA A CGTGTTTCTA AAAATATAC GTAATAACT TGTATAATG ATGATAAAG CTCT[G/A]TA TTACAATTG AATAAGACA GGAAAACTA TTTCAAGTT ATTTGCTGT GTG |

In some embodiments, the nutritional trait comprises a food allergy. In some embodiments, the food allergy comprises a peanut allergy. An allergy to peanut may be affected by genetic variations within genes encoding HLA-DRB1, HLA-DQA1, HLA-DQB1, HLA-DQA2, HCG27, HLA-C, ADGB, RPS15P9, MUM1, RYR1, LINC00992, LOC100129526, FAM118A, SMC1B, MIATNB, ATP2C2, PLAGL1, MRPL42, and/or STAT6. Non-limiting examples of genetic variations within genes encoding HLA-DRB1, HLA-DQA1, HLA-DQB1, HLA-DQA2, HCG27, HLA-C, ADGB, RPS15P9, MUM1, RYR1, LINC00992, LOC100129526, FAM118A, SMC1B, MIATNB, ATP2C2, PLAGL1, MRPL42, and STAT6, associated with a peanut allergy, include the SNVs listed in Table 31.

TABLE 31

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 173 | rs9275596 | 6 | 32681631 | C | T | HLA-DRB1, HLA-DQA1, HLA-DQB1, HLA-DQA2 | 0.36 | 6E-11 | 0.53 | GGGCTTAT TCCAACTT GGCCGTCA CAGAAAG ATCCTCTT CAGCTTTG TTG[C/T]TG AAGGATGT TTTTCTGA TTTTAGAA TTCTAGGT TTGTGTTA GGTGTAGA |
| 174 | rs3130941 | 6 | 31197514 | C | G | HCG27 HLA-C | 0.25 | 1E-10 | 0.10 | ATGTAAAA ATACACAC ACACAAAG TGGAGCTG AGGGCAG GATGGAGA ACT[C/G]TC ATTCTCAG CCCATGAC CTCCATGG ACTTGGAG AAAGACTC AGCCTGGA |
| 175 | rs4896888 | 6 | 147098991 | C | T | ADGB | 0.56 | 3E-07 | 1.90 | CAACCTAC AGGCCACT TGTGTCAG AATCACGT GAGGTACA TTTTAAAC TG[C/T]AG ATTTCTGT GCCCCTCA CCAGACTA CAGAGTTG GAATCTCT GAGAGGTG |

TABLE 31-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 176 | rs758147 | 19 | 1322312 | C | T | RPS15P9, MUM1 | 0.62 | 1E−06 | 1.83 | GAATCTGGCTGAGCTTGGGTGGCACCCAAGGATGCCTGCAGCCCGCCCAG[T/C]GGCACGGGAAGCCCCCTCACCCGCTGGCTGGAAGGGGTGGGAGGCAAGTG |
| 177 | rs3786829 | 19 | 39014184 | C | T | RYR1 | 0.16 | 2E−06 | 1.99 | TCTCCCTCCTCCCATCTCCCTCCTCCTCTCCATCTCCCTCTTCTCTCATC[T/C]CTGTCTCCTTCCTCCTCCTGTATCTTCTCCCTCCTCCCATTTCCCTCCTC |
| 178 | rs1830169 | 5 | 117048725 | C | T | LINC00992, LOC100129526 | 0.21 | 4E−06 | 0.77 | ACACATGCAGGTTTGTTACATAGGTAAACTCGTGTCATGGGGGTTCAGTG[T/C]ACAGGTTATTTCATCACCTAGCTACTAAATGTAGTACCTGATAGTTATTT |
| 179 | rs998706 | 22 | 45735606 | T | C | FAM118A, SMC1B | 0.54 | 4E−06 | 0.60 | TCCAGTGCCTGCTGACAAGAACGAAGGCCCGGGCGATTATTCTCAATAGA[T/C]TGGCTTTCTTCTGCTGTTGCTGCTGTTGTGTGTACATAGATTTTGTCCCC |

In some embodiments, the nutritional trait comprises satiety. Satiety may be affected by genetic variations within genes encoding LEPR. Non-limiting examples of genetic variations within genes encoding LEPR associated with satiety include the SNVs listed in Table 32.

TABLE 32

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 187 | rs4655555 | 1 | 66080269 | A | T | LEPR | 0.22 | 2.0E−08 | 0.07 | AGTTCTCACAGGGCATGGGCTAACAATTATGGTACTGCTCTACATGTAC[T/A]CTGG |

TABLE 32-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 188 | rs12062820 | 1 | 65970495 | T | C | LEPR | NR | 1.6E-14 | 0.10 | AAGGGGACAAGCAAGTAAATGGATGGTGGATGGTGGGACCCAGATTAATTATGTACCAATATTGGTTCATTGGTTATGACCAATGCACCTCACTTA[T/C]ATAGGATAGAAATAATAGGGGAGATTGGGTGTGAAGTATATGGGAATTCT |

Effectiveness of a healthy diet may be affected by genetic variations within genes encoding FGF21, ZPR1, TANK, FNBP1, RNU6-229P-LOC105375346, ARGFX, BEND3, SUMO2P6-LOC105377740, LOC101929216-GDF10, LOC105377451-LOC105377622, CPA3, KCNQ3, THBS4, TENM2, HSPA9P2-LOC105372045, LINC00113-LINC00314, SH3BGRL2, NKAIN2, OPRM1, LOC105377795, NCALD, LOC728503, LOC105370491, LOC107985318-MIA3, BECN1P2-LYPLA1P3, LOC105376778-LINC01082, SOX5, LHX5-AS1-LOC105369990, NBAS, ABCG2, PPARγ2, CLOCK, RARB, FTO, IRS1, TCF7L2, HNMT, and/or PFKL. Non-limiting examples of genetic variations within genes encoding FGF21, ZPR1, TANK, FNBP1, RNU6-229P-LOC105375346, ARGFX, BEND3, SUMO2P6-LOC105377740, LOC101929216-GDF10, LOC105377451-LOC105377622, CPA3, KCNQ3, THBS4, TENM2, HSPA9P2-LOC105372045, LINC00113-LINC00314, SH3BGRL2, NKAIN2, OPRM1, LOC105377795, NCALD, LOC728503, LOC105370491, LOC107985318-MIA3, BECN1P2-LYPLA1P3, LOC105376778-LINC01082, SOX5, LHX5-AS1-LOC105369990, NBAS, ABCG2, PPARγ2, CLOCK, RARB, FTO, IRS1, TCF7L2, HNMT, and PFKL, associated with effectiveness of a healthy diet include the SNVs listed in Table 33.

TABLE 33

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 189 | rs838145 | 19 | 49248730 | G | A | FGF21 | 0.54 | 4E-10 | 0.22 | GGGAGTTGTAGTTTTATTACATAAAATTGCCAGCCGAGGATAGGGAAAAC[G/A]GTATTTACTAGCCTCGGGGAACCTCGGAATCTGCATCTCAGCCTTCTCCA |
| 190 | rs964184 | 11 | 116648917 | C | G | ZPR1 | 0.17 | 1E-09 | 0.30 | GCTTTACATTCCTCCATGACACTAATCACCATCTGATGTACTGTTTTCCT[G/C]ATCTGTTTATTGTCATTTTTCCCCACTAGACTTCAAGTTCCATGAAAGAG |
| 191 | rs197273 | 2 | 161894663 | G | A | TANK | 0.52 | 1E-07 | 0.23 | CAACATGTCATGTGCAATGAAACCAGATAACAGAAGAAA |

TABLE 33-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 192 | rs2007126 | 9 | 132684007 | A | G | FNBP1 | 0.16 | 2E-07 | 0.05 | GGGAAACTCTC[A/G]TTTTTTGTTTAGATGTTATTAATGTGTCACACATTTATACACATGGCACTGCTGGGATTACGGGCATGAGCCACTGTGCCAGGCCTCTTTTTTACACAGA[G/A]TTGTTTTGTGGAAATACGATTGTCAGGTAACAATGACTACTGTTATTC |
| 193 | rs6959964 | 7 | 68905738 | T | C | RNU6-229P - LOC105375346 | 0.63 | 3E-07 | 0.26 | ACATTGCATTTGCCTCCAAAGCTCAAAAACAGAATGAAGCATCACATCAA[T/C]GTCAGCTTCTCTTTTTAAAGAAAAATTTTCTCTCAAAAGTGTCCCAATAT |
| 194 | rs13096657 | 3 | 121300728 | T | C | ARGFX | 0.14 | 4E-07 | 0.37 | AGATGGCAGTTGCAGTGAGCTATAATCAAGCAACTGCACTGCAATCCAGC[C/T]TGGGCTGGTGAGGGAGACTCTGTAAAAAAAAAAAATCAGCTCCTCAGTGG |
| 195 | rs3749872 | 6 | 107388504 | T | C | BEND3 | 0.95 | 4E-07 | 0.59 | TATGACTACCCTGTGTGATTCAATAAATTTTCCAGGACTCTGGTATGACA[C/T]ACTGTTTGCATTCGACTGTTTCCTTTCCCTCTTAAGCATTTGGCCCCCAG |

Allergy Trait

Disclosed herein, in some embodiments, are allergy traits. In some embodiments, an allergy trait comprises a skin allergy, a dust allergy, an insect sting allergy, a pet allergy, an eye allergy, a drug allergy, a latex allergy, a mold allergy, and/or a pest allergy. In some embodiments, the allergy trait comprises allergic inflammation. "Allergic inflammation," as used herein refers to inflammation caused by, or associated with, an allergic reaction.

In some embodiments, the nutritional trait comprises allergic inflammation. In some instances, allergic inflammation may be affected by genetic variations within genes encoding FCER1A, LRRC32, C11orf30, IL13, OR10J3, HLA-A, STAT6, TSLP, SLC25A46, WDR36, CAMK4, HLA-DQB1, HLA-DQA1, STAT6, NAB2, DARC, IL18R1, IL1RL1, IL18RAP, FAM114A1, MIR574, TLR10, TLR1, TLR6, LPP, BCL6, MYC, PVT1, IL2, ADAD1, KIAA1109, IL21, HLA region, TMEM232, SLCA25A46, HLA-DQA2, HLA-G, MICA, HLA-C, HLA-B, MICB, HLA-DRB1, IL4R, ID2, LOC730217, OPRK1, WWP2, EPS15, ANAPC1, LPP, LOC101927026, IL4R, IL21R, SUCLG2, TMEM108, DNAH5, OR6X1, DOCK10, ABL2, COL21A1, and/or CDH13. Non-limiting examples of genetic variations within genes encoding FCER1A, LRRC32, C11orf30, IL13, OR10J3, HLA-A, STAT6, TSLP, SLC25A46, WDR36, CAMK4, HLA-DQB1, HLA-DQA1, STAT6, NAB2, DARC, IL18R1, IL1RL1, IL18RAP, FAM114A1, MIR574, TLR10, TLR1, TLR6, LPP, BCL6, MYC, PVT1, IL2, ADAD1, KIAA1109, IL21, HLA region, TMEM232, SLCA25A46, HLA-DQA2, HLA-G, MICA, HLA-C, HLA-B, MICB, HLA-DRB1, IL4R, ID2, LOC730217, OPRK1, WWP2, EPS15, ANAPC1, LPP, LOC101927026, IL4R, IL21R, SUCLG2, TMEM108, DNAH5, OR6X1, DOCK10, ABL2, COL21A1, and CDH13, associated with allergic inflammation, include the SNVs listed in Table 34.

TABLE 34

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 166 | rs2251746 | 1 | 159272060 | T | C | FCER1A | 0.74 | 5E−26 | 0.09 | CTAAAGAAAGAAGCAAAACCAGGCACAGCTGATGGGTTAACCAGATATGA[T/C]ACAGAAAACATTTCCTTCTGCTTTTTGGTTTTAAGCCTATATTTGAAGCC |
| 167 | rs2155219 | 11 | 76299194 | T | G | LRRC32, C11orf30 | 0.47 | 1E−18 | 0.17 | CTGACATTAATATGAATAGAGCAGATTCCTTTGAGTTAATATTTGTCTGG[G/T]GTGTTTTATTTCATCCACTGACTTCTAACTTTTCTGTGTTCTTAGAGCTG |
| 168 | rs20541 | 5 | 131995964 | A | G | IL13 | 0.19 | 3E−18 | 0.08 | GTTTGTAAAGGACCTGCTCTTACATTTAAAGAAACTTTTTCGCGAGGGAC[A/G]GTTCAACTGAAACTTCGAAAGCATCATTATTTGCAGAGACAGGACCTGAC |
| 169 | rs4656784 | 1 | 159326880 | A | G | OR10J3 | 0.80 | 2E−16 | 0.08 | TGGAAAATTCTTTAGAATAGATCATATGTTAAATCACAAAACAAACCTTA[A/G]CAAATTTGAAAAAATGGAAACATATCAAGTATTTTTTAATACCACAATG |
| 170 | rs2571391 | 6 | 29923838 | A | C | HLA-A | 0.68 | 1E−15 | 0.06 | CTAACTAACTAAATAAATGATAAATAAAGGCGGTGCATGAGCACTGGTGA[A/C]GGGCACTTTGGCTGCATTGAGCACT |

TABLE 34-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 171 | rs1059513 | 12 | 57489709 | T | C | STAT6 | 0.90 | 1E-14 | 0.26 | TGCAAATTTGAGGTGATTAAATTCTTCCTAGGTACATACACGTTCACACAGCTATACACGAAGAATCTCAGCCCT[T/C]GTACTTTTGCATAGTCTCATACACGTATCAGAAGCCTCCACCTGGCTAAC |
| 172 | rs10056340 | 5 | 110190052 | G | T | TSLP, SLC25A46, WDR36, CAMK4 | 0.17 | 5E-14 | 0.18 | CAAACCTCCATATTCATGTCATTGAATGTGGGCTAGTTTCAGAAGGGAAT[T/G]TGAAATTGGACAAGGCAGCTCTCTTTAGCAGAAGCAATTCTCCAACAGGG |

In some embodiments, the allergy trait comprises a pest allergy. In some embodiments, the pest allergy comprises an allergy to mites. An allergy to mites may be affected by genetic variations within genes encoding LOC730217, OPRK1, OR6X1, DOCK10, CDH13, Cap S, IL4, ADAM33, IRS2, ABHD13, LINC00299, IL18, CYP2R1, and/or VDR. Non-limiting examples of genetic variations within genes encoding LOC730217, OPRK1, OR6X1, DOCK10, CDH13, Cap S, IL4, ADAM33, IRS2, ABHD13, LINC00299, IL18, CYP2R1, and VDR, associated with an allergy to mites, include the SNVs listed in Table 35.

TABLE 35

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 180 | rs10142119 | 14 | 98486545 | G | A | L00730217 | 0.52 | 2E-07 | 0.67 | ATCAAAGAAGTGGCTGCTTCATCACATTCACAGGCCTTGTCCACAGCCAA[G/A]AGGAAGAGATCAGAGGTTCTGTTCACCGGCGGGGTAGGACTCTTGGAATT |
| 181 | rs1425902 | 8 | 54119214 | G | A | OPRK1 | 0.26 | 1E-06 | 0.76 | AAGGAAAAGTTCAATATAGAGATTATCATTGCCTGGGAGACATTTGCTTC[G/A]CCTTCTGTTTTCAAATGCTTGCAACATAGAAGACTGGAGTGAATCCAAGA |

TABLE 35-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 182 | rs17744026 | 11 | 123648333 | T | G | OR6X1 | 0.91 | 3E−06 | 1.39 | AAAGTCACCCTTTGCTTCATCCCTTCTCCCTTTATTGTGCACCTATTATA[T/A/G]GTTATACAATGTGTTTGAGCAGATGCAAAAAATAAGACTAATTTACTAAC |
| 183 | rs1843834 | 2 | 225558042 | A | G | DOCK10 | 0.18 | 4E−06 | 0.76 | ATCCCTGGACAAGATCGTAAGTAAAAATAACATTTCATCCTAGGAGGCAC[A/G]GAGAGATTAGAGCCACCCTTAAGGATACAATGGATATGGAGCTGGTGGTC |
| 184 | rs6563898 | 16 | 83358776 | G | A | CDH13 | 0.52 | 8E−06 | 0.60 | TTCCATGTTTCATAAGTTCTTAAGTGATTCTTCTTTAATCCCACTAAATC[A/G]TGACTCCAGATGAGTTTAAGAAATCTTAAGACTATTTTTTAATTATTACA |
| 185 | rs146456111 | 1 | 150705585 | C | A | Cap S | 0.43 | 1E−03 | 0.78 | TAAGAGGGAAAGCTAGCAATCCCACAATGATTTCCTTTATTTCTTGCCAT[C/A]CGAATATATCCTTCTTCACCAAAGTTGTGGCCCCAGCTTTAGAAAAAGAA |
| 186 | rs2243250 | 5 | 132009154 | T | C | IL4 | 0.77 | 1E−03 | NR | CCTGATACGACCTGTCCTTCTCAAAACACCTAAACTTGGGAGAACATTGT[C/T]CCCCAGTGCTGGGGTAGGAGAGTCTGCCTGTTATTCTGCCTCTATGCAGA |

Mental Traits

Disclosed herein, in some embodiments is a mental trait comprising a trait related to the mental health or mental acuity of the individual, mental illness, mental condition. Non-limiting examples of mental health or mental acuity includes a level of stress, short term memory retentions, long term memory retention, creative or artistic (e.g., "right-brained"), analytical and methodical (e.g., "left-brained"). Non-limiting examples of mental illness include schizophrenia, bipolar disorder, manic depressive disorder, autism spectrum disorder, and Down syndrome. Non-limiting examples of a mental condition include depression risk, social anxiety, likelihood of being an introvert, likelihood of being an extrovert. Non-limiting examples of a mental trait include morning person, empathy, worrier personality, mathematical ability, addictive personality, memory performance, OCD predisposition, exploratory behavior, reading ability, experiential learning difficulty, general creativity, general intelligence, impulsivity, inattentive symptoms, mathematical ability, mental reaction time, musical creativity, nail biting, reading and spelling difficulty, verbal and numerical reasoning and misophonia.

In some embodiments, the mental trait comprises memory performance. Memory performance may be affected by genetic variations within genes encoding APOC1, APOE, FASTKD2, MIR3130-1, MIR3130-2, SPOCK3, ANXA10, ISL1, PARP8, BAIAP2, HS3ST4, C16orf82, AJAP1, C1orf174, ODZ4, NARS2, PRR16, FTMT, PCDH20, TDRD3, LBXCOR1, MAP2K5, PTGER3, ZRANB2, AXUD1, TTC21A, GFRA2, DOK2, SLC39A14, PPP3CC, VPS26B, NCAPD3, ZNF236, MBP, RIN2, NAT5, SEMA5A, MTRR, DGKB, ETV1, BHLHB5, CYP7B1, TMEPAI, ZBP1, TBC1D1, KLHL1, DACH1, LRRTM4, C2orf3, B3GAT1, LOC89944, ATP8B4, SLC27A2, CHD6, EMILIN3, RWDD3, TMEM56, SCN1A, KIBRA, and/or NCAN. Non-limiting examples of genetic variations within genes encoding APOC1, APOE, FASTKD2, MIR3130-1, MIR3130-2, SPOCK3, ANXA10, ISL1, PARP8, BAIAP2, HS3ST4, C16orf82, AJAP1, C1orf174, ODZ4, NARS2, PRR16, FTMT, PCDH20, TDRD3, LBXCOR1, MAP2K5, PTGER3, ZRANB2, AXUD1, TTC21A, GFRA2, DOK2, SLC39A14, PPP3CC, VPS26B, NCAPD3, ZNF236, MBP, RIN2, NAT5, SEMA5A, MTRR, DGKB, ETV1, BHLHB5, CYP7B1, TMEPAI, ZBP1, TBC1D1, KLHL1, DACH1, LRRTM4, C2orf3, B3GAT1, LOC89944, ATP8B4, SLC27A2, CHD6, EMILIN3, RWDD3, TMEM56, SCN1A, KIBRA, and NCAN, associated with memory performance, include the SNVs listed in Table 36.

TABLE 36

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 196 | rs4420638 | 19 | 45422946 | A | G | APOC1, APOE | 0.82 | 1E−16 | 8.27 | AACTAGATTGAACCCTCAGCCTAGCAATGTCACTATGCTACACTTTTCCT[A/G]GTGTGGTCTACCCGAGATGAGGGGCTGAGGTTTTTTTTTGTTTTTGTTTC |
| 197 | rs7594645 | 2 | 207646674 | G | A | FASTKD2, MIR3130-1, MIR3130-2 | 0.07 | 4E−09 | 0.07 | TAGAAACCAGCTCCTTGGACAGCTCACCAAAAGGCTAGGATGTTGAAGAC[A/G]TGCTCCACTCCTCTCATTTCCTCCTGAGGCTGAATCCTCGGGTTGCGTAC |
| 198 | rs6813517 | 4 | 168522751 | T | C | SPOCK3, ANXA10 | 0.79 | 3E−08 | 0.37 | AACAACTATTTCCCAGTTTTTGTAAAATGTTCATTTCTTAGCTCCTCCT[T/C]AGCCTTTATTTAATCCATACACTCTTAAATCTTTGCTTGGATCAATAAGA |
| 199 | rs10058621 | 5 | 50555169 | T | C | ISL1, PARP8 | 0.94 | 3E−08 | 0.76 | GTCTCTTTTCTGGTGATTAAAAGTCATTATCACCTAGTCATTACTACCAA[T/C]GAGATAATTAGACATTTCAAACAAACAATTTAAAACAAGATGTATTCCT |

TABLE 36-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 200 | rs8067235 | 17 | 79024637 | A | G | BAIAP2 | 0.33 | 6E−08 | 0.15 | ACAGATGT GCATGCAG ACATGAGC ACACGCAC ACCAGAAC ACTAGAGT CG[G/A]CC GCATCCTC CTCACTTG GCTGATGC CCCCTTCT GCTTGATT TCATCACA |
| 201 | rs11074779 | 16 | 26451443 | T | C | HS3ST4, C16orf82 | 0.81 | 1E−07 | 0.38 | CATTCCTT TTTTTCAC CTAAATAG CATTCTCT GTCTTGGC CAAGCTGA CC[T/C]GTC CCTGTCTT CCACATGC ATCTTGCA CTTTTTGA TGTCCTGT TATTCAC |
| 202 | rs932350 | 1 | 4853688 | T | C | AJAP1, C1orf174 | 0.32 | 2E−07 | 0.11 | AATGTCTT TTCACATA TTTGAAAT TACCTGAA CCTATCAC CAAGGTCA TA[T/C]GCA TCATCCAT GTATGACT TTGCCCCA CTTGCCAA ATGGGGCA GACCAAG |

In some embodiments, the mental condition comprises obsessive compulsive disorder (OCD) predisposition. OCD predisposition may be affected by genetic variations within genes encoding PTPRD, LOC646114, LOC100049717, FAIM2, AQP2, TXNL1, WDR7, CDH10, MSNL1, GRIK2, HACE1, DACH1, MZT1, DLGAP1, EFNA5, and/or GRIN2B. Non-limiting examples of genetic variations within genes encoding PTPRD, LOC646114, LOC100049717, FAIM2, AQP2, TXNL1, WDR7, CDH10, MSNL1, GRIK2, HACE1, DACH1, MZT1, DLGAP1, EFNA5, and GRIN2B, associated with OCD predisposition, include the SNVs listed in Table 37.

TABLE 37

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 203 | rs4401971 | 9 | 11890045 | G | A | PTPRD, LOC646114, LOC100049717 | 0.59 | 4E−07 | NR | AGTTTTCT TTCTTTTCT TTTCTTTTC TTTTTTTTG TTTGTTTG TCATGTC[A/G]TTCCCT GGTTTTGG TACTGGCT TTATAGAA TGATGGTG ATACTGGC TTTA |
| 204 | rs297941 | 12 | 50319086 | A | G | FAIM2, AQP2 | 0.53 | 5E−07 | 0.21 | GTGTCCCA GGCACTGT GTTAGGAT TCACTGAG TTGTCACA AAAATCCT |

TABLE 37-continued

| SEQ ID NO | SNV | Chr (Build 37) | Position (Build 37) | RISK ALLELE | NON RISK ALLELE | GENE | RISK ALLELE FREQUENCY | P-VALUE | BETA | Variant with Flanking Sequence |
|---|---|---|---|---|---|---|---|---|---|---|
| 205 | rs12959570 | 18 | 54333584 | G | A | TXNL1, WDR7 | 0.23 | 9E-07 | 0.18 | GC[A/G]AAGTTCATTCTCGAGGACGCTCTGGAATTTAAATACCTTGCCAAGATCATAAGCGATTCTCCTGCCTTAGCCTTTCTAGTAGCTGGGATTACAGGCATGC[G/A]CCACCATGCCCAGCTAATTTTTTATTTTTAGTAGAGACGGGGTTTCTCCA |
| 206 | rs6876547 | 5 | 25572301 | G | T | CDH10, MSNL1 | 0.19 | 2E-06 | NR | CAGCTCATTCATGAACAATGACTGAGTATATGTGATCCAAATGCACAGGG[T/G]GTTATCCTGAGAAAGCAATCAGCCTTGTGGGCCAGATAAATCCATTATAA |
| 207 | rs9499708 | 6 | 104445367 | T | C | GRIK2, HACE1 | 0.67 | 3E-06 | 0.18 | ATTCTCCAGGGATTTGCTACCATCTTTATTGTCTGAAAAAGAATTTGATA[C/G/T]GTCATATTCTCTATTCTGTTCATATTTTAATATCTGAAGCCTATGCTCAT |
| 208 | rs9652236 | 13 | 72688774 | T | G | DACH1, MZT1 | 0.18 | 5E-06 | 0.34 | AACTGGAACTAGGTTAAGCAAAGTAACATTTCAAAAGGGAAGATTCAGTG[G/T]AAGTTTTCTGGGATTGCTCACAGAATCCAAGAATGGGCTGCAGGTATCAG |
| 209 | rs11081062 | 18 | 3662879 | T | C | DLGAP1 | 0.36 | 4E-04 | 0.81 | TATCCCATCCCTGTATTATCAGTATACGTTGGACATATATGAGGCAAATA[C/T]CTTTTCATATTGAGAGGTCTTCATATTGAGAGAAATTGTATAAGACAAC |

Hair Trait

Disclosed herein, in some embodiments, are hair traits. In some embodiments, a hair trait comprises hair thickness, hair thinning, hair loss, baldness oiliness, dryness, dandruff, pseudofolliculitis barbae (razor bumps), monilethrix, pili trianguli, pili torti, and/or hair volume. In some embodiments, the term "baldness," as used herein, refers to androgenetic alopecia (AGA). In some embodiments, the pili trianguli may be affected by genetic variations within genes encoding PADI3, TGM3, and/or TCHH. In some embodiments, the pseudofolliculitis barbae may be affected by genetic variations within genes encoding K6HF. In some embodiments, the monilethrix may be affected by genetic variations within genes encoding KRT81, KRT83, KRT86, and/or DSG4. In some embodiments, pili torti may be affected by genetic variants within genes encoding BCS1L. In some embodiments, baldness may be affected by genetic variations within genes encoding AR, PAX1, FOXA2, HLA-DQA2, ULBP3, ULBP6, EDA2R, BQ013595, PAX1, BE789145, WNT10A, ICOS, CTLA4, HDAC4, HDAC9, IL2RA, EBF1, TARDBP, SSPN, ITPR2, SUCNR1, MBNL1, MAPT-AS1, SPPL2C, AUTS2, SETBP1, GRID1, EDA2R, IKZF4, IL2, IL21, STX17, and/or PRDX5. Non-limiting examples of genetic variations within AR, PAX1, FOXA2, HLA-DQA2, ULBP3, ULBP6, EDA2R, BQ013595, PAX1, BE789145, WNT10A, ICOS, CTLA4, HDAC4, HDAC9, IL2RA, EBF1, TARDBP, SSPN, ITPR2, SUCNR1, MBNL1, MAPT-AS1, SPPL2C, AUTS2, SETBP1, GRID1, EDA2R, IKZF4, IL2, IL21, STX17, that are associated with baldness, include the SNVs listed in Table 38.

TABLE 38

| SEQ ID NO | SNV | Chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 212 | rs2497938 | X | 66563018 | T | C | AR | 0.85 | 2E−91 | 79 | GCCAAAGATCCTGAATACCAAGCCCTCAGAAAATGGTAAAGCACTGTAAG[T/C]ATCTTAATTGTCAGCATTATCACAACTACAAATGGCAAAGCTGGGTGGAG |
| 213 | rs6047844 | 20 | 22037575 | T | C | PAX1, FOXA2 | 0.46 | 2E−39 | .47 | TTTTATAATTTAGGAATTTCCACATTATTAAGTCAGGATAGCCAGTATAG[T/C]AGAGATACAGGTGTCCAATATCCCTTTCATCCTTCTTCCTTTAGTAATAG |
| 214 | rs9275572 | 6 | 32678999 | G | A | HLA-DQA2 | 0.59 | 1E−35 | .79 | GGGAAAAAATTAATTGTTGTTAAGAATTATGGTGATTCTGCTCCATAGCA[A/G]CTTCATTAAAGGACCTAGTCTAAGTTCAAGATTAAAAGGTTATATGAGGC |
| 215 | rs9479482 | 6 | 150358012 | A | G | ULBP3, ULBP6 | 0.57 | 4E−19 | .50 | TTAAATATAAGCCCATAGGCACTCTGCTGCATGCAGATTCTATCTCAAAA[T/C]AAAACACTCTGAAGATGTTCCAAGACCCACACATACAGATTCTTTTCCTT |
| 216 | rs1385699 | X | 65824986 | T | C | EDA2R | 0.70 | 4E−19 | .54 | TGACCTTCTGAACACGATTGATGACAGCACAGGTGATGCAACTCTGACAT[C/T]TGTGGTGGCCCCAGCTGCTTT |

TABLE 38-continued

| SEQ ID NO | SNV | chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 217 | rs2180439 | 20 | 21853100 | T | C | BQ013595, PAX1, BE789145 | 0.57 | 3E-15 | .60 | TGTACCTGCGAGGAGGGCAGGCTGTGCAGTGAGCCAGTCTCTTCTCTTTAAGTTGATGCTAGCTGCCGTTTTGTGTTAT[C/T]TGTTACAGACTAATACAATTTGCAATAATTGAAGATGCAATATTTATTGA |
| 218 | rs7349332 | 2 | 219756383 | T | C | WNT10A | NR | 4E-15 | .29 | TGCCTCCTCCTCCTCCTCCTCGTTAAACTGGTTAATTAATGGCTGCTGCC[C/T]GTGGGAAGCAGATGTTCTGGAGCTGTTGGCCTGGGGAGGCATTGGTCTGG |

Behavioral Modifications

Aspects disclosed herein provide methods and systems for recommending to an individual a behavioral modification related to a specific phenotypic trait, based at least in part, on the genetic risk score (GRS) for that trait. In some instances, a plurality of recommendations of behavior modifications are provided to the individual. In some instances, a survey of the individual is provided by the individual comprising questions related to the specific phenotypic trait of interest. In some instances, the behavior modifications are based on the GRS for the trait, and the answers to the questions received from the individual. In some instances, the behavior modification comprises increasing, reducing, or avoiding an activity. Non-limiting examples of activities include, but are not limited to, comprising a physical exercise, ingestion of a substance (e.g., supplement or drug), exposure to a product (e.g., fumes, toxins, irritants, and the like), usage of a product (e.g., skin care product, hair care product, nail care product, and the like), a diet, a lifestyle, sleep, and consumption (e.g., consumption of alcohol, a drug, caffeine, an allergen, a food or category of foods). In some instances, the behavior modification comprises an activity to remedy or prevent the specific phenotypic trait (for e.g., engaging or not engaging in an activity that serves as a cause or a correlative to the occurrence of the specific phenotypic trait).

The present disclosure provides, by way of non-limiting examples, various recommendations of behavior modifications related to the specific phenotypic traits described herein. In some embodiments, an individual with a GRS indicating an increased likelihood for dry skin, as compared to a subject population, is recommended to engage in an activity to remedy and/or prevent dry skin (e.g., apply moisturizer on a daily basis). In some embodiments, an individual with a GRS indicating an increased likelihood for collagen breakdown, as compared to a subject population, is recommended to engage in an activity to remedy and/or prevent collagen breakdown (e.g., consumption of collagen supplement, use of a particular product or device, avoidance of a particular product or device). In some embodiments, an individual with a GRS indicating an increased likelihood of exercise aversion, as compared to a subject population, is recommended to engage in non-conventional physical activity (e.g., hobbies such as rock-climbing, hiking, backpacking, and the like). In some embodiments, an individual with a GRS indicating an increased likelihood for muscle damage risk, as compared to a subject population, is recommended to avoid activity to remedy or prevent muscle damage (e.g., body building, extreme endurance events, and the like). In some embodiments, an individual with a GRS indicating an increased likelihood for stress fractures, as compared to a subject population, is recommended to avoid activity to remedy of prevent stress fractures (e.g., repetitive and/or high-impact activities such as running). In some embodiments, an individual with a GRS indicating an increased likelihood to metabolize alcohol poorly, as compared to a subject population, is recommended to avoid consumption of alcohol, or to reduce alcohol consumption. In some embodiments, the subject population is ancestry-specific to the individual.

Systems

Aspects disclosed herein provide systems configured to implement the methods described in this disclosure, including, but not limited to, determining a likelihood that an individual has, or will develop a specific phenotypic trait.

FIG. 1 describes exemplary wellness reporting systems comprising a computing device comprising at least one processor 104, 110, a memory, and a software program 118 including instructions executable by at least one processor to assess a likelihood that an individual has, or will develop, a specific phenotypic trait. In some instances, the system comprises a reporting module configured to generate a report the GRS to the individual. In some instances, the report comprises a recommendation of a behavioral modification related to the specific phenotypic trait. In some instances, the system comprises an output module configured to display the report to the individual. In some instances, the system comprises a central processing unit (CPU), memory (e.g., random access memory, flash memory), electronic storage unit, software program, communication interface to communicate with one or more other systems, and any combination thereof. In some instances, the system is coupled to a computer network, for example, the Internet, intranet, and/or extranet that is in communication with the Internet, a telecommunication, or data network. In some instances, the system is connected to a distributed ledger. In some instances, the distributed ledger comprises blockchain. In some embodiments, the system comprises a storage unit to store data and information regarding any aspect of the methods described in this disclosure. Various aspects of the system are a product or article or manufacture.

The exemplary wellness reporting systems of FIG. 1, comprise one feature of a software program that includes a sequence of instructions, executable by the at least one processor, written to perform a specified task. In some embodiments, computer readable instructions are implemented as program modules, such as functions, features, Application Programming Interfaces (APIs), data structures, and the like, that perform particular tasks or implement particular data types. In light of the disclosure provided herein, those of skill in the art will recognize that a software program may be written in various versions of various languages. In some embodiments, the software program 118 includes instructions executable by the at least one processor described herein. In some embodiments, the instructions comprise the steps of: (i) providing the genotype of the individual, the genotype comprising one or more individual-specific genetic variants; (ii) assigning an ancestry to the individual based, at least in part, on the genotype of the individual 106; (iii) using a trait-associated variants database 108 comprising ancestry-specific genetic variants derived from subjects with the same ancestry as the individual (subject group) to select one or more ancestry-specific genetic variants based, at least in part, on the ancestry of the individual, wherein each of the one or more ancestry-specific genetic variants correspond to: (1) an individual-specific genetic variant of the one or more individual-specific genetic variants, or (2) a predetermined genetic variant in a linkage disequilibrium (LD) with an individual-specific genetic variant of the one or more individual-specific genetic variants in a subject population with the same ancestry as the individual, and wherein each of the one or more ancestry-specific genetic variants and each of the individual specific genetic variants comprises one or more units of risk; and (iv) calculating a genetic risk score 112 for the individual based on the selected one or more ancestry-specific genetic variants, wherein the genetic risk score is indicative of the likelihood that the individual has, or will develop the specific trait. In some embodiments, the software program 118 further comprises instructions executable by the at least one processor described herein comprising predetermining a genetic variant in LD with the individual-specific genetic variant. In some instances, the software program includes instructions executable by the at least one processor to determine the predetermined genetic variant, the instructions comprising the steps of: (i) providing unphased genotype data from an individual; (ii) phasing the unphased genotype data to generate individual-specific phased haplotypes based on the ancestry of the individual; (iii) imputing individual-specific genotypes not present in the phased individual-specific phased haplotypes using phased haplotype data from a reference group that has the same ancestry as the individual; and (iv) selecting a genetic variant from the imputed individual-specific genotypes that is in linkage disequilibrium (LD) an individual-specific genetic variant associated with a likelihood that the individual has, or will develop, a specific trait. In some embodiments, the LD is defined by a D' value at least about 0.20, 0.25, 0.30, 0.35, 0.40, 0.45, 0.50, 0.55, 0.60, 0.65, 0.70, 0.75, 0.80, 0.85, 0.90, 0.95 or 1.0. In some embodiments, the LD is defined by a $r^2$ value at least about 0.70, 0.75, 0.80, 0.85, 0.90, 0.95, or 1.0.

The functionality of the computer readable instructions are combined or distributed as desired in various environments. In some instances, a software program comprises one sequence of instructions or a plurality of sequences of instructions. A software program may be provided from one location. A software program may be provided from a plurality of locations. In some embodiment, a software program includes one or more software modules. In some embodiments, a computer program includes, in part or in whole, one or more web applications, one or more mobile applications, one or more standalone applications, one or more web browser plug-ins, extensions, add-ins, or add-ons, or combinations thereof.

FIG. 1 describes an exemplary wellness reporting system comprising a reporting module 114. The reporting module 114 described herein comprises at least one processor configured to perform the task of generating a report comprising the calculated GRS of the individual indicative of a likelihood that the individual has, or will develop, a specific phenotypic trait of interest. In some instances, the at least one processor is the same processor 118 described above, and additionally configured to perform the steps of generating the report. In some instances, the at least one processor comprises a separate processor, such as in a dual-CPU. In some instances, the reporting module 114 is configured to perform the task of retrieving one or more answers to one or more questions relating to the specific trait in a survey provided to the system by the individual. In some instances, the report further comprises a recommendation of a behavioral modification related to the trait based, at least in part, on the GRS. In some instances, the report generated by the reporting module 114 comprises a recommendation of a behavior modification related to the specific phenotypic trait of interest based on the GRS for that trait and retrieved one or more answer to the one or more questions relating to the trait.

In some embodiments, the exemplary wellness reporting systems of FIG. 1 comprise an output module 116. The output module 116 described herein comprises a hardware, or software program capable of being performed on a processor, configured to display the report to the individual. In some embodiments, the output module 116 comprises user interface, including a screen, or other output display (e.g., projector). In some embodiments, the output module 116 comprises emailing service capable of emailing an electronic version of the report to the individual to which it belongs. In some embodiments, the output module 116 comprises a user interface on a personal computing device, such as a computer, smartphone, or tablet. In some embodiments, the personal computing device is remotely connected, via a computer network, to the system described herein. In some instances, the personal computing device belonging to the individual. In some embodiments, the personal electronic device is configured to run an application configured to communicate with the reporting module via a computer network to access the report.

Web Application

In some embodiments, the software programs described herein include a web application. In light of the disclosure provided herein, those of skill in the art will recognize that a web application may utilize one or more software frameworks and one or more database systems. A web application, for example, is created upon a software framework such as Microsoft® .NET or Ruby on Rails (RoR). A web application, in some instances, utilizes one or more database systems including, by way of non-limiting examples, relational, non-relational, feature oriented, associative, and XML database systems. Suitable relational database systems include, by way of non-limiting examples, Microsoft® SQL Server, mySQL™, and Oracle®. Those of skill in the art will also recognize that a web application may be written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). A web application may integrate enterprise server products such as IBM® Lotus Domino®. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity®.

Mobile Application

In some instances, software programs described herein include a mobile application provided to a mobile digital processing device. The mobile application may be provided to a mobile digital processing device at the time it is manufactured. The mobile application may be provided to a mobile digital processing device via the computer network described herein.

A mobile application is created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, the software programs described herein include a standalone application, which is a program that may be run as an independent computer process, not an add-on to an existing process, e.g., not a plug-in. Those of skill in the art will recognize that standalone applications are sometimes compiled. In some instances, a compiler is a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Perl, R, Python™, Visual Basic, and VB .NET, or combinations thereof. Compilation may be often performed, at least in part, to create an executable program. In some instances, a computer program includes one or more executable complied applications.

Web Browser Plug-in

Disclosed herein, in some embodiments, are software programs that, in some aspects, include a web browser plug-in. In computing, a plug-in, in some instances, is one or more software components that add specific functionality to a larger software application. Makers of software applications may support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands. Those skilled in the art will recognize that several plug-in frameworks are available that enable development of plug-ins in various programming languages, including, by way of non-limiting examples, C++, Delphi, Java™ PHP, Python™, and VB .NET, or combinations thereof.

In some embodiments, Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser, in some instances, is a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The medium, method, and system disclosed herein comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. In some embodiments, a software module comprises a file, a section of code, a programming feature, a programming structure, or combinations thereof. A software module may comprise a plurality of files, a plurality of sections of code, a plurality of programming features, a plurality of programming structures, or combinations thereof. By way of non-limiting examples, the one or more software modules comprises a web application, a mobile application, and/or a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The medium, method, and system disclosed herein comprise one or more databases, such as the trait-associated database described herein, or use of the same. Those of skill in the art will recognize that many databases are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some embodiments, a database is internet-based. In some embodiments, a database is web-based. In some embodiments, a database is cloud computing-based. A database may be based on one or more local computer storage devices.

Data Transmission

The methods, systems, and media described herein, are configured to be performed in one or more facilities at one or more locations. Facility locations are not limited by country and include any country or territory. In some instances, one or more steps of a method herein are performed in a different country than another step of the method. In some instances, one or more steps for obtaining a sample are performed in a different country than one or more steps for analyzing a genotype of a sample. In some embodiments, one or more method steps involving a computer system are performed in a different country than another step of the methods provided herein. In some embodiments, data processing and analyses are performed in a different country or location than one or more steps of the methods described herein. In some embodiments, one or more articles, products, or data are transferred from one or more of the facilities to one or more different facilities for analysis or further analysis. An article includes, but is not limited to, one or more components obtained from a sample of a subject and any article or product disclosed herein as an article or product. Data includes, but is not limited to, information regarding genotype and any data produced by the methods disclosed herein. In some embodiments of the methods and systems described herein, the analysis is performed and a subsequent data transmission step will convey or transmit the results of the analysis.

In some embodiments, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein is transferred to and/or received from a facility located within the same or different countries, including analysis of a data input, such as cellular material, performed in one facility in a particular location and corresponding data transmitted to another location, or directly to an individual, such as data related to the diagnosis, prognosis, responsiveness to therapy, or the like, in the same or different location or country.

Non-Transitory Computer Readable Storage Medium

Aspects disclosed herein provide one or more non-transitory computer readable storage media encoded with a software program including instructions executable by the operating system. In some embodiments, software encoded includes one or more software programs described herein. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

EXAMPLES

Example 1. Calculating an Ancestry-Specific Genetic Risk Score for an Individual Representing a Likelihood that the Individual Will have Better Aerobic Performance First, a genotype of an individual is provided. The genotype of the individual may be in the format of an Illumina Genotyping Array. The genotype includes genetic risk variants specific to the individual (individual-specific genetic risk variants). The genetic risk variants may include single nucleotide variants (SNVs), single nucleotide polymorphisms (SNPs), indels, and/or copy-number variants (CNVs). The Illumina Genotyping Array comprises nucleic acid probes specific to various SNVs, indels, SNPs, and/or CNVs. Using principal component analysis (PCA), the genotype is analyzed to determine the ancestry of the individual, and the individual is determined to be of African descent.

Next, reference genetic variants are selected from genome wide associate studies (GWAS) of subjects with the same ancestry as the individual (e.g., African)(ancestry-specific subject group), as determined by PCA. The ancestry-specific variants are located at reported susceptibility genetic loci for aerobic performance comprising TSHR, ACSL1, PRDM1, DBX1, GRIN3A, ESRRB, ZIC4, and/or CDH13, and are selected based on a strong association (P=1.0×10$^{-4}$ or lower) between the ancestry-specific genetic variants and the aerobic performance trait. The variants are provided in Table 39.

selected to serve as the basis for the genetic risk calculations. A proxy genetic variant is selected, also known as "imputation," if it is in linkage disequilibrium (LD) ($r^2$ value of at least 0.70 or D' value of at least about 0.20) with the unknown individual-specific genetic risk variant.

Next, an individual-specific raw score is calculated. Numerical values are assigned to units of risk (e.g., risk alleles) within the individual-specific genetic variants, and all numerical values for each individual-specific genetic variant are added together, and divided by the total number

TABLE 39

| SEQ ID NO | SNV | Chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 54 | rs7144481 | 14 | 81610942 | C | T | TSHR | NR | 9E-08 | NR | AAGTTAGGCTACCAGCATATTTGAATGCCAGGTGAAATCAAAATAATCTA[C/T]ACTATCTAGAAGACTTTCTTGATGCCAAGTCCAGAGATGTCATTGTGTAG |
| 55 | rs6552828 | 4 | 185725416 | G | A | ACSL1 | NR | 1E-06 | NR | TTTAAACCAACCACCAGATATCTAAAGAGGGAATACAGCACAGTGTTGGA[A/G]AGAAAGTACAGAATAGTATTTGAGATCCTAGATGCAGCCGGACGCGGTGG |
| 56 | rs10499043 | 6 | 106247137 | A | G | PRDM1 | 0.13 | 4E-06 | NR | GCAATGTCCTTGTTTGTGTTCTCTCCCAGTGTTCCAGGTTCTACTGTCAA[C/T]CCAGGCTCAGGCTGTCCCACATCCTCCCACAGAGGTCTTGCTTTGTTTTG |
| 57 | rs10500872 | 1 | 20245723 | A | G | DBX1 | NR | 6E-06 | NR | TGAGAGGAATTCAATCTGAACAAATTTAAGCAAAAGGGATCTTTAGTATG[T/C]GGATTTTGTCATTTTCTAGTAGACACCAAGGACAGGGCTGTAGTGGGGCC |
| 58 | rs1535628 | 9 | 105016749 | G | A | GRIN3A | 0.09 | 7E-06 | NR | AGAGGATGCTAGGTATCTCAAGGTAGGAAAGCATATCTGTGGACAGAAAG[G/A]ACTGTAGAATAGCCAAATCAGAGGGAAGGGCCACTCTACCTAGTTCAGTG |
| 59 | rs12893597 | 4 | 76812695 | T | C | ESRRB | NR | 7E-06 | NR | AACTGCTATGTGTCCTAAGTGGGAATGCTAACCCCTCTGATCGGCTGAGA[C/T]GCCTACAGCCCAGCCTTCTCTAAATCCCCAAAGGCCAGACCCTGAAATGA |
| 60 | rs11715829 | 3 | 146957166 | A | G | ZIC4 | 0.08 | 9E-06 | NR | TCACCAATATATTATTTTACTTATCAGTGAAATCAAAGGACTTTACATAT[T/C]TAGATTCCAAAACAACCTATTGTGATAATTTCTTACCTAGAAAGGTTTCT |

If an individual-specific genetic risk variant is unknown, meaning the identification number of the genotyping array corresponding to the individual-specific genetic variant is unpublished in the GWAS above, a proxy genetic variant is of the individuals-specific genetic variants and/or proxy genetic variants to generate an individual-specific raw score.

Next, the same calculations are performed to generate a raw score for each individual within the ancestry-specific subject group, thereby generating an observed range of raw scores (observed range). Next, the individual-specific raw score is compared to the ancestry-specific observed range to calculate a percentage of risk relative to the ancestry-specific subject population. Next, a genetic risk score (GRS) is assigned to the individual.

For example, to calculate the GRS for an individual for aerobic performance comprised of seven genetic variants, in this example SNPs (rs7144481 with risk allele C, rs6552828 with risk allele G, rs1049904 with risk allele A, rs10500872 with risk allele A, rs1535628 with risk allele G, rs1289359 with risk allele T, and rs1171582 with risk allele A) requires that each genotype be determined by actual genotyping or imputation and that the average of the sum of all risk alleles be calculated. Hence, an individual with genotypes rs7144481 (CC), rs6552828 (AA), rs1049904 (GG), rs10500872 (AG), rs1535628 (AA), rs1289359, (CT), rs1171582 (AA) has risk alleles of 2, 0, 0, 1, 0, 1, and 2, respectively, resulting in a sum of 6 with an average genetic risk score of 0.86 (=6/7; risk alleles divided by the total number of variants comprising the model). Table 40 provides exemplary calculations in accordance with the example provided.

TABLE 40

| Variant | Risk allele | Non-risk allele | Individual's genotype | Number of risk alleles |
|---|---|---|---|---|
| rs7144481 | C | T | CC | 2 |
| rs6552828 | G | A | AA | 0 |
| rs1049904 | A | G | GG | 0 |
| rs10500872 | A | G | AG | 1 |
| rs1535628 | G | A | AA | 0 |

TABLE 40-continued

| Variant | Risk allele | Non-risk allele | Individual's genotype | Number of risk alleles |
|---|---|---|---|---|
| rs1289359 | T | C | CT | 1 |
| rs1171582 | A | G | AA | 2 |
| | | | Total number of risk alleles | 6 |
| | | | Average number of risk alleles (6 risk alleles divided by 7 variants comprising the model) | 0.86 |

The GRS score is similarly calculated for the ancestry-specific population. When the individual's GRS score is compared to the distribution of GRS scores from the same ancestry-specific population, the individual's GRS score is in the $50^{th}$ percentile. The individual is predicted to have average aerobic performance.

Example 2. Calculating an Ancestry-Specific Genetic Risk Score for an Individual Representing a Likelihood that the Individual Will Experience Collagen Breakdown First, a genotype of an individual is provided. The genotype of the individual may be in the format of an Illumina Genotyping Array. The genotype includes genetic risk variants specific to the individual (individual-specific genetic risk variants). The genetic risk variants may include single nucleotide variants (SNVs), single nucleotide polymorphisms (SNPs), indels, and/or copy-number variants (CNVs). The Illumina Genotyping Array comprises nucleic acid probes specific to various SNVs, SNPs, and/or CNVs. Using principal component analysis (PCA), the genotype is analyzed to determine the ancestry of the individual, and the individual is determined to be Chinese.

Next, reference genetic variants are selected from GWAS. The variants are at reported susceptibility genetic loci MMP1, MMP3 and MMP9 for collagen breakdown and are selected based on strong association ($P=1.0 \times 10^{-4}$ or lower) between the genetic variations and the physical fitness trait. The variants are provided in Table 41.

TABLE 41

| SEQ ID NO | SNV | Chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 1 | rs495366 | 11 | 102695108 | G | A | MMP | 0.64 | 6E−34 | 0.44 | TGTCCTTTCTTA GCAGAGCAGGA TTTTGACCTAA ATTTCTGCAAA CTATA[G/A]TCT TATGGTTATGA CTCTTTTTGTAA GTTGATCACTC ATTCACAAGGA TG |
| 2 | rs11226373 | 11 | 104334239 | G | A | MMP-3, MMP-1 | 0.15 | 1E−18 | 0.44 | AATAAGCCCCC TCCCACTACTT CCCATTTATGA AATCTGTGGCA TACTAC[A/C/G] TTACTATTTCT ATGAACCTTTC CTGGATCACTT AACATGTTTAC TACAA |

If an individual-specific genetic risk variant is unknown, meaning the array identification number corresponding to the individual-specific genetic variant is unpublished in the GWAS above, a proxy genetic variant is selected to serve as the basis for the genetic risk calculations. A proxy genetic variant is selected if it is in linkage disequilibrium (LD) ($r^2$ value of at least 0.70 or D' value of at least about 0.20 based on subjects with the same ancestry as the individual) with the unknown individual-specific genetic risk variant.

Next, an individual-specific raw score is calculated. Numerical values are assigned to units of risk (e.g., risk alleles) within the individual-specific genetic variants, and all numerical values for each individual-specific genetic variant are added together, and divided by the total number of individual-specific genetic variants or proxy genetic variants, to generate an individual-specific raw score.

Next, the same calculations are performed to generate a raw score for each individual within the ancestry-specific subject group, thereby generating an observed range of raw scores (observed range). Next, the individual-specific raw score is compared to the ancestry-specific observed range to calculate a percentage of risk relative to the ancestry-specific subject population. Next, a genetic risk score (GRS) is assigned to the individual.

For example, to calculate the GRS for an individual for a collagen breakdown trait comprised of two genetic variants, in this example SNPs (rs495366 with risk allele G, and rs11226373 with risk allele G) requires that each genotype be determined by actual genotyping or imputation and that the average of the sum of all risk alleles be calculated. Hence, an individual with genotypes rs495366 (GG), rs11226373 (GA) has risk alleles of 2, and 1, respectively, resulting in a sum of 3 with an average genetic risk score of 1.5 (=3/2; risk alleles divided by the total number of variants comprising the model). Table 42 provides exemplary calculations in accordance with the present example.

TABLE 42

| Variant | Risk allele | Non-risk allele | Individual's genotype | Number of risk alleles |
|---|---|---|---|---|
| rs495366 | G | A | GG | 2 |
| rs11226373 | G | A | GA | 1 |
| | | | Total number of risk alleles | 3 |
| | | | Average number of risk alleles (3 risk alleles divided by 2 variants comprising the model) | 1.5 |

The GRS score is similarly calculated for the ancestry-specific population. When the individual's GRS score is compared to the distribution of GRS scores from the same ancestry-specific population, the individual's GRS score is in the 90$^{th}$ percentile. The individual is predicted to have high risk of collagen breakdown and is advised to hydrate their skin and apply collagen cream.

Example 3. Calculating an Ancestry-Specific Genetic Risk Score for an Individual Representing a Likelihood that the Individual Will Experience Vitamin A Deficiency First, a genotype of an individual is provided. The genotype of the individual may be in the format of an Illumina Genotyping Array. The genotype includes genetic risk variants specific to the individual (individual-specific genetic risk variants). The genetic risk variants may include single nucleotide variants (SNVs), single nucleotide polymorphisms (SNPs), indels, and/or copy-number variants (CNVs). The Illumina Genotype Chip comprises nucleic acid probes specific to various SNVs, SNPs, indels, and/or CNVs. Using principal component analysis (PCA), the genotype is analyzed to determine the ancestry of the individual, and the individual is determined to be Chinese.

Next, reference genetic variants are selected from GWAS that was published in a high-impact journal. The variants are at reported susceptibility genetic loci BCMO1, FFAR4 and TTR for Vitamin A deficiency and are selected based on strong association (P=1.0×10$^4$ or lower) between the genetic variations and the nutrition trait. The ancestry-specific variants are provided in Table 43.

TABLE 43

| SEQ ID NO | SNV | Chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 129 | rs6564851 | 16 | 81264597 | T | G | BCMO1 | 0.61 | 2E-24 | 0.15 | AAAGAAAGGG GGAAAGAATG CTCTGAGTGCC TACTGTATTTT AAGCACTG[T/G] GACATACACA GTTTTACACTG TTTAATTTAAA CTTTGTAGCCA GTCAATG |
| 210 | rs10882272 | 10 | 95348182 | C | T | FFAR4 | 0.35 | 7E-15 | 0.03 | GAACAGTTAAA GATGACTTACT TTTTTTTTTTT TCATTTATAAA AATGC[T/C]ATG GACCCTTTTAA GAGAATCGGCA TCATGAAATGA GAGAGAAAGT AGGA |

TABLE 43-continued

| SEQ ID NO | SNV | Chr (Build 37) | Position (Build 37) | RISK ALLELE | NON RISK ALLELE | GENE | RISK ALLELE FREQUENCY | P-VALUE | BETA | Flanking Sequence |
|---|---|---|---|---|---|---|---|---|---|---|
| 211 | rs1667255 | 18 | 29187279 | A | C | TTR | 0.31 | 6E−14 | 0.03 | CAGCAGTTTTG GAGATGGAAG CAATGCCAGAG ATGGGACTATT TCTTCTT[A/C]T TGTTTTAGATG TAAACATTAAA AAAAAAAAAA CAGGATGCACA CTTAGT |

If an individual-specific genetic risk variant is unknown, meaning the array identification number corresponding to the individual-specific genetic variant is unpublished in the GWAS above, a proxy genetic variant is selected to serve as the basis for the genetic risk calculations. A proxy genetic variant is selected if it is in linkage disequilibrium (LD) ($r^2$ value of at least 0.70 or D' value of at least about 0.20 based on subjects with the same ancestry as the individual) with the unknown individual-specific genetic risk variant.

Next, an individual-specific raw score is calculated. Numerical values are assigned to units of risk (e.g., risk alleles) within the individual-specific genetic variants, and all numerical values for each individual-specific genetic variant are added together, and divided by the total number of individual-specific genetic variants or proxy genetic variants, to generate an individual-specific raw score.

Next, the same calculations are performed to generate a raw score for each individual within the ancestry-specific subject group, thereby generating an observed range of raw scores (observed range). Next, the individual-specific raw score is compared to the ancestry-specific observed range to calculate a percentage of risk relative to the ancestry-specific subject population. Next, a genetic risk score (GRS) is assigned to the individual.

For example, to calculate the GRS for an individual for a vitamin A deficiency trait comprised of three genetic variants, in this example SNPs (rs6564851 with risk allele T, rs1082272 with risk allele C, and rs1667255 with risk allele A) requires that each genotype be determined by actual genotyping or imputation and that the average of the sum of all risk alleles be calculated. Hence, an individual with genotypes rs6564851 (TG), rs1082272 (TT), and rs1667255 (AC) has risk alleles of 1, 0, and 1, respectively, resulting in a sum of 2 with an average genetic risk score of 1.67 (=2/3; risk alleles divided by the total number of variants comprising the model). Table 44 provides exemplary calculations in accordance with the present example.

TABLE 44

| Variant | Risk allele | Non-risk allele | Individual's genotype | Number of risk alleles |
|---|---|---|---|---|
| rs6564851 | T | G | TG | 1 |
| rs1082272 | C | T | TT | 0 |
| rs1667255 | A | C | AC | 1 |
| | | | Total number of risk alleles | 2 |
| | | | Average number of risk alleles (2 risk alleles divided by the 3 variants comprising the model) | 0.67 |

The GRS score is similarly calculated in the ancestry-specific population. When the individual's GRS score is compared to the distribution of GRS scores from the same ancestry-specific population, the individual's GRS score 1 standard deviation above the mean. The individual is predicted to be at risk for vitamin A deficiency and is advised to take vitamin A supplements.

While preferred embodiments of the methods, media, and systems disclosed herein have been shown and described herein, such embodiments are provided by way of example only. Numerous variations, changes, and substitutions may be done without departing from the methods, media, and systems disclosed herein. It should be understood that various alternatives to the embodiments of the methods, media, and system disclosed herein may be employed in practicing the inventive concepts disclosed herein. It is intended that the following claims define the scope of the methods, media, and systems that methods and structures within the scope of these claims and their equivalents be covered thereby.

What is claimed:

1. A computer-implemented method of determining a likelihood that an individual has, or will develop, a specific phenotypic trait based on the ancestry of the individual, the method comprising:
  a. assigning an ancestry of the individual by using a distance-based or a models-based computer program to analyze a genotype of the individual, the genotype comprising one or more individual-specific genetic variants;
  b. selecting, from a trait-associated variants database comprising ancestry-specific genetic variants derived from subjects with the same ancestry as the individual (subject group), one or more ancestry-specific genetic variants based, at least in part, on the ancestry of the individual, wherein each of the one or more ancestry-specific genetic variants correspond to:
    i. an individual-specific genetic variant of the one or more individual-specific genetic variants, or
    ii. a predetermined genetic variant in a linkage disequilibrium (LD) with an individual-specific genetic variant of the one or more individual-specific genetic variants in a subject population with the same ancestry as the individual, wherein the predetermined genetic variant is predetermined by:
      1. phasing unphased genotype data from the individual to generate individual-specific phased haplotypes based on the ancestry of the individual;
      2. imputing individual-specific genotypes not present in the phased individual-specific phased haplotypes using phased haplotype data from a reference group that has the same ancestry as the individual; and
      3. selecting a genetic variant from the imputed individual-specific genotypes that matches with the individual-specific genetic variant associated with a likelihood that the individual has, or will develop, a specific phenotypic trait and corresponding to the one or more ancestry specific variants,
    wherein each of the one or more ancestry-specific genetic variants and each of the one or more individual specific genetic variants comprise one or more units of risk; and
  c. calculating a genetic risk score for the individual based on the selected one or more ancestry-specific genetic variants,
    wherein the genetic risk score is indicative of the likelihood that the individual has, or will develop the specific phenotypic trait.

2. The method of claim 1, wherein the one or more ancestry-specific genetic variants, the one or more individual-specific genetic variants, and the genetic variants in LD with the one or more individual-specific genetic variants comprise a Single Nucleotide Variant (SNV), an indel, and/or a Copy Number Variant (CNV).

3. The method of claim 2, wherein the one or more units of risk of the SNV comprises a risk allele; the one or more units of risk of the indel comprises a presence (I) or an absence (D) of the nucleotide; and the one or more units of risk of the CNV comprises an insertion or a deletion of a nucleic acid sequence.

4. The method of claim 1, further comprising providing a notification to the individual comprising the risk that the individual has, or will develop, the specific phenotypic trait.

5. The method of claim 1, wherein the specific phenotypic trait comprises a nutritional trait, a clinical trait, a subclinical trait, a physical exercise trait, a skin trait, a hair trait, an allergy trait, or a mental trait.

6. The method of claim 4, wherein the notification further comprises a recommendation for a behavior modification related to the specific phenotypic trait.

7. The method of claim 6, wherein the behavior modification related to the specific phenotypic trait comprises increasing, reducing, or avoiding an activity comprising performance of a physical exercise, ingestion of a drug, vitamin, or supplement, exposure to a product, usage of a product, a diet modification, sleep modification, alcohol consumption, or caffeine consumption.

8. A wellness reporting system comprising:
  a computing device comprising at least one processor, a memory, and a software program including instructions executable by at least one processor to assess a likelihood that an individual has, or will develop, a specific phenotypic trait, the instructions comprising the steps of:
    a. assigning an ancestry of the individual by using a distance-based or a models-based computer program to analyze a genotype of the individual, the genotype comprising one or more individual-specific genetic variants;
    b. selecting, from a trait-associated variants database comprising ancestry-specific genetic variants derived from subjects with the same ancestry as the individual (subject group), one or more ancestry-specific genetic variants based, at least in part, on the ancestry of the individual, wherein each of the one or more ancestry-specific genetic variants correspond to:
      i. an individual-specific genetic variant of the one or more individual-specific genetic variants, or
      ii. a predetermined genetic variant in a linkage disequilibrium (LD) with an individual-specific genetic variant of the one or more individual-specific genetic variants in a subject population with the same ancestry as the individual, wherein the predetermined genetic variant is predetermined by:
        1. phasing unphased genotype data from the individual to generate individual-specific phased haplotypes based on the ancestry of the individual;

2. imputing individual-specific genotypes not present in the phased individual-specific phased haplotypes using phased haplotype data from a reference group that has the same ancestry as the individual; and 3. selecting a genetic variant from the imputed individual-specific genotypes that matches with the individual-specific genetic variant associated with a likelihood that the individual has, or will develop, a specific phenotypic trait and corresponding to the one or more ancestry specific variants, wherein each of the one or more ancestry-specific genetic variants and each of the one or more individual specific genetic variants comprise one or more units of risk; and c. calculating a genetic risk score for the individual based on the selected one or more ancestry-specific genetic variants, wherein the genetic risk score is indicative of the likelihood that the individual has, or will develop the specific phenotypic trait;

a reporting module configured to generate a report comprising the genetic risk score of the individual for the specific phenotypic trait; and an output module configured to display the report to the individual.

9. The system of claim 8, wherein the one or more ancestry-specific genetic variants, the one or more individual-specific genetic variants, and the genetic variants in LD with the one or more individual-specific genetic variants comprise a Single Nucleotide Variant (SNV), an indel, and/or a Copy Number Variant (CNV).

10. The system of claim 9, wherein the one or more units of risk of the SNV comprises a risk allele; the one or more units of risk of the indel comprises an insertion (I) or a deletion (D) of the nucleotide; and the one or more units of risk of the CNV comprises an insertion or a deletion of a nucleic acid sequence.

11. The system of claim 8, wherein the report further comprises a recommendation for a behavior modification related to the specific phenotypic trait.

12. The system of claim 8, wherein the specific phenotypic trait comprises a nutritional trait, a clinical trait, a subclinical trait, a physical exercise trait, a skin trait, a hair trait, an allergy trait, or a mental trait.

13. The system of claim 8, further comprising a personal electronic device with an application configured to communicate with the output module via a computer network to access the report.

14. A non-transitory computer readable storage medium, comprising computer-executable code configured to cause at least one processor to perform steps comprising:

a. assigning an ancestry of the individual by using a distance-based or a models-based computer program to analyze a genotype of the individual, the genotype comprising one or more individual-specific genetic variants;

b. selecting, from a trait-associated variants database comprising ancestry-specific genetic variants derived from subjects with the same ancestry as the individual (subject group), one or more ancestry-specific genetic variants based, at least in part, on the ancestry of the individual, wherein each of the one or more ancestry-specific genetic variants correspond to:

i. an individual-specific genetic variant of the one or more individual-specific genetic variants, or ii. a predetermined genetic variant in a linkage disequilibrium (LD) with an individual-specific genetic variant of the one or more individual-specific genetic variants in a subject population with the same ancestry as the individual, wherein the predetermined genetic variant is predetermined by:

1. providing unphased genotype data from the individual;

2. phasing the unphased genotype data to generate individual-specific phased haplotypes based on the ancestry of the individual;

3. imputing individual-specific genotypes not present in the phased individual-specific phased haplotypes using phased haplotype data from a reference group that has the same ancestry as the individual; and 4. selecting a genetic variant from the imputed individual-specific genotypes that matches with the individual-specific genetic variant associated with a likelihood that the individual has, or will develop, a specific phenotypic trait; and c. calculating a genetic risk score for the individual based on the selected one or more ancestry-specific genetic variants, wherein the genetic risk score is indicative of the likelihood that the individual has, or will develop the specific phenotypic trait.

15. The medium of claim 14, wherein the one or more ancestry-specific genetic variants, the one or more individual-specific genetic variants, and the genetic variants in LD with the one or more individual-specific genetic variants comprise a Single Nucleotide Variant (SNV), an indel, and/or a Copy Number Variant (CNV).

16. The medium of claim 15, wherein each of the one or more ancestry-specific genetic variants and each of the individual specific genetic variants comprises one or more units of risk, and wherein the one or more units of risk of the SNV comprises a risk allele; the one or more units of risk of the indel comprises an insertion (I) or a deletion (D) of a nucleotide; and the one or more units of risk of the CNV comprises an insertion or a deletion of a nucleic acid sequence.

17. The medium of claim 14, wherein the steps further comprise providing a notification to the individual comprising the likelihood that the individual has, or will develop, the specific phenotypic trait.

18. The medium of claim 14, wherein the specific phenotypic trait comprises a nutritional trait, a clinical trait, a subclinical trait, a physical exercise trait, a skin trait, a hair trait, an allergy trait, or a mental trait.

19. The method of claim 1, wherein the distance-based computer program is principle component analysis, and wherein the models-based computer program is a maximum likelihood or a Bayesian method.

20. The system of claim 8, wherein the distance-based computer program is principle component analysis, and wherein the models-based computer program is a maximum likelihood or a Bayesian method.

* * * * *